(12) United States Patent
Liu et al.

(10) Patent No.: US 9,593,338 B2
(45) Date of Patent: Mar. 14, 2017

(54) SYNTHETIC TRANSCRIPTIONAL CONTROL ELEMENTS AND METHODS OF GENERATING AND USING SUCH ELEMENTS

(71) Applicant: The Regents of the University of California, Oakland, CA (US)

(72) Inventors: Chang Liu, Berkeley, CA (US); Adam P. Arkin, San Francisco, CA (US); Lei S. Qi, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 83 days.

(21) Appl. No.: 14/346,263

(22) PCT Filed: Sep. 27, 2012

(86) PCT No.: PCT/US2012/057530
§ 371 (c)(1),
(2) Date: Mar. 20, 2014

(87) PCT Pub. No.: WO2013/049330
PCT Pub. Date: Apr. 4, 2013

(65) Prior Publication Data
US 2015/0011007 A1    Jan. 8, 2015

Related U.S. Application Data

(60) Provisional application No. 61/540,413, filed on Sep. 28, 2011.

(51) Int. Cl.
| | | |
|---|---|---|
| *C12N 15/70* | (2006.01) | |
| *C12N 15/74* | (2006.01) | |
| *C12N 15/63* | (2006.01) | |
| *C12N 15/72* | (2006.01) | |
| *C07H 21/02* | (2006.01) | |
| *C07H 21/04* | (2006.01) | |
| *C12N 1/21* | (2006.01) | |
| *C12P 21/02* | (2006.01) | |

(52) U.S. Cl.
CPC ............ *C12N 15/72* (2013.01); *C07H 21/02* (2013.01); *C12N 15/63* (2013.01); *C12N 2830/001* (2013.01); *C12N 2840/002* (2013.01)

(58) Field of Classification Search
None
See application file for complete search history.

(56) References Cited

U.S. PATENT DOCUMENTS

| | | |
|---|---|---|
| 2007/0136827 A1 | 6/2007 | Collins et al. |
| 2011/0152213 A1 | 6/2011 | Breaker et al. |
| 2011/0152215 A1 | 6/2011 | Breaker et al. |

OTHER PUBLICATIONS

Ciamp, "Rho-dependent terminators and transcription termination" 152 Microbiology 2515-2528 (2006).*
Cambray, et al., "Toward Rational Design of Bacterial Genomes", Curr. Opin. Microbial. (2011), 14(5):624-630.
Gong, et al., "Instruction of Translating Ribosome by Nascent Peptide", Science (2002), 297(5588):1864-1867.
Gong, et al., "The Mechanism of Tryptophan Induction of Tryptophanase Operon Expression: Tryptophan Inhibits Release Factor-Mediated Cleavage of TnaC-Peptidyl-tRNA(Pro)", Proc. Natl. Acad. Sci. USA (2001), 98(16):8997-9001.
Liu, et al., "Regulation of Transcription by Unnatural Amino Acids", Nature Biotechnology (2011), 29(2):164-168.
Lucks, et al., "Multiplexed RNA Structure Characterization with Selective 2'-Hydroxyl Acylation Analyzed by Primer Extension Sequencing (SHAPE-Seq)", Proc. Natl. Acad. Sci. (2011), 108(27):11063-11068.
Lucks, et al., "Versatile RNA-Sensing Transcriptional Regulators for Engineering Genetic Networks", Proc. Natl. Acad. Sci. USA (2011), 108(21):8617-8622.
Zhao, et al., "Mg2+ Facilitates Leader Peptide Translation to Induce Riboswitch-Mediated Transcription Termination", EMBO J. (2011), 30(8):1485-1496.

\* cited by examiner

*Primary Examiner* — Nancy J Leith
(74) *Attorney, Agent, or Firm* — Bozicevic Field & Francis, LLP; Paula A. Borden; Glenn J. Foulds

(57) ABSTRACT

Provided herein are nucleic acid constructs that contain a synthetic control element that includes a cis-regulator of translation, and an adapter translation-coupled regulator of transcription. Further provided herein are nucleic acid constructs that contain nucleic acid sequences under the control of the synthetic control elements. Also provided are compositions and methods related to the nucleic acid constructs.

16 Claims, 19 Drawing Sheets

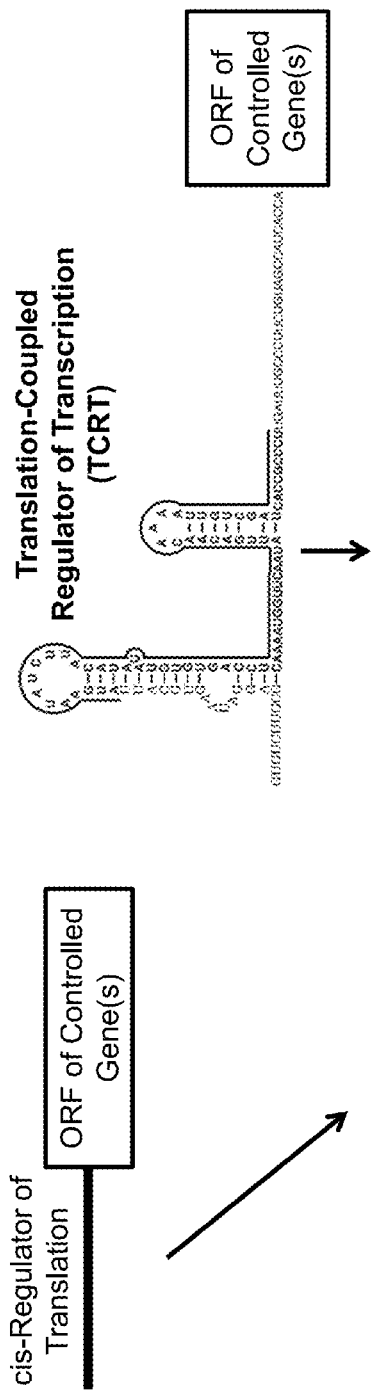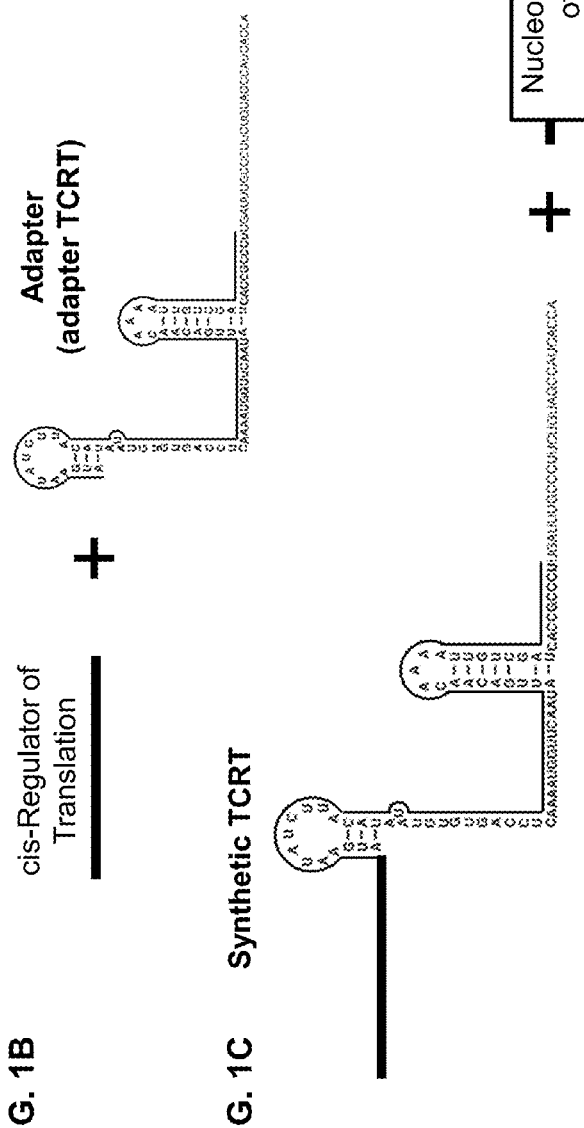
FIG. 1A
FIG. 1B
FIG. 1C  Synthetic TCRT

The translational regulator controls the
translational initiation of the gene

The translational regulator, when fused to the *tna* element adpater,
controls transcriptional elongation into the gene

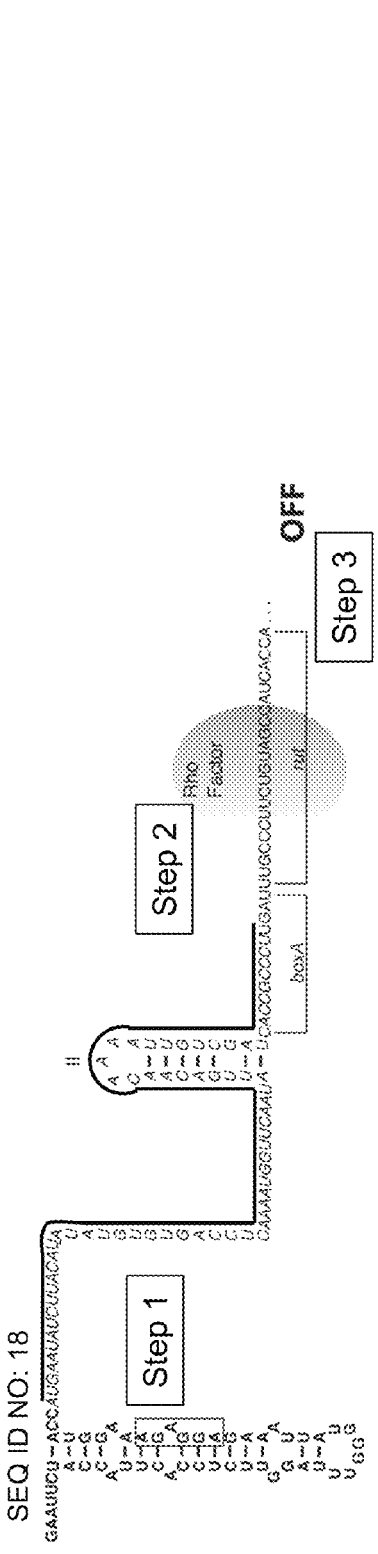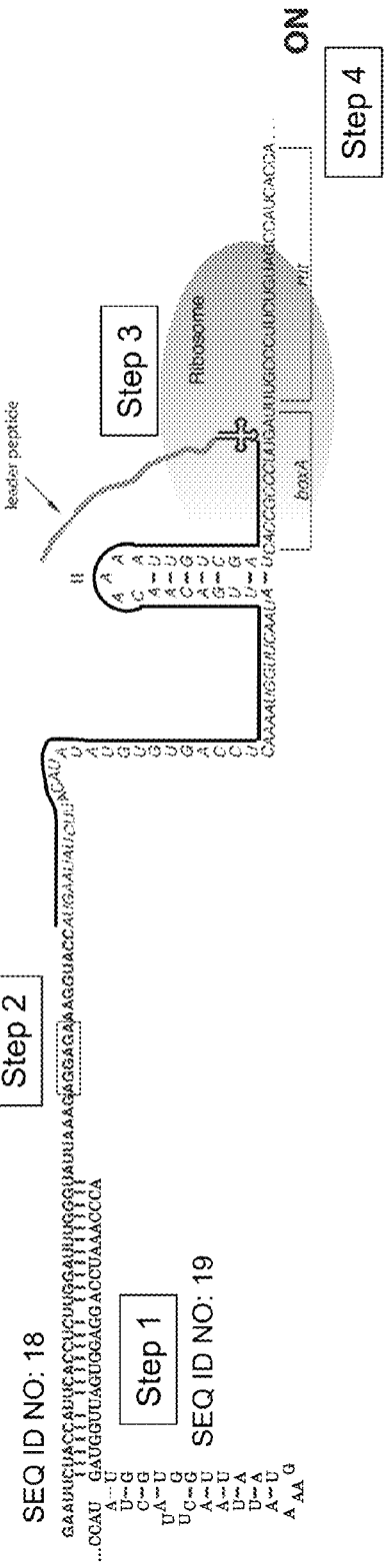
FIG. 5A
FIG. 5B

FIG. 9A

SEQ ID NO: 20

FIG. 9B

SEQ ID NO: 21

SEQ ID NO: 22

SEQ ID NO: 23

SYNTHETIC TRANSCRIPTIONAL CONTROL ELEMENTS AND METHODS OF GENERATING AND USING SUCH ELEMENTS

CROSS-REFERENCE

This application is a national stage application under 35 U.S.C.§371 PCT/US2012/057530, filed Sept. 27, 2012, which claims the benefit of U.S. Provisional Patent Application No. 61/540,413, filed Sep. 28, 2011, which applications are incorporated herein by reference in their entirety.

GOVERNMENT RIGHTS

This invention was made with Government support under grant numbers EEC-0540879 and EEC-0946510, awarded by the National Science Foundation. The government has certain rights in this invention.

SUBMISSION OF SEQUENCE LISTING ON ASCII TEXT FILE

A Sequence Listing is provided herewith as a text file, "BERK-197 WO_Seq_Listing.txt" created on Sep. 21, 2012 and having a size of 39 kilobytes. The contents of the text file are incorporated by reference herein in their entirety.

BACKGROUND

Much of a bacterium's regulatory potential is included in 5'-untranslated regions (5'-UTRs), which control the expression of physically adjacent downstream genes. Because of this cis action, the regulatory effects of 5'-UTRs are naturally constrained to the attached genes. As a result, 5'-UTRs have become attractive platforms for the parts-based approach to synthetic regulation, in which engineered regulatory parts that sense custom inputs and change the expression of desired genes in response are integrated.

In bacteria, there are two primary types of regulators found in 5'-UTRs that can serve as starting points for designing new parts. The first type of regulators found in 5'-UTRs includes regulators of translation (i.e., cis-regulators of translation), which link inputs to the accessibility of ribosome binding sites (RBSs). From a parts perspective, such regulators are attractive not only because they are well-represented in nature (e.g. riboswitches that sense small molecules, antisense RNA repressors and activators, and RBSs responsive to proteins, nutrients, pH, and temperature), but also because RBS-based interactions can be tuned or designed de novo using increasingly predictive thermodynamic models. However, cis-regulators of translation have a number of basic limitations: they can only control protein synthesis and not the production of RNAs, they are constrained to act on single genes, and they cannot simply be linked together into complex regulatory nodes as initiation at RBSs is a distributive process.

The second type of regulators found in 5'-UTRs includes regulators of transcriptional elongation (i.e., transcriptional continuation), which link cellular inputs to the continuation of RNA polymerase during RNA synthesis. In contrast to regulators of translation, these can control both the production of coding and non-coding RNAs and can act on entire operons including multiple genes. Furthermore, they are inherently composable because when multiple regulators of transcriptional elongation are linked in tandem in a 5'-UTR, the synthesis of the $N^{th}$ regulator is gated by the decision of the $(N-1)^{th}$ regulator; this predictably yields logic and higher-order functions. Hence, when engineering custom regulators for 5'-UTRs, one faces a restrictive tradeoff between ease of design for cis-regulators of translation and versatility of output for cis-regulators of transcriptional continuation. Thus, there is a need for custom regulators that are easy to design, that operate on entire operons and that can be composed into logics and higher-order functions. However, such regulators are difficult to engineer because their mechanisms involve action on a moving RNA polymerase, requiring the consideration of poorly defined kinetic and dynamic structural factors in their design. The existence of only a handful of synthetic regulators of transcriptional elongation, based either on riboswitches or the pT181 system, testifies to this difficulty.

SUMMARY

Provided herein is a strategy for converting cis-regulators of translation into synthetic translation-coupled regulators of transcription, and related compositions and methods. The synthetic translation-coupled regulators of transcription meet the aforementioned need of custom regulators that are easy to design, that operate on entire operons and that can be composed into logics and higher-order functions.

The compositions and methods provided herein involve a nucleic acid construct including a synthetic translation-coupled regulator of transcription (synthetic TCRT) that includes a cis-regulator of translation coupled to an adapter (an adapter translation-coupled regulator of transcription or "adapter TCRT"). The compositions and methods provided herein can include various cis-regulators of translation, and various adapter translation-coupled regulators of transcription.

Cis-regulators of translation included in the synthetic TCRTs provided herein may occur naturally, or they may not occur naturally. In some aspects, a cis-regulator of translation may be a modified version of a cis-regulator of translation that occurs naturally. In other aspects, a cis-regulator of translation may be designed de novo. Importantly, cis-regulators of translation are highly amenable to development and modification, due to importance of RNA structure for the function of many cis-regulators of translation. Because many factors affecting RNA structure are well-understood, cis-regulators of translation with desired characteristics may be designed and/or selected for by one of skill in the art. For example, the accessibility of a ribosome binding site in RNA may depend on whether or not the ribosome binding site is sequestered in an RNA stem-loop structure. The stability of various stem-loop structures may be calculated and/or predicted by one of skill in the art, due to the well-known binding properties between different nucleotides, and other factors. Accordingly, cis-regulators of translation wherein the ribosome binding site is sequestered in a stem-loop structure in certain conditions and not sequestered in a stem-loop structure in other conditions may be designed and/or prepared by one of skill in the art.

The synthetic TCRTs provided herein can be used to regulate the expression of a downstream nucleic acid sequence of interest. In addition, regulation of a nucleic acid sequence of interest by a synthetic TCRT provided herein may permit a large dynamic range for the expression of the regulated nucleic acid sequence of interest. For example, a nucleic acid sequence of interest placed under the control of a synthetic TCRT disclosed herein may have about a 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000-fold difference in expression between the activated state of the synthetic TCRT and the inactivated state of the synthetic TCRT.

Moreover, a cis-regulator of translation in a synthetic TCRT provided herein may provide a substantially larger dynamic range of expression of a regulated nucleic acid sequence of interest, as compared to the dynamic range of expression of a translation product regulated by the same cis-regulator of translation alone. For example, a cis-regulator of translation alone may only provide, for instance, a 20-fold difference in translated product between the activated and the inactivated state of the regulator. In contrast, if that same cis-regulator of translation is used in a synthetic TCRT provided herein, the synthetic TCRT may provide, for instance, a 700-fold difference in transcribed product between the activated and the inactivated state of the synthetic TCRT. Thus, the compositions and methods provided herein further provide a means for a large dynamic range of gene expression.

The expression of a nucleic acid sequence of interest may also be highly regulated by providing a nucleic acid sequence of interest under the control of two or more synthetic TCRTs provided herein. The expression of a nucleic acid sequence of interest under the control of two or more synthetic TCRTs is dependent upon the active state of each of the synthetic TCRTs. Accordingly, the expression of a nucleic acid sequence of interest under the control of two or more synthetic TCRTs may be highly regulated, based on the condition(s) necessary to activate expression from each of the synthetic TCRTs.

Relatedly, providing a nucleic acid sequence of interest under the control of two or more synthetic TCRTs provided herein may allow for precise regulation of the level of expression of the nucleic acid sequence of interest. The expression level of a nucleic acid sequence of interest under the control of two or more synthetic TCRTs provided herein may be different than the level of expression of the same nucleic acid sequence of interest obtained when the same nucleic acid sequence of interest is under the control any of the synthetic TCRTs alone.

In some embodiments, provided herein is a nucleic acid construct that includes a synthetic translation-coupled regulator of transcription (synthetic TCRT) that includes, in a 5' to 3' order: (a) a cis-regulator of translation and (b) an adapter translation-coupled regulator of transcription (adapter TCRT), wherein the cis-regulator of translation and the adapter TCRT are operably linked so that the transcription of downstream sequences (i.e., sequences that are 3' of and operably linked to the synthetic TCRT) is regulated by the cis-regulator of translation.

Also provided herein is a nucleic acid construct that includes a synthetic TCRT that includes, in a 5' to 3' order: (a) a cis-regulator of translation and (b) an adapter TCRT, wherein the cis-regulator of translation and the adapter translation-coupled regulator of transcription are operably linked so that transcription of downstream sequences (i.e., sequences that are 3' of and operably linked to the synthetic TCRT) is regulated by the cis-regulator of translation, wherein the nucleic acid construct further includes a nucleic acid sequence of interest, and wherein the nucleic acid sequence is operably linked to the synthetic TCRT which thereby regulates the expression of the nucleic acid sequence of interest.

Also provided herein is a nucleic acid construct that includes (i) a synthetic translation-coupled regulator of transcription that includes, in a 5' to 3' order: (a) a cis-regulator of translation, and (b) an adapter translation-coupled regulator of transcription, wherein (a) and (b) are operably linked so that the transcription of downstream sequences (i.e., sequences that are 3' of and operably linked to the synthetic TCRT) is regulated by (a); and (ii) a nucleic acid sequence of interest that is operably linked to the synthetic TCRT such that the synthetic TCRT regulates the expression of the nucleic acid sequence of interest, and wherein the nucleic acid sequence of interest includes a sequence selected from the group consisting of: (i) an insertion site, (ii) a sequence encoding a polypeptide coding sequence of interest, (ii) a sequence encoding an antisense RNA (iii) a sequence encoding a sense RNA, (iv) a sequence encoding a ribonucleic acid aptamer responsive to an environmental cue, and (v) a sequence encoding an RNA that is responsive to an intracellular or environmental cue.

Also provided herein is a nucleic acid construct that includes a synthetic TCRT that includes, in a 5' to 3' order: (a) a cis-regulator of translation and (b) an adapter TCRT, wherein the cis-regulator of translation and the adapter TCRT are operably linked so that the transcription of downstream sequences (i.e., sequences that are 3' of and operably linked to the synthetic TCRT) is regulated by the cis-regulator of translation, and wherein the cis-regulator of translation is: (i) a riboswitch that senses small molecules, (ii) a RBS-including sequence that is repressed or activated through antisense molecules, (iii) a nucleic acid aptamer responsive to an environmental cue, (iv) an RNA sequence responsive to an intracellular or environmental cue, or (v) a tuned ribosome binding site.

Also provided herein is a nucleic acid construct that includes a synthetic translation-coupled regulator of transcription that includes, in a 5' to 3' order: (a) a cis-regulator of translation and (b) an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, wherein the nucleic acid construct further includes a nucleic acid sequence of interest, wherein the nucleic acid sequence of interest is operably linked to the synthetic translation-coupled regulator of transcription which thereby regulates the expression of the nucleic acid sequence of interest, wherein the nucleic acid sequence of interest includes a sequence selected from the group consisting of: (i) an insertion site, (ii) a sequence encoding a polypeptide coding sequence of interest, (ii) a sequence encoding an antisense RNA (iii) a sequence encoding a sense RNA, (iv) a sequence encoding a ribonucleic acid aptamer responsive to an environmental cue, and (v) a sequence encoding an RNA that is responsive to an intracellular or environmental cue, and wherein the environmental cue is a nucleic acid, a protein, a metabolite, pH, and/or temperature.

Further provided herein is a nucleic acid construct that includes a synthetic TCRT that includes, in a 5' to 3' order: (a) a cis-regulator of translation and (b) an adapter TCRT, wherein the cis-regulator of translation and the adapter TCRT are operably linked so that the transcription of downstream sequences (i.e., sequences that are 3' of and operably linked to the synthetic TCRT) is regulated by the cis-regulator of translation, and wherein the adapter TCRT includes in a 5' to 3' order: a polynucleotide encoding the peptide tnaC; a stop codon; and a Rho utilization site (rut).

Also provided herein is a nucleic acid construct that includes (i) a synthetic TCRT that includes, in a 5' to 3' order, a first cis-regulator of translation and a first adapter TCRT, wherein the first cis-regulator of translation and the first adapter TCRT are operably linked; and (ii) a second synthetic TCRT that includes, in a 5' to 3' order, a second cis-regulator of translation and a second adapter TCRT, wherein the second cis-regulator of translation and the second adapter TCRT are operably linked; wherein, the first and second synthetic TCRTs are operably linked so that the transcription of downstream sequences (i.e., sequences that are 3' of and operably linked to the synthetic TCRTs) is regulated by the both the first and second cis-regulators of translation, and wherein the first and second cis-regulators of translation are orthogonal.

Also provided herein is a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, and wherein the cis-regulator of translation is selected from the group consisting of: RNA-IN, a RNA-IN variant, or a crRNA.

Also provided herein is a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, wherein the cis-regulator of translation is selected from the group including: RNA-IN, a RNA-IN variant, or a crRNA, and wherein the RNA-IN variant is selected from the group of: RNA-IN(3) (SEQ ID NO: 24), RNA-IN(4) (SEQ ID NO: 25), RNA-IN(9) (SEQ ID NO: 26), RNA-IN(20) (SEQ ID NO: 27), and RNA-IN(23) (SEQ ID NO: 28).

Also provided herein is a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, wherein the cis-regulator of translation is selected from the group consisting of: RNA-IN, a RNA-IN variant, and a crRNA, and wherein the crRNA is crR12 (SEQ ID NO: 36).

Also provided herein is a nucleic acid construct that includes a synthetic translation-coupled regulator of transcription that is described by the formula:

Also provided herein is a nucleic acid construct that includes a synthetic translation-coupled regulator of transcription that is described by the formula:

$$(AB)_x \quad \text{(Formula I)}$$

wherein:
(i) A is the cis-regulator of translation;
(ii) B is the adapter TCRT;
(iii) x is the number of repeated AB units;
(iv) x is any integer;
(v) each instance of A can be the same or different cis-regulator of translation as any previous instance of A; and
(vi) each instance of B can be the same or different adapter TCRT as any previous instance of B.

Also provided herein is a nucleic acid construct that includes a synthetic translation-coupled regulator of transcription that is described by the formula:

$$((AB)_x Q)_y \quad \text{(Formula II)}$$

wherein:
(i) A is the cis-regulator of translation;
(ii) B is the adapter TCRT;
(iii) x is the number of repeated AB units;
(iv) x is any integer;
(v) each instance of A can be the same or different cis-regulator of translation as any previous instance of A;
(vi) each instance of B can be the same or different adapter TCRT as any previous instance of B;
(vii) Q is a nucleic acid sequence of interest;
(viii) y is the number of repeated units of $(AB)_x Q$;
(ix) y is any integer; and
(x) each instance of Q can be the same or different nucleic acid sequence of interest as any previous instance of Q.

For both formulas I and II, x and y can each be any integer. In some embodiments, for both formulas I and II, x and y can each be any integer from 1-15 (e.g., 1-12, 1-10, 1-8, 1-7, 1-6, 1-5, 1-4, or 1-3). In some embodiments, Q is greater than 1 such that two or more genes (i.e., nucleic acid sequences of interest), each one controlled by a synthetic TCRT, are linked in series and thus form an operon. For both formulas I and II, as noted above, each instance of A can be the same or different cis-regulator of translation as any previous instance of A; e.g., the first instance of A can be a first cis-regulator of translation ($A_1$); the second instance of A can be $A_1$ or a second cis-regulator of translation ($A_2$); the third instance of A can be $A_1$, $A_2$, or a third cis-regulator of translation ($A_3$); etc. Similarly, for both formulas I and II, as noted above, each instance of B can be the same or different adapter TCRT as any previous instance of B; e.g., the first instance of B can be a first adapter TCRT ($B_1$); the second instance of B can be $B_1$ or a second adapter TCRT ($B_2$); the third instance of B can be $B_1$, $B_2$, or a third adapter TCRT ($B_3$); etc.

In another embodiment, provided herein is a recombinant prokaryotic cell comprising a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation.

Also provided herein is a recombinant prokaryotic cell comprising two or more nucleic acid constructs that each include a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation.

Also provided herein is a recombinant prokaryotic cell comprising two or more nucleic acid constructs that each include a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, and wherein at least two of the cis-regulators of translation are orthogonal.

Also provided herein is a recombinant prokaryotic cell comprising two or more nucleic acid constructs that each include a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, and wherein all of the cis-regulators of translation of the different synthetic TCRTs are orthogonal.

Also provided herein is a recombinant prokaryotic cell comprising a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, and wherein the cell further includes a polynucleotide that encodes a nucleic acid that binds to the cis-regulator of translation of the nucleic acid construct.

Also provided herein is a recombinant prokaryotic cell comprising a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably so that the transcription of downstream sequences (i.e., sequences that are 3' of and operably linked to the synthetic TCRT) is regulated by the cis-regulator of translation, and wherein the cell further includes a polynucleotide that encodes a taRNA. In some aspects, the taRNA is taR12 (SEQ ID NO: 29).

Also provided herein is a recombinant prokaryotic cell comprising a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, and wherein the cell further includes a polynucleotide that encodes RNA-OUT (SEQ ID NO: 30) or an RNA-OUT variant. In some aspects, the RNA-OUT variant is RNA-OUT(3) (SEQ ID NO: 31), RNA-OUT(4) (SEQ ID NO: 32), RNA-OUT(9) (SEQ ID NO: 33), RNA-OUT(20) (SEQ ID NO: 34), or RNA-OUT(23) (SEQ ID NO: 35).

Any of the recombinant prokaryotic cells provided herein that comprise a polynucleotide that encodes a nucleic acid that binds to the cis-regulator of translation of a nucleic acid construct can include two or more of the polynucleotides, and the two or more polynucleotides may encode two or more nucleic acids that bind to two or more cis-regulators of translation in a cell.

In another embodiment, provided herein is a method of controlling transcription of a nucleic acid sequence that includes, providing a cell that includes a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, wherein the nucleic acid construct further includes a nucleic acid sequence of interest, wherein the nucleic acid sequence is operably linked to the synthetic TCRT, which thereby regulates the expression of the nucleic acid sequence, and wherein the method further includes inducing the cis-regulator of translation.

In another aspect, provided herein is a method of controlling transcription of a nucleic acid sequence that includes, providing a cell that includes a nucleic acid construct that includes a synthetic translation-coupled regulator of transcription that includes, in a 5' to 3' order: a cis-regulator of translation and an adapter translation-coupled regulator of transcription, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, wherein the nucleic acid construct further includes a nucleic acid sequence of interest, wherein the nucleic acid sequence is operably linked to the synthetic TCRT which thereby regulates the expression of the nucleic acid sequence, wherein the method further includes inducing the cis-regulator of translation, and wherein inducing is performed by contacting the cells with a nucleic acid that binds to the cis-regulator of translation of the nucleic acid construct.

In another embodiment, provided herein is a kit that includes a plasmid that includes a synthetic translation-coupled regulator of transcription which includes in a 5' to 3' order: a cis-regulator of translation; an adapter translation-coupled regulator of transcription; and a multicloning site, wherein the cis-regulator of translation and the adapter translation-coupled regulator of transcription are operably linked so that the transcription of downstream sequences (i.e., sequences that are 3' of and operably linked to the synthetic TCRT) is regulated by the cis-regulator of translation, and wherein the kit further includes a plasmid encoding a nucleic acid that binds to the cis-regulator of translation of the nucleic acid construct.

The disclosure further includes polynucleotides having any of the sequences provided herein, fragments of sequences provided herein, and sequences which are complementary to any of the sequences provided herein. In addition, the disclosure includes polynucleotides that include RNA sequences that correspond to any of the DNA sequences disclosed herein, and polynucleotides that include DNA sequences that correspond to any of the RNA sequences disclosed herein, and fragments and complementary strands thereof.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a site-specific endoribonuclease" includes a plurality of such site-specific endoribonucleases and reference to "the target polyribonucleotide" includes reference to one or more target polyribonucleotides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

BRIEF DESCRIPTION OF THE DRAWINGS

FIGS. 1A-C. Strategy for converting translational control systems of interest (i.e., cis-regulators of translation) into synthetic TCRTs. FIG. 1A schematically depicts a cis-regulator of translation operably linked to an open reading frame (ORF); and a TCRT operably linked to an ORF. FIG. 1B depicts a cis-regulator of translation; and an adapter TCRT. FIG. 1C depicts an exemplary synthetic TCRT. Overlined nucleotides in bold correspond to the leader peptide's open reading frame (tnaC). SEQ ID NO: 15 is the sequence of nucleotides depicted in the Figure.

FIGS. 5A-D depict behavior of the converted taRNA/crRNA activator cis-regulator of translation into a synthetic TCRT (a synthetic activator TCRT FIGS. 6A and 6B depict performance of five mutually orthogonal antisense-mediated synthetic TCRTs achieved through conversion of the corresponding cis-regulator of translation (translational control systems).

FIGS. 9A-D depict SHAPE-informed structures of synthetic TCRTs achieved through conversion of the corresponding translational control systems.

DETAILED DESCRIPTION

Figure 2:
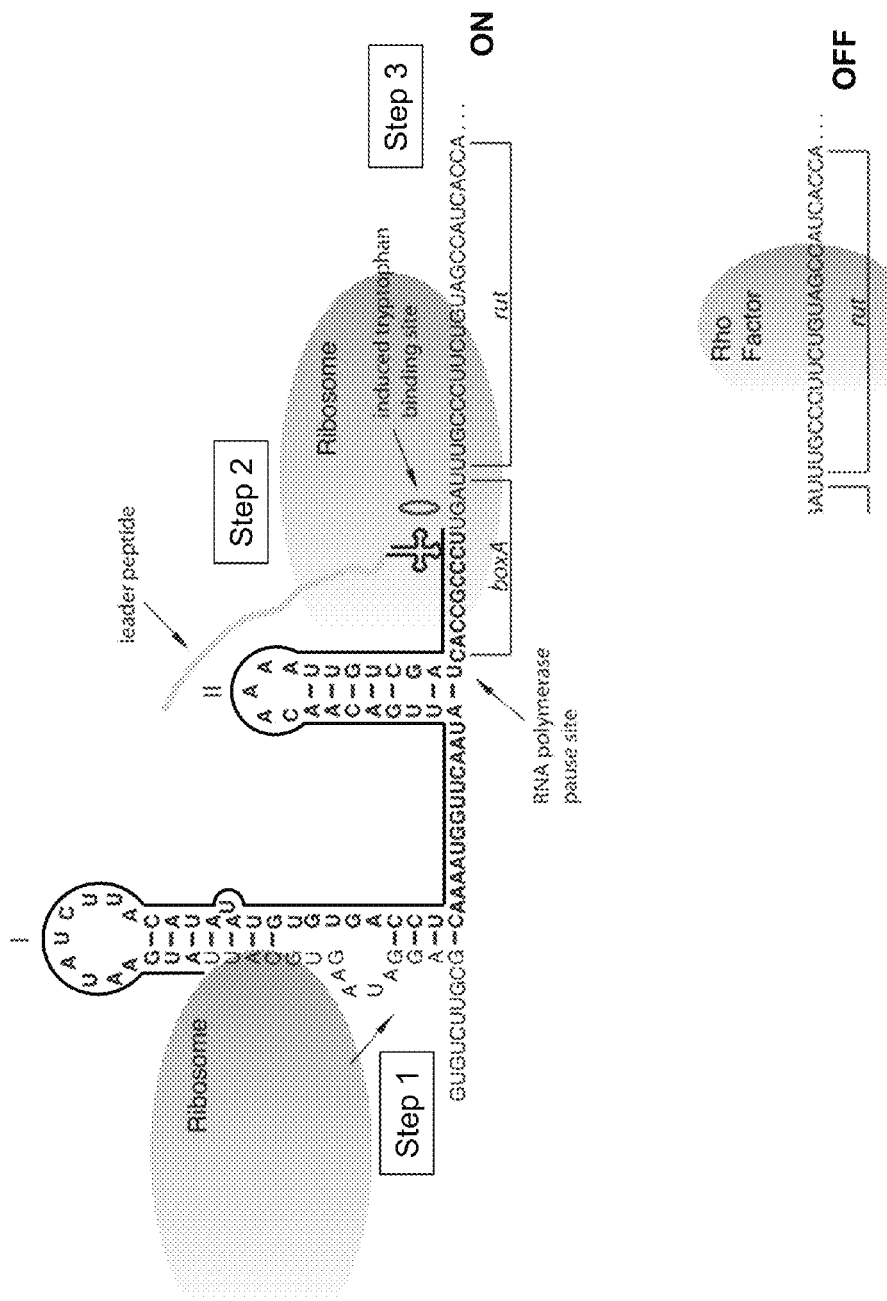
FIG. 2 depicts a mechanism for the tna leader-peptide element, a naturally occurring regulator of transcriptional elongation (i.e., translation-coupled regulator of transcription), from which an adapter (adapter TCRT) can be derived.

Provided herein are compositions and methods related to the conversion of cis-regulators of translation into synthetic translation-coupled regulators of transcription (synthetic TCRTs). In developing the synthetic TCRTs disclosed herein, the inventors were seeking to create a new class of transcriptional control elements that are easy to design, that operate on entire operons and that can be composed into logics and higher-order functions. The synthetic synthetic TCRTs disclosed herein meet all of these criteria. The inventors discovered that coupling (a) a cis-regulator of translation; with (b) an adapter translation-coupled regulator of transcription (adapter TCRT); produced (c) a synthetic TCRT with a surprisingly broad dynamic range that was greater than could have been predicted. Thus, synthetic TCRTs can be used to control the transcription of any nucleic acid sequence of interest and have a remarkable dynamic range in addition to the other advantages over existing control elements. Described in more detail below are cis-regulators of translation, adapter TCRTs, synthetic TCRTs, nucleic acid sequences of interest, nucleic acid constructs, cells comprising a nucleic acid construct, methods, and applications.

As used herein, the term "downstream" refers to sequences that are 3' of the sequence under discussion and the term "upstream" refers to sequences that are 5' of the sequence under discussion. For example, if sequence A is 5' of sequence B (i.e., sequence B is 3' of sequence A), then sequence A can be said to be upstream of sequence B. Likewise, sequence B can be said to be downstream of sequence A.

cis-Regulators of Translation

A subject synthetic translation-coupled regulator of transcription (synthetic TCRT) includes a cis-regulator of translation (FIG. 1). Such cis-regulators of translation can be cis-regulators of translation initiation or cis-regulators of translation elongation. "Cis-regulators of translation" or "translational control systems" as used herein include the portion of any RNA molecule that regulates or controls translation from the RNA molecule. "Cis-regulators of translation initiation" as used herein include the portion of any RNA molecule that regulates or controls translation initiation from the RNA molecule. "Cis-regulators of translation elongation" as used herein include the portion of any RNA molecule that regulates or controls translation elongation from the RNA molecule.

In some embodiments, the cis-regulator of translation is an "activator of translation" or an "activator cis-regulator of translation." An activator cis-regulator of translation controls translation such that translation of the RNA molecule increases in the presence of a regulatory input molecule (e.g., an antisense RNA molecule that hybridizes to a portion of the cis-regulator of translation, a small molecule that binds to the cis-regulator, etc.). When an activator cis-regulator of translation is converted into a synthetic TCRT, the synthetic TCRT can be referred to as a "synthetic activator TCRT". For an example of an activator cis-regulator of translation converted into a synthetic activator TCRT, see FIGS. 3c and 5.

In some embodiments, the cis-regulator of translation is an "attenuator of translation" or an "attenuator cis-regulator of translation." An attenuator cis-regulator of translation controls translation such that translation of the RNA molecule decreases in the presence of a regulatory input molecule (e.g., an antisense RNA molecule that hybridizes to a portion of the cis-regulator of translation, a small molecule that binds to the cis-regulator, etc.). When an attenuator cis-regulator of translation is converted into a synthetic TCRT, the synthetic TCRT can be referred to as a "synthetic attenuator TCRT". For an example of an attenuator cis-regulator of translation converted into a synthetic attenuator TCRT, see FIGS. 3b and 4.

Cis-regulators of translation included in the synthetic TCRTs provided herein may occur naturally, or they may not occur naturally. In some aspects, a cis-regulator of translation may be a modified version of a cis-regulator of translation that occurs naturally. In other aspects, a cis-regulator of translation may be designed de novo. Importantly, cis-regulators of translation are highly amenable to development and modification, due to importance of RNA structure for the function of many cis-regulators of translation. Because many factors affecting RNA structure are well-understood, cis-regulators of translation with desired characteristics may be designed and/or selected for by one of skill in the art. For example, the accessibility of a ribosome binding site in RNA may depend on whether or not the ribosome binding site is sequestered in an RNA stem-loop structure. The stability of various stem-loop structures may be calculated and/or predicted by one of skill in the art, due to the well-known binding properties between different nucleotides, and other factors. Accordingly, cis-regulators of translation wherein the ribosome binding site is sequestered in a stem-loop structure in certain conditions and not sequestered in a stem-loop structure in other conditions may be designed and/or prepared by one of skill in the art. Many different cis-regulators of translation are known in the art. See, e.g., Nahvi A et al., *Chem. Biol*, 9: 1043 (2002), Nou X and Kadner R J, *Proc. Natl. Acad. Sci.*, 97: 7190-7195 (2000), Winkler W C et al., *Proc. Natl. Acad. Sci.*, 99: 15908-15913 (2002), and Winkler W et al., *Nature*, 419: 952-956 (2002).

Commonly, cis-regulators of translation link cellular inputs to the accessibility of ribosome binding sites (RBSs) on the 5' UTR of a gene. Cis-regulators of translation function through multiple different mechanisms, including, without limitation, riboswitches that sense small molecules, antisense RNA repressors and activators, and RBSs that are responsive to proteins, nutrients, pH and/or temperature. As stated above, cis-regulators of translation may occur in nature, or they may be synthetic. Cis-regulators of translation may be located exclusively in the 5'-untranslated region (UTR) of a gene, or they may be located in both the 5'UTR of a gene, and the protein-coding region of a gene.

An input molecule that controls the "ON" or "OFF" state of a cis-regulator of translation is referred to herein as a regulatory input molecule. A "regulatory input molecule" can be any molecule that regulates a cis-regulator of translation. For example, suitable regulatory input molecules include, but are not limited to, small molecules (e.g., those that regulate riboswitches and aptamers as described below), sense or antisense RNA molecules (e.g., RNA-OUT, aptamer-RNA-OUT fusions, and the like), proteins, antibiotics, etc. Depending on the mechanism of regulation, a regulatory input molecule can be an activator that biases a cis-regulator of translation towards an "ON" state, or an attenuator that biases a cis-regulator of translation towards an "OFF" state. Suitable regulatory input molecules are described below in relation to the cis-regulators of translation that they control.

Riboswitches that Sense Small Molecules

In some aspects, a cis-regulator of translation includes a riboswitch. Riboswitches are RNA structures that are responsive to the presence or absence of a small molecule. In some riboswitches, the binding of a small molecule to the riboswitch increases the accessibility of an RBS to a ribosome (an "activator of translation"). In some riboswitches, the binding of a small molecule to the riboswitch decreases the accessibility of an RBS to a ribosome (an "attenuator of translation"). Riboswitches include an "aptamer domain" or simply an "aptamer", which is a region of RNA that binds to a small molecule with high specificity. Riboswitches also include additional RNA regions, through which the binding of a small molecule to the aptamer domain affects the activity of the RNA molecule (an "expression platform" region).

Riboswitches that respond to large variety of different small molecules are known, including, without limitation, riboswitches that respond to guanine (Mandal M, et al., *Cell*, 113: 577-586 (2003)), lysine (Sudarsan N, et al., *Genes Dev*, 17: 2688-2697 (2003)), adenosylcobalamin (AdoCbl) (Nou X and Kadner R J, *Proc. Natl. Acad. Sci.*, 97:7190-7195 (2000); Nahvi A et al., *Chem. Biol*, 9: 1043 (2002)), S-adenosylhomocysteine (SAH) (Wang J X et al., *Mol. Cell*, 29: 691-702 (2008)), flavin mononucleotide (FMN) (Winkler W C et al., *Proc. Natl. Acad. Sci.*, 99: 15908-15913 (2002)), glycine (Mandal M et al, *Science*, 306: 275-279 (2004)), cyclic di-GMP (Sudarsan N et al., *Science*, 321: 411-413 (2008)), thiamine pyrophosphate (TPP) (Winkler W et al., *Nature*, 419: 952-956 (2002)), adenine (Mandal M and Breaker R R, *Nat. Struct. Mol. Biol*, 11: 29-35 (2004)), magnesium (Cromie M H, et al., *Cell*, 125: 71-84 (2006)) and S-adenosylmethionine (SAM) (Winkler W C et al., *Nat. Struct. Biol*, 10: 701-707 (2003)). The foregoing list is illustrative of the ease with which new riboswitches may designed. Riboswitches that respond to additional small molecules of interest may be designed de novo. RNA aptamers that bind to small molecules of interest may be generated, for example, by the in vitro process Systematic Evolution of Ligands by Exponential enrichment (SELEX) (Tuerk C and Gold L, *Science*, 249: 505-510 (1990); Stoltenburg R et al., *Biomol. Eng*, 24: 381-403 (2007)). Synthetic riboswitches may also be isolated by a genetic screen (Desai S K and Gallivan J P, *J. Am Chem. Soc.*, 126: 13247-13254 (2004); Lynch S A et al., *Chem. Biol*, 14: 173-184 (2007)).

In some embodiments, fusions are made between a riboswitch aptamer and an RNA-OUT molecule (i.e., an aptamer-RNA-OUT fusion) such that the RNA-OUT molecule (described in more detail below) is under the control of the interaction between a small molecule and the aptamer that binds the small molecule (Qi et. al, *Nucleic Acids Res.* 2012 July; 40(12):5775-86. Epub 2012 Mar. 1) (FIG. 8). Such a fusion is suitable to control a subject synthetic TCRT. Functional aptamer-RNA-OUT fusions can be generated and exemplary fusions are known in the art (e.g., theo-P-IS10 ncRNA fusion (SEQ ID NO: 43); theo-P-pT181 ncRNA fusion (SEQ ID NO: 44); theo-SE-pT181WT ncRNA fusion (SEQ ID NO: 45); theo-SE-pT181MT ncRNA fusion (SEQ ID NO: 46); MS2-SE-pT181WT ncRNA fusion (SEQ ID NO: 47); MS2-SE-pT181MT ncRNA fusion (SEQ ID NO: 48); theo-SE-pT181 MT-1 (SEQ ID NO: 49); theo-SE-pT181 MT-2 (SEQ ID NO: 50); theo-SE-pT181 MT-3 (SEQ ID NO: 51); and the like).

Antisense RNA Repressors and Activators

In some cis-regulators of translation, the accessibility of an RBS to ribosomes is regulated by the presence or absence of an antisense RNA molecule. In some cis-regulators of translation, the accessibility of an RBS is increased upon the binding of an antisense RNA molecule to the cis-regulator of translation (an "activator of translation"). In some cis-regulators of translation, the accessibility of an RBS is decreased upon the binding of an antisense RNA molecule to the cis-regulator of translation (an "attenuator of translation").

One example of an RBS that is regulated by an antisense RNA molecule is the RBS in the IS10 translational control system (Simons R W and Kleckner N, *Cell*, 34: 683-691 (1983)). In this system, the RBS is part of a region of the cis-regulatory unit termed "RNA-IN" (SEQ ID NO: 37). In the absence of an antisense RNA (RNA-OUT), the RBS in the RNA-IN is accessible to ribosomes, which allows for the initiation of translation. Another part of the IS10 translation control system is a separate antisense RNA molecule termed "RNA-OUT" (SEQ ID NO: 30), which has the capacity to bind the RNA-IN region of the cis-regulatory unit. When RNA-OUT is present in the vicinity of RNA-IN in sufficient amounts, it binds to RNA-IN, and forms a duplex that sequesters the RBS in the RNA-IN, thereby inhibiting translation. Thus, the RNA-IN/RNA-OUT translational control system is an "attenuator of translation." For example, see FIGS. 3*b* and 4.

Examples of RBSs that are regulated by antisense RNA molecules are those systematically engineered translational riboregulators based on the IS 10 translational control system. This system uses sequence variants of RNA-IN (SEQ ID NOs: 24-28) and RNA-OUT (SEQ ID NOs: 31-35), and the 5 cognate RNA-IN/RNA-OUT pairs are mutually orthogonal. In other words, each RNA-OUT does not interact (or interacts only minimally) with its non-cognate RNA-IN partner such that cross-talk between the RNA-IN/RNA-OUT pairs is absent or minimal. Thus, each RNA-OUT interacts specifically with its cognate partner RNA-IN. Five exemplary orthogonal pairs are RNA-IN(3)(SEQ ID NO: 24) and RNA-OUT(3)(SEQ ID NO: 31), RNA-IN(4)(SEQ ID NO: 25) and RNA-OUT(4)(SEQ ID NO: 32), RNA-IN(9)(SEQ ID NO: 26) and RNA-OUT(9)(SEQ ID NO: 33), RNA-IN(20)(SEQ ID NO: 27) and RNA-OUT(20)(SEQ ID NO: 34), and RNA-IN(23)(SEQ ID NO: 28) and RNA-OUT(23)(SEQ ID NO: 35). Additional examples of suitable orthogonal families of RNA-IN/RNA-OUT cognate pairs include those listed in Table 1 (sequences are listed in Table 2). The five RNA-IN/RNA-OUT pairs just described (3, 4, 9, 20, and 23) correspond to the final row of cognate pairs in Table 1. In other words, RNA-IN/RNA-OUT pairs S04, S05, S31, S34, and S49 of the final row of Table 1 are equivalent to RNA-IN/RNA-OUT pairs 3, 4, 9, 20, and 23 jut described. Thus Table 1 illustrates a large number of orthogonal RNA-IN/RNA-OUT pairs that are suitable for use as a cis-regulator of translation of a subject synthetic TCRT. The corresponding sequences are listed in Table 2.

Table 1.

Orthogonal families are listed along with the family members. Given below are the RNA-IN (sense, S) numbers. The cognate partner RNA-OUT (antisense, A) has the same number. For example, S07 is the cognate partner of A07. All members of a given family are orthogonal relative to one another (i.e., they exhibit minimal crosstalk). For example, as shown in the table, in family 5 of size 2, the RNA-IN/RNA-OUT pair S32 is orthogonal to the RNA-IN/RNA-OUT pair S52. In family number 7 of size 4, S04, S05, S31, and S49 are all orthogonal to each other. Only the RNA-IN member of each pair is listed. Thus, S06 represents the pair of RNA-IN S06 and RNA-OUT A06, while S23 represents the pair of RNA-OUT S23 and RNA-IN A23. Therefore, because S06 is orthogonal to S23 (family 1 of size 2), RNA-OUT A06 binds to RNA-IN S06, but not to RNA-IN S23; and, RNA-OUT A23 binds to RNA-IN S23, but not to RNA-IN S06. Crosstalk is defined as greater than 80% repression of the cognate partner and less than 15% crosstalk with all non-cognate partners of the family. Sequences for all RNA-IN/RNA-OUT orthogonal pairs are listed in Table 2.

| Family # | Mutually orthogonal Family (Member size: 2) | |
|---|---|---|
| 1 | S06 | S23 |
| 2 | S05 | S31 |
| 3 | S31 | S49 |
| 4 | S03 | S05 |
| 5 | S32 | S52 |
| 6 | S04 | S06 |
| 7 | S05 | S34 |
| 8 | S04 | S49 |
| 9 | S05 | S49 |
| 10 | S01 | S52 |
| 11 | S03 | S04 |
| 12 | S01 | S34 |
| 13 | S04 | S05 |
| 14 | S49 | S52 |
| 15 | S06 | S49 |
| 16 | S06 | S34 |
| 17 | S03 | S27 |
| 18 | S04 | S32 |
| 19 | S03 | S31 |
| 20 | S32 | S49 |
| 21 | S23 | S34 |
| 22 | S04 | S34 |
| 23 | S04 | S31 |
| 24 | S27 | S52 |
| 25 | S05 | S32 |
| 26 | S31 | S34 |
| 27 | S34 | S49 |
| 28 | S05 | S52 |
| 29 | S03 | S32 |
| 30 | S06 | S52 |
| 31 | S01 | S23 |
| 32 | S23 | S49 |

| | Mutually orthogonal Family (Member size: 3) | | |
|---|---|---|---|
| 1 | S31 | S34 | S49 |
| 2 | S05 | S49 | S52 |
| 3 | S04 | S06 | S49 |
| 4 | S32 | S49 | S52 |
| 5 | S06 | S34 | S49 |
| 6 | S03 | S04 | S31 |
| 7 | S04 | S06 | S34 |

| Family # | | | | |
|---|---|---|---|---|
| 8 | S06 | S49 | S52 | |
| 9 | S23 | S34 | S49 | |
| 10 | S05 | S32 | S52 | |
| 11 | S03 | S04 | S05 | |
| 12 | S05 | S31 | S49 | |
| 13 | S04 | S31 | S49 | |
| 14 | S01 | S23 | S34 | |
| 15 | S04 | S32 | S49 | |
| 16 | S04 | S31 | S34 | |
| 17 | S03 | S04 | S32 | |
| 18 | S03 | S05 | S31 | |
| 19 | S04 | S05 | S49 | |
| 20 | S05 | S31 | S34 | |
| 21 | S06 | S23 | S34 | |
| 22 | S04 | S05 | S34 | |
| 23 | S03 | S05 | S32 | |
| 24 | S05 | S32 | S49 | |
| 25 | S04 | S05 | S31 | |
| 26 | S04 | S34 | S49 | |
| 27 | S05 | S34 | S49 | |
| 28 | S04 | S05 | S32 | |
| 29 | S06 | S23 | S49 | |
| Mutually orthogonal Family (Member size: 4) | | | | |
| 1 | S03 | S04 | S05 | S32 |
| 2 | S05 | S32 | S49 | S52 |
| 3 | S05 | S31 | S34 | S49 |
| 4 | S04 | S06 | S34 | S49 |
| 5 | S04 | S31 | S34 | S49 |
| 6 | S04 | S05 | S32 | S49 |
| 7 | S04 | S05 | S31 | S49 |
| 8 | S04 | S05 | S34 | S49 |
| 9 | S03 | S04 | S05 | S31 |
| 10 | S06 | S23 | S34 | S49 |
| 11 | S04 | S05 | S31 | S34 |
| Mutually orthogonal Family (Member size: 5) | | | | |
| 1 | S04 | S05 | S31 | S34 | S49 |

TABLE 2

RNA-IN RNA-OUT sequences of Table 1

| Name | Molecule Type | SEQ ID NO: | Sequence 5' to 3' |
|---|---|---|---|
| S01 | RNA-IN | 52 | GCGAAAAAUCAAUAAGGAGACAACAAGAUGUGCGAACUCGAU |
| S02 | RNA-IN | 53 | CCGAAAAAUCAAUAAGGAGACAACAAGAUGUGCGAACUCGAU |
| S03 | RNA-IN | 54 | GGGAAAAAUCAAUAAGGAGACAACAAGAUGUGCGAACUCGAU |
| S04 | RNA-IN | 24 | GCCAAAAAUCAAUAAGGAGACAACAAGAUGUGCGAACUCGAU |
| S05 | RNA-IN | 25 | GCGUAAAAUCAAUAAGGAGACAACAAGAUGUGCGAACUCGAU |
| S06 | RNA-IN | 55 | GCGAUAAAUCAAUAAGGAGACAACAAGAUGUGCGAACUCGAU |
| S07 | RNA-IN | 56 | CGGAAAAAUCAAUAAGGAGACAACAAGAUGUGCGAACUCGAU |
| S08 | RNA-IN | 57 | CCCAAAAAUCAAUAAGGAGACAACAAGAUGUGCGAACUCGAU |
| S09 | RNA-IN | 58 | CCGUAAAAUCAAUAAGGAGACAACAAGAUGUGCGAACUCGAU |
| S10 | RNA-IN | 59 | CCGAUAAAUCAAUAAGGAGACAACAAGAUGUGCGAACUCGAU |
| S11 | RNA-IN | 60 | GGCAAAAAUCAAUAAGGAGACAACAAGAUGUGCGAACUCGAU |
| S12 | RNA-IN | 61 | GGGUAAAAUCAAUAAGGAGACAACAAGAUGUGCGAACUCGAU |
| S13 | RNA-IN | 62 | GGGAUAAAUCAAUAAGGAGACAACAAGAUGUGCGAACUCGAU |
| S14 | RNA-IN | 63 | GCCUAAAAUCAAUAAGGAGACAACAAGAUGUGCGAACUCGAU |
| S15 | RNA-IN | 64 | GCCAUAAAUCAAUAAGGAGACAACAAGAUGUGCGAACUCGAU |

TABLE 2-continued

RNA-IN RNA-OUT sequences of Table 1

| Name | Molecule Type | SEQ ID NO: | Sequence 5' to 3' |
|---|---|---|---|
| S16 | RNA-IN | 65 | GCGUUAAAUCAAUAAGGAGACAACAAGAUGUGCGAACUCGAU |
| S17 | RNA-IN | 66 | CGCAAAAUCAAUAAGGAGACAACAAGAUGUGCGAACUCGAU |
| S18 | RNA-IN | 67 | CGGUAAAUCAAUAAGGAGACAACAAGAUGUGCGAACUCGAU |
| S19 | RNA-IN | 68 | CGGAUAAAUCAAUAAGGAGACAACAAGAUGUGCGAACUCGAU |
| S20 | RNA-IN | 69 | CCCUAAAAUCAAUAAGGAGACAACAAGAUGUGCGAACUCGAU |
| S21 | RNA-IN | 70 | CCCAUAAAUCAAUAAGGAGACAACAAGAUGUGCGAACUCGAU |
| S22 | RNA-IN | 71 | CCGUUAAAUCAAUAAGGAGACAACAAGAUGUGCGAACUCGAU |
| S23 | RNA-IN | 72 | GGCUAAAAUCAAUAAGGAGACAACAAGAUGUGCGAACUCGAU |
| S24 | RNA-IN | 73 | GGCAUAAAUCAAUAAGGAGACAACAAGAUGUGCGAACUCGAU |
| S25 | RNA-IN | 74 | GGGUUAAAUCAAUAAGGAGACAACAAGAUGUGCGAACUCGAU |
| S26 | RNA-IN | 75 | GCCUAAAAUCAAUAAGGAGACAACAAGAUGUGCGAACUCGAU |
| S27 | RNA-IN | 76 | CGCUAAAAUCAAUAAGGAGACAACAAGAUGUGCGAACUCGAU |
| S28 | RNA-IN | 77 | CGCAUAAAUCAAUAAGGAGACAACAAGAUGUGCGAACUCGAU |
| S29 | RNA-IN | 78 | CGGUUAAAUCAAUAAGGAGACAACAAGAUGUGCGAACUCGAU |
| S30 | RNA-IN | 79 | CCCUUAAAUCAAUAAGGAGACAACAAGAUGUGCGAACUCGAU |
| S31 | RNA-IN | 26 | GGCUUAAAUCAAUAAGGAGACAACAAGAUGUGCGAACUCGAU |
| S32 | RNA-IN | 80 | CGCUUAAAUCAAUAAGGAGACAACAAGAUGUGCGAACUCGAU |
| S33 | RNA-IN | 81 | CCGUAAAAAAUCAAUAAGGAGACAACAAGAUGUGCGAACUCGAU |
| S34 | RNA-IN | 27 | GGGUAAAAAAUCAAUAAGGAGACAACAAGAUGUGCGAACUCGAU |
| S35 | RNA-IN | 82 | GCCUAAAAAAUCAAUAAGGAGACAACAAGAUGUGCGAACUCGAU |
| S36 | RNA-IN | 83 | CGGUAAAAAAUCAAUAAGGAGACAACAAGAUGUGCGAACUCGAU |
| S37 | RNA-IN | 84 | CCCUAAAAAAUCAAUAAGGAGACAACAAGAUGUGCGAACUCGAU |
| S38 | RNA-IN | 85 | GGCUAAAAAAUCAAUAAGGAGACAACAAGAUGUGCGAACUCGAU |
| S39 | RNA-IN | 86 | CCGAUAAAAAUCAAUAAGGAGACAACAAGAUGUGCGAACUCGAU |

TABLE 2-continued

RNA-IN RNA-OUT sequences of Table 1

| Name | Molecule Type | SEQ ID NO: | Sequence 5' to 3' |
|---|---|---|---|
| S40 | RNA-IN | 87 | GGGAUAAAAAUCAAUAAGGAGACAACAAGAUGUGCGAACUCGAU |
| S41 | RNA-IN | 88 | GCCAUAAAAAUCAAUAAGGAGACAACAAGAUGUGCGAACUCGAU |
| S42 | RNA-IN | 89 | CGGAUAAAAAUCAAUAAGGAGACAACAAGAUGUGCGAACUCGAU |
| S43 | RNA-IN | 90 | CCCAUAAAAAUCAAUAAGGAGACAACAAGAUGUGCGAACUCGAU |
| S44 | RNA-IN | 91 | GGCAUAAAAAUCAAUAAGGAGACAACAAGAUGUGCGAACUCGAU |
| S45 | RNA-IN | 92 | CCGCGAAAAAUCAAUAAGGAGACAACAAGAUGUGCGAACUCGAU |
| S46 | RNA-IN | 93 | GGGCGAAAAAUCAAUAAGGAGACAACAAGAUGUGCGAACUCGAU |
| S47 | RNA-IN | 94 | GCCCGAAAAAUCAAUAAGGAGACAACAAGAUGUGCGAACUCGAU |
| S48 | RNA-IN | 95 | CGGCGAAAAAUCAAUAAGGAGACAACAAGAUGUGCGAACUCGAU |
| S49 | RNA-IN | 28 | CCCCGAAAAAUCAAUAAGGAGACAACAAGAUGUGCGAACUCGAU |
| S50 | RNA-IN | 96 | GGCCGAAAAAUCAAUAAGGAGACAACAAGAUGUGCGAACUCGAU |
| S51 | RNA-IN | 97 | CCGGCAAAAAUCAAUAAGGAGACAACAAGAUGUGCGAACUCGAU |
| S52 | RNA-IN | 98 | GGGGCAAAAAUCAAUAAGGAGACAACAAGAUGUGCGAACUCGAU |
| S53 | RNA-IN | 99 | GCCGCAAAAAUCAAUAAGGAGACAACAAGAUGUGCGAACUCGAU |
| S54 | RNA-IN | 100 | CGGGCAAAAAUCAAUAAGGAGACAACAAGAUGUGCGAACUCGAU |
| S55 | RNA-IN | 101 | CCCGCAAAAAUCAAUAAGGAGACAACAAGAUGUGCGAACUCGAU |
| S56 | RNA-IN | 102 | GGCGCAAAAAUCAAUAAGGAGACAACAAGAUGUGCGAACUCGAU |
| A01 | RNA-OUT | 103 | UCGCACAUCUUGUUGUCUGAUUAUUGAUUUUUCGCGAAACCAUUUGAUCAUAUGACAAGAUGUGUAUCCACCUUAACUUAAUGAUUUUUACCAAAAUCAUUAGGGGAUUCAUCAG |
| A02 | RNA-OUT | 104 | UCGCACAUCUUGUUGUCUGAUUAUUGAUUUUUCGGGAAACCAUUUGAUCAUAUGACAAGAUGUGUAUCCACCUUAACUUAAUGAUUUUUACCAAAAUCAUUAGGGGAUUCAUCAG |
| A03 | RNA-OUT | 105 | UCGCACAUCUUGUUGUCUGAUUAUUGAUUUUUCCGAAACCAUUUGAUCAUAUGACAAGAUGUGUAUCCACCUUAACUUAAUGAUUUUUACCAAAAUCAUUAGGGGAUUCAUCAG |
| A04 | RNA-OUT | 31 | UCGCACAUCUUGUUGUCUGAUUAUUGAUUUUUGGCGAAACCAUUUGAUCAUAUGACAAGAUGUGUAUCCACCUUAACUUAAUGAUUUUUACCAAAAUCAUUAGGGGAUUCAUCAG |
| A05 | RNA-OUT | 32 | UCGCACAUCUUGUUGUCUGAUUAUUGAUUUUUACGCGAAACCAUUUGAUCAUAUGACAAGAUGUGUAUCCACCUU |

TABLE 2-continued

RNA-IN RNA-OUT sequences of Table 1

| Name | Molecule Type | SEQ ID NO: | Sequence 5' to 3' |
|---|---|---|---|
| | | | AACUUAAUGAUUUUACCAAAAUCAUUAGGGGAUUC AUCAG |
| A06 | RNA-OUT | 106 | UCGCACAUCUUGUUGUCUGAUUAUUGAUUUAUCGCGA AACCAUUUGAUCAUAUGACAAGAUGUGUAUCCACCUU AACUUAAUGAUUUUACCAAAAUCAUUAGGGGAUUC AUCAG |
| A07 | RNA-OUT | 107 | UCGCACAUCUUGUUGUCUGAUUAUUGAUUUUUCCGGA AACCAUUUGAUCAUAUGACAAGAUGUGUAUCCACCUU AACUUAAUGAUUUUACCAAAAUCAUUAGGGGAUUC AUCAG |
| A08 | RNA-OUT | 108 | UCGCACAUCUUGUUGUCUGAUUAUUGAUUUUUGGGG AAACCAUUUGAUCAUAUGACAAGAUGUGUAUCCACCU UAACUUAAUGAUUUUACCAAAAUCAUUAGGGGAUU CAUCAG |
| A09 | RNA-OUT | 109 | UCGCACAUCUUGUUGUCUGAUUAUUGAUUUUACGGGA AACCAUUUGAUCAUAUGACAAGAUGUGUAUCCACCUU AACUUAAUGAUUUUACCAAAAUCAUUAGGGGAUUC AUCAG |
| A10 | RNA-OUT | 110 | UCGCACAUCUUGUUGUCUGAUUAUUGAUUUAUCGGGA AACCAUUUGAUCAUAUGACAAGAUGUGUAUCCACCUU AACUUAAUGAUUUUACCAAAAUCAUUAGGGGAUUC AUCAG |
| A11 | RNA-OUT | 111 | UCGCACAUCUUGUUGUCUGAUUAUUGAUUUUUGCCGA AACCAUUUGAUCAUAUGACAAGAUGUGUAUCCACCUU AACUUAAUGAUUUUACCAAAAUCAUUAGGGGAUUC AUCAG |
| A12 | RNA-OUT | 112 | UCGCACAUCUUGUUGUCUGAUUAUUGAUUUUACCGA AACCAUUUGAUCAUAUGACAAGAUGUGUAUCCACCUU AACUUAAUGAUUUUACCAAAAUCAUUAGGGGAUUC AUCAG |
| A13 | RNA-OUT | 113 | UCGCACAUCUUGUUGUCUGAUUAUUGAUUUAUCCCGA AACCAUUUGAUCAUAUGACAAGAUGUGUAUCCACCUU AACUUAAUGAUUUUACCAAAAUCAUUAGGGGAUUC AUCAG |
| A14 | RNA-OUT | 114 | UCGCACAUCUUGUUGUCUGAUUAUUGAUUUUAGGCGA AACCAUUUGAUCAUAUGACAAGAUGUGUAUCCACCUU AACUUAAUGAUUUUACCAAAAUCAUUAGGGGAUUC AUCAG |
| A15 | RNA-OUT | 115 | UCGCACAUCUUGUUGUCUGAUUAUUGAUUUAUGGCGA AACCAUUUGAUCAUAUGACAAGAUGUGUAUCCACCUU AACUUAAUGAUUUUACCAAAAUCAUUAGGGGAUUC AUCAG |
| A16 | RNA-OUT | 116 | UCGCACAUCUUGUUGUCUGAUUAUUGAUUUAACGCGA AACCAUUUGAUCAUAUGACAAGAUGUGUAUCCACCUU AACUUAAUGAUUUUACCAAAAUCAUUAGGGGAUUC AUCAG |
| A17 | RNA-OUT | 117 | UCGCACAUCUUGUUGUCUGAUUAUUGAUUUUUGCGGA AACCAUUUGAUCAUAUGACAAGAUGUGUAUCCACCUU AACUUAAUGAUUUUACCAAAAUCAUUAGGGGAUUC AUCAG |
| A18 | RNA-OUT | 118 | UCGCACAUCUUGUUGUCUGAUUAUUGAUUUUACCGGA AACCAUUUGAUCAUAUGACAAGAUGUGUAUCCACCUU AACUUAAUGAUUUUACCAAAAUCAUUAGGGGAUUC AUCAG |
| A19 | RNA-OUT | 119 | UCGCACAUCUUGUUGUCUGAUUAUUGAUUUAUCCGGA AACCAUUUGAUCAUAUGACAAGAUGUGUAUCCACCUU AACUUAAUGAUUUUACCAAAAUCAUUAGGGGAUUC AUCAG |

TABLE 2-continued

RNA-IN RNA-OUT sequences of Table 1

| Name | Molecule Type | SEQ ID NO: | Sequence 5' to 3' |
|---|---|---|---|
| A20 | RNA-OUT | 120 | UCGCACAUCUUGUUGUCUGAUUAUUGAUUUUAGGGG AAACCAUUUGAUCAUAUGACAAGAUGUGUAUCCACCU UAACUUAAUGAUUUUUACCAAAAUCAUUAGGGGAUU CAUCAG |
| A21 | RNA-OUT | 121 | UCGCACAUCUUGUUGUCUGAUUAUUGAUUUUAUGGGG AAACCAUUUGAUCAUAUGACAAGAUGUGUAUCCACCU UAACUUAAUGAUUUUUACCAAAAUCAUUAGGGGAUU CAUCAG |
| A22 | RNA-OUT | 122 | UCGCACAUCUUGUUGUCUGAUUAUUGAUUUAACGGGA AACCAUUUGAUCAUAUGACAAGAUGUGUAUCCACCUU AACUUAAUGAUUUUUACCAAAAUCAUUAGGGGAUUC AUCAG |
| A23 | RNA-OUT | 123 | UCGCACAUCUUGUUGUCUGAUUAUUGAUUUUAGCCGA AACCAUUUGAUCAUAUGACAAGAUGUGUAUCCACCUU AACUUAAUGAUUUUUACCAAAAUCAUUAGGGGAUUC AUCAG |
| A24 | RNA-OUT | 124 | UCGCACAUCUUGUUGUCUGAUUAUUGAUUUAUGCCGA AACCAUUUGAUCAUAUGACAAGAUGUGUAUCCACCUU AACUUAAUGAUUUUUACCAAAAUCAUUAGGGGAUUC AUCAG |
| A25 | RNA-OUT | 125 | UCGCACAUCUUGUUGUCUGAUUAUUGAUUUAACCCGA AACCAUUUGAUCAUAUGACAAGAUGUGUAUCCACCUU AACUUAAUGAUUUUUACCAAAAUCAUUAGGGGAUUC AUCAG |
| A26 | RNA-OUT | 126 | UCGCACAUCUUGUUGUCUGAUUAUUGAUUUAAGGCGA AACCAUUUGAUCAUAUGACAAGAUGUGUAUCCACCUU AACUUAAUGAUUUUUACCAAAAUCAUUAGGGGAUUC AUCAG |
| A27 | RNA-OUT | 127 | UCGCACAUCUUGUUGUCUGAUUAUUGAUUUUAGCGGA AACCAUUUGAUCAUAUGACAAGAUGUGUAUCCACCUU AACUUAAUGAUUUUUACCAAAAUCAUUAGGGGAUUC AUCAG |
| A28 | RNA-OUT | 128 | UCGCACAUCUUGUUGUCUGAUUAUUGAUUUAUGCGGA AACCAUUUGAUCAUAUGACAAGAUGUGUAUCCACCUU AACUUAAUGAUUUUUACCAAAAUCAUUAGGGGAUUC AUCAG |
| A29 | RNA-OUT | 129 | UCGCACAUCUUGUUGUCUGAUUAUUGAUUUAACCGGA AACCAUUUGAUCAUAUGACAAGAUGUGUAUCCACCUU AACUUAAUGAUUUUUACCAAAAUCAUUAGGGGAUUC AUCAG |
| A30 | RNA-OUT | 130 | UCGCACAUCUUGUUGUCUGAUUAUUGAUUUAAGGGG AAACCAUUUGAUCAUAUGACAAGAUGUGUAUCCACCU UAACUUAAUGAUUUUUACCAAAAUCAUUAGGGGAUU CAUCAG |
| A31 | RNA-OUT | 33 | UCGCACAUCUUGUUGUCUGAUUAUUGAUUUUAGCCGA AACCAUUUGAUCAUAUGACAAGAUGUGUAUCCACCUU AACUUAAUGAUUUUUACCAAAAUCAUUAGGGGAUUC AUCAG |
| A32 | RNA-OUT | 131 | UCGCACAUCUUGUUGUCUGAUUAUUGAUUUUAGCGGA AACCAUUUGAUCAUAUGACAAGAUGUGUAUCCACCUU AACUUAAUGAUUUUUACCAAAAUCAUUAGGGGAUUC AUCAG |
| A33 | RNA-OUT | 132 | UCGCACAUCUUGUUGUCUGAUUAUUGAUUUUUACGG GAAACCAUUUGAUCAUAUGACAAGAUGUGUAUCCACC UUAACUUAAUGAUUUUUACCAAAAUCAUUAGGGGAU UCAUCAG |
| A34 | RNA-OUT | 34 | UCGCACAUCUUGUUGUCUGAUUAUUGAUUUUUACCC GAAACCAUUUGAUCAUAUGACAAGAUGUGUAUCCACC |

TABLE 2-continued

RNA-IN RNA-OUT sequences of Table 1

| Name | Molecule Type | SEQ ID NO: | Sequence 5' to 3' |
|------|---------------|------------|-------------------|
|      |               |            | UUAACUUAAUGAUUUUUACCAAAAUCAUUAGGGGAU UCAUCAG |
| A35  | RNA-OUT       | 133        | UCGCACAUCUUGUUGUCUGAUUAUUGAUUUUUAGGC GAAACCAUUUGAUCAUAUGACAAGAUGUGUAUCCACC UUAACUUAAUGAUUUUUACCAAAAUCAUUAGGGGAU UCAUCAG |
| A36  | RNA-OUT       | 134        | UCGCACAUCUUGUUGUCUGAUUAUUGAUUUUUACCG GAAACCAUUUGAUCAUAUGACAAGAUGUGUAUCCACC UUAACUUAAUGAUUUUUACCAAAAUCAUUAGGGGAU UCAUCAG |
| A37  | RNA-OUT       | 135        | UCGCACAUCUUGUUGUCUGAUUAUUGAUUUUUAGG GGAAACCAUUUGAUCAUAUGACAAGAUGUGUAUCCAC CUUAACUUAAUGAUUUUUACCAAAAUCAUUAGGGGA UUCAUCAG |
| A38  | RNA-OUT       | 136        | UCGCACAUCUUGUUGUCUGAUUAUUGAUUUUUAGCC GAAACCAUUUGAUCAUAUGACAAGAUGUGUAUCCACC UUAACUUAAUGAUUUUUACCAAAAUCAUUAGGGGAU UCAUCAG |
| A39  | RNA-OUT       | 137        | UCGCACAUCUUGUUGUCUGAUUAUUGAUUUUUAUCGG GAAACCAUUUGAUCAUAUGACAAGAUGUGUAUCCACC UUAACUUAAUGAUUUUUACCAAAAUCAUUAGGGGAU UCAUCAG |
| A40  | RNA-OUT       | 138        | UCGCACAUCUUGUUGUCUGAUUAUUGAUUUUUAUCCC GAAACCAUUUGAUCAUAUGACAAGAUGUGUAUCCACC UUAACUUAAUGAUUUUUACCAAAAUCAUUAGGGGAU UCAUCAG |
| A41  | RNA-OUT       | 139        | UCGCACAUCUUGUUGUCUGAUUAUUGAUUUUUAUGGC GAAACCAUUUGAUCAUAUGACAAGAUGUGUAUCCACC UUAACUUAAUGAUUUUUACCAAAAUCAUUAGGGGAU UCAUCAG |
| A42  | RNA-OUT       | 140        | UCGCACAUCUUGUUGUCUGAUUAUUGAUUUUUAUCCG GAAACCAUUUGAUCAUAUGACAAGAUGUGUAUCCACC UUAACUUAAUGAUUUUUACCAAAAUCAUUAGGGGAU UCAUCAG |
| A43  | RNA-OUT       | 141        | UCGCACAUCUUGUUGUCUGAUUAUUGAUUUUUAUGG GGAAACCAUUUGAUCAUAUGACAAGAUGUGUAUCCAC CUUAACUUAAUGAUUUUUACCAAAAUCAUUAGGGGA UUCAUCAG |
| A44  | RNA-OUT       | 142        | UCGCACAUCUUGUUGUCUGAUUAUUGAUUUUUAUGCC GAAACCAUUUGAUCAUAUGACAAGAUGUGUAUCCACC UUAACUUAAUGAUUUUUACCAAAAUCAUUAGGGGAU UCAUCAG |
| A45  | RNA-OUT       | 143        | UCGCACAUCUUGUUGUCUGAUUAUUGAUUUUUCGCGG GAAACCAUUUGAUCAUAUGACAAGAUGUGUAUCCACC UUAACUUAAUGAUUUUUACCAAAAUCAUUAGGGGAU UCAUCAG |
| A46  | RNA-OUT       | 144        | UCGCACAUCUUGUUGUCUGAUUAUUGAUUUUUCGCCC GAAACCAUUUGAUCAUAUGACAAGAUGUGUAUCCACC UUAACUUAAUGAUUUUUACCAAAAUCAUUAGGGGAU UCAUCAG |
| A47  | RNA-OUT       | 145        | UCGCACAUCUUGUUGUCUGAUUAUUGAUUUUUCGGGC GAAACCAUUUGAUCAUAUGACAAGAUGUGUAUCCACC UUAACUUAAUGAUUUUUACCAAAAUCAUUAGGGGAU UCAUCAG |
| A48  | RNA-OUT       | 146        | UCGCACAUCUUGUUGUCUGAUUAUUGAUUUUUCGCCG GAAACCAUUUGAUCAUAUGACAAGAUGUGUAUCCACC UUAACUUAAUGAUUUUUACCAAAAUCAUUAGGGGAU UCAUCAG |

TABLE 2-continued

RNA-IN RNA-OUT sequences of Table 1

| Name | Molecule Type | SEQ ID NO: | Sequence 5' to 3' |
|---|---|---|---|
| A49 | RNA-OUT | 35 | UCGCACAUCUUGUUGUCUGAUUAUUGAUUUUUCGGGG GAAACCAUUUGAUCAUAUGACAAGAUGUGUAUCCACC UUAACUUAAUGAUUUUUACCAAAAUCAUUAGGGGAU UCAUCAG |
| A50 | RNA-OUT | 147 | UCGCACAUCUUGUUGUCUGAUUAUUGAUUUUUCGGCC GAAACCAUUUGAUCAUAUGACAAGAUGUGUAUCCACC UUAACUUAAUGAUUUUUACCAAAAUCAUUAGGGGAU UCAUCAG |
| A51 | RNA-OUT | 148 | UCGCACAUCUUGUUGUCUGAUUAUUGAUUUUUGCCGG GAAACCAUUUGAUCAUAUGACAAGAUGUGUAUCCACC UUAACUUAAUGAUUUUUACCAAAAUCAUUAGGGGAU UCAUCAG |
| A52 | RNA-OUT | 149 | UCGCACAUCUUGUUGUCUGAUUAUUGAUUUUUGCCCC GAAACCAUUUGAUCAUAUGACAAGAUGUGUAUCCACC UUAACUUAAUGAUUUUUACCAAAAUCAUUAGGGGAU UCAUCAG |
| A53 | RNA-OUT | 150 | UCGCACAUCUUGUUGUCUGAUUAUUGAUUUUUGCGGC GAAACCAUUUGAUCAUAUGACAAGAUGUGUAUCCACC UUAACUUAAUGAUUUUUACCAAAAUCAUUAGGGGAU UCAUCAG |
| A54 | RNA-OUT | 151 | UCGCACAUCUUGUUGUCUGAUUAUUGAUUUUUGCCCG GAAACCAUUUGAUCAUAUGACAAGAUGUGUAUCCACC UUAACUUAAUGAUUUUUACCAAAAUCAUUAGGGGAU UCAUCAG |
| A55 | RNA-OUT | 152 | UCGCACAUCUUGUUGUCUGAUUAUUGAUUUUUGCGGG GAAACCAUUUGAUCAUAUGACAAGAUGUGUAUCCACC UUAACUUAAUGAUUUUUACCAAAAUCAUUAGGGGAU UCAUCAG |
| A56 | RNA-OUT | 153 | UCGCACAUCUUGUUGUCUGAUUAUUGAUUUUUGCGCC GAAACCAUUUGAUCAUAUGACAAGAUGUGUAUCCACC UUAACUUAAUGAUUUUUACCAAAAUCAUUAGGGGAU UCAUCAG |

Another example of an RBS that is regulated by an antisense RNA is the RBS in the taRNA/crRNA translational control system (Isaacs F J, *Nat. Biotech.*, 22: 841-847, (2004)). In this system, the RBS is part of a region of a cis-regulatory unit termed "crRNA". In the absence of an antisense RNA, the RBS in the crRNA is not accessible to ribosomes, as it is sequestered as part of a stem-loop structure. Another part of the taRNA/crRNA translational control system is a separate antisense RNA molecule termed "taRNA", which has the capacity to bind to the stem-loop structure near the RBS (but not directly to the RBS). When taRNA is in the vicinity of crRNA in sufficient amounts, it binds to a portion of crRNA that does not include the RBS, and thereby releases the RBS from the stem-loop structure in crRNA. Once the RBS is no longer sequestered, ribosomes are able to bind to the RBS. Thus, the taRNA/crRNA translational control system is an "activator of translation." For example, see FIGS. 3c and 5. One example of a specifically engineered crRNA is crR12 (SEQ ID NO: 36). The corresponding taRNA is taR12 (SEQ ID NO: 29).

Yet another example of an RBS that is regulated by antisense RNA is the RNA upstream of the *E. coli* RpoS gene, which is regulated by both antisense RNA and temperature (Repolia F and Gottesman S, *J Bacteriol*, 183: 4012-4023, (2001); Repolia et al., *Mol Microbiol*, 48: 855-861, (2003)). At certain higher temperatures (e.g. 42° C.), the RNA adopts a conformation in which the RBS is sequestered in a stem loop structure. In contrast, at lower temperatures (e.g. 25° C.), the RBS is not sequestered, due to the binding of a small noncoding RNA, DsrA, to a region of the RNA near the RBS, which disrupts the stem loop structure and the sequestration of the RBS.

RBSs that are Responsive to Temperature

In some cis-regulators of translation, the accessibility of an RBS to ribosomes is regulated by temperature. In some cis-regulators of translation, an RBS is not accessible at a lower temperature, and it becomes accessible as the temperature is increased. If an RBS is not accessible at a lower temperature and it becomes accessible at a higher temperature, commonly, the RBS is part of an RNA stem-loop structure at a lower temperature, and it becomes singlestranded and accessible to ribosomes at higher temperatures. In other cis-regulators of translation, an RBS is accessible at a lower temperatures, and it becomes inaccessible at certain higher temperatures. If an RBS is not accessible at certain higher temperatures and it becomes accessible at lower temperature, commonly, the RBS is part of a stem-loop structure at a certain higher temperatures, and at lower temperatures, the RBS is not sequestered in a stem-loop structure. In some aspects, if an RBS is not accessible at certain higher temperatures and it becomes accessible at lower temperatures, the RBS may be part of a stem-loop structure at a higher temperature, and at lower temperatures, a trans-acting oligonucleotide binds to a portion of the RNA and disrupts the RNA stem loop structure including the RBS, thereby causing the RBS to become accessible at lower temperatures.

One example of an RBS that is regulated by temperature is the RNA upstream of the λ cIII gene (Altuvia S, et al. J Mol Biol, 210: 265-280 (1989); Altuvia S, et al., J Mol Biol, 218: 723-733 (1991)). At certain higher temperatures (e.g. 45° C.), the RNA adopts a conformation in which the start codon and part of the RBS is sequestered in a stem-loop structure, thereby preventing binding of the ribosome to the sequence. In contrast, at certain lower temperatures (e.g. 37° C.), the RNA adopts a conformation in which the start codon and RBS are not sequestered, thereby permitting binding of the ribosome to the sequence and initiation of translation.

Another example of an RBS that is regulated by temperature is the RNA upstream of the *E. coli* rpoH gene (Morita M, et al., *J. Bacteriol*, 181: 401-410 (1999)). At higher temperatures (e.g. 42° C.) the RNA adopts a conformation in which the RBS is exposed, thereby permitting binding of the ribosome to the sequence and initiation of translation. In contrast, at lower temperatures (e.g. 30° C.), the RNA adopts a conformation in which the RBS is sequestered in a stem-loop structure, thereby preventing binding of the ribosome to the sequence.

Another example of an RBS that is regulated by temperature is the RNA upstream of various *Bradyrhizobium japonicum* small heat-shock genes (see, e.g., Zuker M, *Nucleic Acids Res*, 31: 3406-3415 (2003)). At higher temperatures (e.g. 42° C.) the RNA adopts a conformation in which the RBS is exposed, thereby permitting binding of the ribosome to the sequence and initiation of translation. In contrast, at lower temperatures (e.g. 30° C.), the RNA adopts a conformation in which the RBS is sequestered in an RNA stem-loop structure, thereby preventing binding of the ribosome to the sequence.

Yet another example of an RBS that is regulated by temperature is the RNA upstream of the *E. coli* RpoS gene (Repolia F and Gottesman S, *J Bacteriol*, 183: 4012-4023, (2001); Repolia et al., *Mol Microbiol*, 48: 855-861, (2003)). At higher temperatures (e.g. 42° C.), the RNA adopts a conformation in which the RBS is sequestered in a stem-loop structure. In contrast, at lower temperatures (e.g. 25° C.), the RBS is not sequestered, due to the binding of a small noncoding RNA, DsrA, to a region of the RNA near the RBS, which disrupts the sequestration of the RBS.

RBSs that are Responsive to Proteins

In some cis-regulators of translation, translation is regulated by the concentration of a protein. In some aspects, a cis-regulator of translation that is regulated by the concentration of a protein may be regulated by the concentration of a protein encoded by the mRNA which is controlled by that cis-regulator of translation. In other words, initiation of translation may be regulated at some cis-regulators of translation by the concentration of the protein whose translation is regulated by that same cis-regulator of translation (Romby P and Springer M, *Trends Genet* 19: 155-161 (2003)).

In some cis-regulators of translation, translation is regulated by a protein that is responsive to levels of a product that is synthesized by genes regulated by the cis-regulator of translation. In one example, the accessibility of the RBS for genes related to tryptophan biosynthesis in *Bacillus subtilis* is regulated by the protein trp RNA-binding attenuation protein (TRAP)(Babitzke, P, *Curr Opin Microbiol* 7: 132-139, (2004)). When TRAP is complexed with tryptophan, it binds to the RNA upstream of the regulated genes, and it reduces the accessibility of the RBS either through direct occlusion or through causing a rearrangement of the RNA that sequesters the RBS.

RBSs that are Responsive to Antibiotics

In some cis-regulators of translation, the accessibility of an RBS to ribosomes is regulated by the concentration of an antibiotic. In such regulators, typically, the presence of the antibiotic increases the accessibility of the RBS, and thus increases the translation of the downstream regulated gene. Examples of this mechanism occur with, for example, genes related to chloramphenicol and erythromycin resistance (Lovett, P. S. and Rogers, E. J., *Microbiol. Rev.* 60, 366-385 (1996); Weisblum, B, *Antimicrob. Agents Chemother.*, 39, 797-805 (1995)). In these mechanisms, a gene encoding an antibiotic resistance-related protein is preceded by a short leader peptide, and the RBS for the gene encoding the antibiotic resistance-related protein is sequestered. If the antibiotic is present, during translation of the leader peptide, the antibiotic interacts with the ribosome and the nascent leader peptide, and induces stalling of the ribosome. This stalling of the ribosome causes reorganization of the RNA, and increases accessibility of the RBS of the gene encoding an antibiotic-resistance related-protein.

Constructs Having a Tuned or De Novo Designed RBS

In some aspects, RBS-based interactions can be tuned or designed de novo using predictive thermodynamic models (Salis H M, et al., *Nat. Biotech.*, 27: 946-950 (2009)). Many factors affecting RNA structure are well-understood in the art, and cis-regulators of translation with desired characteristics may be designed and/or selected for by one of skill in the art. For example, synthetic RBSs with desired translation levels may be generated (Salis H M, et al., *Nat. Biotech.*, 27: 946-950 (2009)). As another example, the accessibility of a ribosome binding site in RNA may depend on whether or not the RBS is sequestered in an RNA stem-loop structure. The stability and sensitivity of different stem-loop structures may be calculated and/or predicted by one of skill in the art, due to the well-known thermodynamic binding properties between different nucleotides and other factors. Accordingly, cis-regulators of translation wherein the ribosome binding site is sequestered in a stem-loop structure under certain conditions and not sequestered in a stem-loop structure in other conditions may be designed and/or prepared by one of skill in the art. The term "tuned ribosome binding site" refer to a ribosome binding site with a specific engineered or selected strength.

Adapter Translation-Coupled Regulators of Transcription

A subject synthetic translation-coupled regulator of transcription (synthetic TCRT) includes an adapter translation-coupled regulator of transcription (adapter TCRT). In the synthetic TCRTs of the present disclosure, cis-regulators of translation are operably linked to (and positioned 5' of) adapter TCRTs. (FIG. 1). A subject adapter TCRT is an isolated functional translation-coupled regulator of transcription (TCRT). As used herein, a "translation-coupled regulator of transcription" or "TCRT" or "translationally-coupled transcription continuation element" is a nucleic acid sequence (e.g., mRNA) wherein the translation of a peptide from the nucleic acid sequence affects the transcription of nucleotides downstream from the nucleic acid sequence. In other words, the translation of a TCRT influences the transcription of linked downstream nucleotides. Thus, an isolated TCRT can function as an adapter for a cis-regulator of translation because it converts the cis-regulator of translation into a regulator of transcription. Because an "adapter TCRT" is an isolated functional TCRT, an adapter TCRT can simply be referred to as a "TCRT." An adapter TCRT (i.e., TCRT) can be linked to any desired nucleotide sequence (e.g., a cis-regulator of translation, a nucleotide sequence of interest, etc.) (FIG. 1).

Translation-coupled regulators of transcription (and therefore adapter TCRTs) may occur naturally, or they may not occur naturally. In some aspects, an adapter translation-coupled regulator of transcription may be a modified version of a translation-coupled regulator of transcription that occurs naturally. In other aspects, an adapter translation-coupled regulator of transcription may be designed de novo. Importantly, translation-coupled regulators of transcription (and adapter TCRTs) are highly amenable to development and modification, due to importance of RNA structure for the function of many translation-coupled regulators of transcription. Because many factors affecting RNA structure are well-understood, translation-coupled regulators of transcription (and adapter TCRTs) with desired characteristics may be designed and/or selected for by one of skill in the art. Thus, all TCRTs are suitable.

In some aspects, in a translation-coupled regulator of transcription, the completion of translation of a peptide may be coupled to the continuation of transcription of a downstream nucleotide sequence. In other aspects, in a translation-coupled regulator of transcription, the completion of translation of a peptide may be coupled to the termination or inhibition of transcription of a downstream nucleotide sequence.

One example of a suitable translation-coupled regulator of transcription (TCRT) (i.e., a regulator of transcriptional elongation), from which an adapter TCRT can be derived and a synthetic TCRT constructed, is a portion of the tna operon of *Escherichia coli*. This portion of the tna operon includes, from 5' to 3', the coding region for a short leader peptide (tnaC), a Rho factor-binding site, and a stretch of RNA required for Rho factor-mediated transcriptional termination. The controlled genes are further to the 3' end of the stretch of RNA required for Rho factor-mediated transcriptional termination. In the tna regulatory element's mechanism, translation of the embedded leader peptide, tnaC, is kinetically coordinated with transcription such that induced ribosomal stalling during translation allows transcriptional continuation by RNA polymerase into the regulated genes (FIG. 2). Specifically, full translation of tnaC during production of the nascent mRNA transcript results in ribosomal stalling, when tryptophan is present, over a Rho factor-binding site adjacent to the stop codon of tnaC; this block in turn prevents Rho factor-mediated termination of continued transcription. Therefore, full translation of tnaC results in transcriptional activation of downstream genes. On the other hand, if translation of tnaC halts prematurely or fails to initiate, then the ribosome cannot reach and block the Rho factor-binding site in the nascent mRNA; as a result, Rho factor-mediated transcriptional termination occurs before the controlled genes can be synthesized by RNA polymerase. In summary, successful translation of tnaC in the tna leader-peptide element results in successful transcription of the controlled genes, whereas unsuccessful tnaC translation results in unsuccessful transcription of the controlled genes.

Additional suitable examples of suitable translation-coupled regulators of transcription, from which an adapter TCRT can be derived and a synthetic TCRT constructed, include the relevant functional portions (which can readily be determine by one of ordinary skill in the art) of the trp, his, leu, ilv, thr, pheST, pyrBI, pyrE, and pheA operons of multiple species of bacteria (See, e.g., Vitreschak A. G. et al., *FEMS Microbiol. Lett.*, 234: 357-370, (2004); Turnbough et al, *Microbiol Mol Biol Rev.* 2008 June; 72(2):266-300; and Landick R, "Transcriptional attenuation. In: *Escherichia coli* and *Salmonella*. Cellular and Molecular Biology, American Society for Microbiology Press: 263-1286 (1996)). In these translation-coupled regulators of transcription, successful translation of a leader peptide results in termination of transcription, and lack of transcription of the controlled genes. In these examples, there is an RNA leader sequence which can adopt either an antiterminator formation (which causes continuation of transcription) or a terminator formation (which causes termination of transcription). Depending on the rate of translation of a leader polypeptide from this leader sequence (and the rate of movement of the ribosome), either the antiterminator or the terminator RNA structure forms. If the rate of translation of the leader peptide is slow (due to the low availability of one or more amino acids), the position of the ribosome causes the development of the antiterminator structure, and subsequent continuation of transcription. Similarly, if the rate of translation of the leader peptide is high (due to the high availability of amino acids), the position of the ribosome causes the development of the terminator structure, and subsequent termination of transcription.

Translation elongation of a leader peptide may also be regulated through the use of unnatural amino acids. See, e.g., Liu C et al. *Nature Biotech.*, 29(2), 164-168 (2011). As used herein, an "unnatural amino acid" is an amino acid that has been artificially added to the genetic code. In this approach to regulation of translation of a leader peptide, a blank codon (e.g. a codon that does not encode a natural proteinogenic amino acid) is introduced into the genetic code of a polypeptide-encoding sequence. In addition, tRNAs that can decode the blank codons and corresponding aminoacyl-tRNA synthetases that can charge the tRNAs with an unnatural amino acid of interest are provided. In this system, continuation of translation can be controlled by providing or not providing the relevant unnatural amino acid to the translation environment (e.g. a cell or an in vitro translation system). If tRNAs charged with an unnatural amino acid necessary for continuation of translation of a polypeptide are not present, translation of the polypeptide will slow down or cease. This method can be incorporated with any translation-coupled regulator of transcription, in order to further regulate translation of a leader peptide, and the subsequent effects of translation of the leader peptide on transcription of a nucleic acid sequence of interest.

Synthetic Translation-Coupled Regulator of Transcription

Provided herein are synthetic translation-coupled regulators of transcription (synthetic TCRTs). A "synthetic translation-coupled regulator of transcription" or "synthetic TCRT" or "synthetic transcription control element" provided herein includes at least two components, in a 5' to 3' order: (a) a cis-regulator of translation, and (b) a translation-coupled regulator of transcription (adapter TCRT) (FIG. 1). In the synthetic TCRT, the cis-regulator of translation and the adapter TCRT are operably linked so that the transcription of downstream sequences (i.e., sequences that are 3' of and operably linked to the synthetic TCRT) is regulated by the cis-regulator of translation.

Synthetic TCRTs provided herein may include various different cis-regulators of translation and various different adapter TCRTs. In some embodiments, the adapter translation-coupled regulators of transcription of the synthetic TCRTs provided herein include a leader peptide-coding sequence, and provide a structure and/or support a mechanism whereby the translation of the leader peptide is coupled to continuation of transcription of one or more nucleic acid sequences downstream of the leader peptide-coding sequence.

Within the synthetic TCRT, the leader peptide-coding sequence of the adapter TCRT may have no nucleotides in common with the cis-regulator of translation. Alternatively, the leader-peptide coding sequence may have nucleotides in common with the cis-regulator of translation. For example, if the cis-regulator of translation is a region that is regulated through the binding of an antisense nucleic acid to that that region, the nucleotides to which the antisense nucleic acid binds may be entirely different from nucleotides that encode the leader-peptide. Alternatively, the antisense nucleic acid may bind to nucleotides that encode a portion or all of the leader peptide. In another example, if the cis-regulator of translation is a region that is regulated through the binding of a small molecule to that that region, the nucleotides to which the small molecule binds may be entirely different from nucleotides that encode the leader-peptide. Alternatively, the small molecule may bind to nucleotides that encode a portion or all of the leader peptide.

As described above, depending on whether the included cis-regulator of translation is an attenuator of translation or an activator of translation, a synthetic TCRT can be a synthetic attenuator TCRT or a synthetic activator TCRT, respectively.

Also provided herein is a nucleic acid construct that includes a synthetic translation-coupled regulator of transcription that is described by the formula:

$$(AB)_x \quad \text{(Formula I)}$$

wherein:
(i) A is the cis-regulator of translation;
(ii) B is the adapter TCRT;
(iii) x is the number of repeated AB units;
(iv) x is any integer;
(v) each instance of A can be the same or different cis-regulator of translation as any previous instance of A; and
(vi) each instance of B can be the same or different adapter TCRT as any previous instance of B.

Also provided herein is a nucleic acid construct that includes a synthetic translation-coupled regulator of transcription that is described by the formula:

$$((AB)_xQ)_y \quad \text{(Formula II)}$$

wherein:
(i) A is the cis-regulator of translation;
(ii) B is the adapter TCRT;
(iii) x is the number of repeated AB units;
(iv) x is any integer;
(v) each instance of A can be the same or different cis-regulator of translation as any previous instance of A;
(vi) each instance of B can be the same or different adapter TCRT as any previous instance of B;
(vii) Q is a nucleic acid sequence of interest;
(viii) y is the number of repeated units of $(AB)_xQ$;
(ix) y is any integer; and
(x) each instance of Q can be the same or different nucleic acid sequence of interest as any previous instance of Q.

For both formulas I and II, x and y can each be any integer. In some embodiments, for both formulas I and II, x and y can each be any integer from 1-15 (e.g., 1-12, 1-10, 1-8, 1-7, 1-6, 1-5, 1-4, or 1-3). In some embodiments, Q is greater than 1 such that two or more genes (i.e., nucleic acid sequences of interest), each one controlled by a synthetic TCRT, are linked in series and thus form an operon.

Nucleic Acid Sequences of Interest

In some embodiments, nucleic acid constructs disclosed herein include a synthetic TCRT that is operably linked to a nucleic acid sequence of interest (FIG. 1). In such constructs, the nucleic acid sequence is located 3' (e.g. downstream) of the synthetic TCRT. A "nucleic acid sequence of interest" or a "nucleotide sequence of interest" of the nucleic acid constructs disclosed herein include any desirable nucleic acid sequence. For example, a suitable nucleic acid sequence can encode an RNA (i.e., it can be transcribed by an RNA polymerase). In some embodiments, a nucleic acid sequence of interest is an insertion site for the insertion of a sequence of interest. An "insertion site" is any nucleotide sequence that facilitates for convenient insertion and/or excision of additional nucleic acid sequences. The term "insertion site" encompasses sequences that facilitate any convenient cloning methodology (e.g., standard restriction enzyme/ligation based methods, integrase based methods, T4 DNA Polymerase based methods, BioBrick cloning, Circular Polymerase Extension Cloning (CPEC) cloning, etc.) (Quan, J. & Tian, J. Nat. Protoc. 6, 242-251 (2011); Shetty et al. J. Biol. Eng. 2, 5 (2008)). An example of one possible type of standard insertion site is a multiple cloning site (or polylinker), which is a stretch of sequences that contains multiple restriction enzyme sites that together facilitate convenient restriction enzyme/ligation based cloning methods.

Nucleic acid sequences of interest can include protein-coding sequences, non-protein coding sequences, or both. Nucleic acid sequences include, without limitation, sequences that encode proteins; sense RNA sequences; antisense RNA sequences; ribonucleic acid aptamers responsive to one or more environmental cues; and sequences responsive to intracellular and/or environmental cues. In some aspects, ribonucleic acid aptamers responsive to one or more environmental cues refer to engineered sequences (often through in vitro selection), whereas sequences responsive to intracellular and/or environmental cues refers to natural RNAs having these properties.

Nucleic Acid Constructs

The present disclosure provides nucleic acid constructs that include a synthetic translation-coupled regulator of transcription (synthetic TCRT) that includes a cis-regulator of translation, and an adapter translation-coupled regulator of transcription (adapter TCRT), wherein the cis-regulator of translation and the adapter TCRT are operably linked so that the transcription of downstream sequences (i.e., sequences that are 3' of and operably linked to the synthetic TCRT) is regulated by the cis-regulator of translation. In certain embodiments, the cis-regulator of translation is a regulator of translation initiation. In other embodiments, the cis-regulator of translation is a regulator of translation elongation (e.g., synthetic tRNAs).

The term "nucleic acid construct" is used interchangeably herein with the terms "recombinant nucleic acid construct" and "recombinant expression vector." "Recombinant," as used herein, means that a particular nucleic acid (DNA or RNA) is the product of various combinations of cloning, restriction, polymerase chain reaction (PCR) and/or ligation steps resulting in a construct having a structural coding or non-coding sequence distinguishable from endogenous nucleic acids found in natural systems. DNA sequences encoding polypeptides can be assembled from cDNA fragments or from a series of synthetic oligonucleotides, to provide a synthetic nucleic acid which is capable of being expressed from a recombinant transcriptional unit contained in a cell or in a cell-free transcription and translation system. Genomic DNA comprising the relevant sequences can also be used in the formation of a recombinant gene or transcriptional unit. Sequences of non-translated DNA may be present 5' or 3' from the open reading frame and may indeed act to modulate production of a desired product by various mechanisms (see "regulatory element", above). Alternatively, DNA sequences encoding RNA that is not translated may also be considered recombinant. Thus, e.g., the term "recombinant" polynucleotide or "recombinant" nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a codon encoding the same amino acid, a conservative amino acid, or a non-conservative amino acid. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

A "vector" or "expression vector" is a replicon, such as plasmid, phage, virus, or cosmid, to which another DNA segment, i.e. an "insert", may be attached so as to bring about the replication of the attached segment in a cell. An "expression cassette" comprises a DNA coding sequence operably linked to a promoter. The term "operably linked" refers to a juxtaposition wherein the components so described are in a relationship permitting them to function in their intended manner. For instance, a coding sequence is operably linked to a promoter (or the promoter can be said to be operably linked to the coding sequence) if the promoter affects the transcription or expression of the coding sequence.

Therefore, the terms "recombinant expression vector" or "nucleic acid construct" refer to a DNA molecule comprising a vector and at least one insert (e.g., a synthetic TCRT). Recombinant expression vectors are usually generated for the purpose of expressing and/or propagating the insert(s), or for the construction of other recombinant nucleotide sequences (e.g., the addition of a nucleic acid sequence of interest).

Nucleic acid constructs provided herein may further include a nucleic acid sequence of interest that is operably linked to a synthetic TCRT such that the synthetic TCRT regulates the transcription (via a translation-coupled mechanism) of the nucleic acid sequence of interest (e.g., an insertion site, e.g., a multiple cloning site, a protein-coding sequence, an antisense RNA, etc.).

In some aspects, nucleic acid constructs provided herein include two or more synthetic TCRTs. Nucleic acid constructs that include two or more synthetic TCRTs may include two or more of the same synthetic TCRT, two or more different synthetic TCRTs, or two or more of the same synthetic TCRT and one or more different synthetic TCRTs. Coupling two or more synthetic TCRTs to an operon will result in a multiplicative combination of the dynamic ranges of the two or more synthetic TCRTs. One of skill in the art can therefore use of multiple synthetic TCRTs to design operons with specific regulatory dynamic ranges as well as operons that respond to multiple signals.

Nucleic acid constructs that include two or more synthetic TCRTs may further include a nucleic acid sequence of interest that is regulated by the two or more synthetic TCRTs in the nucleic acid construct. In other words, two or more synthetic TCRTs may be linked in tandem and operably linked to a nucleic acid sequence of interest such that the synthetic TCRTs interact in a combinatorial way to regulate the transcription (via a translation-coupled mechanism) of the nucleic acid sequence of interest. In some embodiments, two or more synthetic TCRTs linked in tandem can be referred to as a NOR gate.

Cells Comprising a Nucleic Acid Construct

In another embodiment, provided herein is a cell comprising a nucleic acid construct disclosed herein. Because the term "nucleic acid construct" is used interchangeably with the term "recombinant expression vector," a cell comprising a nucleic acid construct is also referred to herein as a "recombinant cell." In other words, a recombinant cell is a cell comprising a nucleic acid construct. A "recombinant cell" can also be referred to herein as a "genetically modified cell." In some aspects, the cell comprising a nucleic acid construct is a prokaryotic cell and is therefore referred to as a "recombinant prokaryotic cell" or a "genetically modified prokaryotic cell." Cells of the disclosure include, without limitation, *Escherichia coli* and *Bacillus subtilis*.

Cells comprising a nucleic acid construct disclosed herein can comprise two or more nucleic acid constructs.

In some aspects, a cell comprising a first nucleic acid construct disclosed herein may further comprise a second nucleic acid construct that encodes a regulatory input molecule (e.g., an antisense or sense RNA) that can anneal to the cis-regulator of translation of the synthetic TCRT of the first nucleic acid construct. The expression of the regulatory input molecule from the second nucleic acid construct may be regulated by any mechanism for the control of transcription. In some aspects, a cell comprises a nucleic acid construct disclosed herein, and the nucleic acid construct further encodes a regulatory input molecule.

In some aspects, the activation of expression of a nucleic acid sequence under the control of a synthetic TCRT provided herein in a cell results in the activation or inactivation of one or more other genes in the cell, as a result of the increased expression of the nucleic acid sequence under the control of a synthetic TCRT provided herein. In some other aspects, the inactivation of expression of a nucleic acid sequences under the control of a synthetic TCRT provided herein in a cell results in the activation or inactivation of one or more other genes in the cell, as a result of the decreased expression of the nucleic acid sequence under the control of a synthetic TCRT provided herein.

In some aspects, cells are provided that comprise two or more nucleic acid constructs which comprise two or more different nucleic acid sequences of interest, and in which the nucleic acid constructs function in a gene network. Cells comprising a nucleic acid construct of the disclosure may be prepared by methods well known to those of skill in the art for the introduction of genetic material into cells. See, for example, *Molecular Cloning: A Laboratory Manual* ($3^{rd}$ *edition*), Cold Spring Harbor Press, (2001).

Methods

The present disclosure provides methods relating to the use and preparation of the nucleic acid constructs disclosed herein.

Methods of Regulating the Expression of a Nucleic Acid Sequence

In one aspect, provided herein are methods for regulating the expression of a nucleic acid sequence. Nucleic acid sequences that may be regulated include, without limitation, nucleotides that encode polypeptides, sense RNA molecules, antisense RNA molecules, RNA aptamers responsive to an intracellular or environmental cue, RNA sequences responsive to an intracellular or environmental cue, and tuned ribosome binding sites.

In one method for regulating the expression of a nucleic acid sequence, a nucleic acid construct is obtained that includes a nucleic acid sequence of interest under the control of a synthetic TCRT disclosed herein. The nucleic acid construct is then subjected to one or more conditions that stimulate or inhibit the translation of the leader peptide in the synthetic TCRT. Depending on the construct, the completion of translation of the leader peptide may cause increased or decreased transcription of the nucleic acid sequence of interest that is under the control of a synthetic TCRT disclosed herein. In some aspects, the completion of translation of the leader peptide causes increased transcription of a nucleic acid sequence that is under the control of a synthetic TCRT disclosed herein. In other aspects, the completion of translation of the leader peptide causes decreased transcription of a nucleic acid sequence that is under the control of a synthetic TCRT disclosed herein.

In another method for regulating the expression of a nucleic acid sequence, the nucleic acid of interest is operably linked a synthetic TCRT disclosed herein, to generate a nucleic acid construct having the nucleic acid sequence operably linked to a synthetic TCRT disclosed herein. The nucleic acid construct is then subjected to one or more conditions that stimulate or inhibit the translation of the leader peptide of the synthetic TCRT, and that, in turn, through the adapter translation-coupled regulator of transcription, result in activation or inactivation the transcription of the nucleic acid sequence of interest.

As provided above in the description of cis-regulators of translation, various different cis-regulators of translation that are responsive to various different conditions may be used with the synthetic TCRTs and nucleic acid constructs disclosed herein. Accordingly, various methods may be used to stimulate or inhibit the translation of the leader peptide of the synthetic TCRTs, including, without limitation: changing the concentration of an antisense nucleic acid molecule which binds to the cis-regulator of translation, changing the concentration of a small molecule which binds to the cis-regulator of translation, changing the concentration of a protein which binds to the cis-regulator of translation, changing the temperature to alter the conformation of the cis-regulator of translation, or changing the pH to alter the conformation of the cis-regulator of translation.

Methods of regulating the expression of a nucleic acid sequence may also include the regulation of a nucleic acid sequence by two or more synthetic TCRTs provided herein. In some aspects, a nucleic acid sequence may be prepared under the control of two or more synthetic TCRTs provided herein. In some aspects, a nucleic acid sequence that is under the control of two or more synthetic TCRTs provided herein is obtained.

If a nucleic acid sequence of interest is under the control of two or more synthetic TCRTs provided herein, and all of the synthetic TCRTs are the same, then a single method or condition may be used to enhance or inhibit the transcription of the nucleic acid sequence of interest. For example, if a nucleic acid sequence of interest is regulated by two synthetic TCRTs that are both regulated by the same antisense molecule only one type of antisense molecule may be required to regulate translation of the leader peptide (and thus, transcription of the nucleic acid sequence of interest).

If a nucleic acid sequence of interest is under the control of two or more synthetic TCRTs provided herein, and two or more of the synthetic TCRTs are different, then two or more methods or conditions may be used to regulate translation of a leader peptide (and thus, regulate transcription of the nucleic acid sequence of interest). In some aspects, when two or more different synthetic TCRTs are used for the control of expression of a nucleic acid sequence, the two or more different synthetic TCRTs function orthogonally to each other, so that a condition that regulates one synthetic TCRT does not regulate another synthetic TCRT.

Further provided herein are methods of modulating the level of expression of a nucleic acid sequence of interest. In one aspect, the level of expression of a nucleic acid sequence of interest under the control of a synthetic TCRT provided herein may be modulated by varying the composition of the synthetic TCRT(s) that regulate the nucleic acid sequence. For example, a nucleic acid sequence under the control of a first synthetic TCRT having a certain cis-regulator of translation may be expressed at a different level than the same nucleic acid sequence of interest under the control of second synthetic TCRT that has a different cis-regulator of translation. In another aspect, the level of expression of a nucleic acid sequence of interest under the control of a synthetic TCRT provided herein may be modulated by varying the number of synthetic TCRT(s) that regulate the nucleic acid sequence of interest. For example, a nucleic acid sequence of interest under the control of one synthetic TCRT may be expressed at a level that is different than the level of expression of the same nucleic acid sequence of interest under the control of two synthetic TCRTs provided herein.

Further provided herein are methods of obtaining a predictable level of expression of a nucleic acid sequence of interest. Synthetic TCRTs provided herein may cause, in response to a condition that supports translation from the cis-regulator of translation in the synthetic TCRT, a predictable level of expression of a nucleic acid sequence of interest under the control of the synthetic TCRT. This level of expression may be consistent for different nucleic acid sequences of interest under the control of the same synthetic TCRT. Accordingly, one of skill may obtain a predictable level of expression of a nucleic acid sequence of interest, by exposing a nucleic acid sequence of interest that is operably linked to a synthetic TCRT to a condition that supports translation from the cis-regulator of translation in the synthetic TCRT.

Methods for the regulation of expression of a nucleic acid sequence of interest also include regulation of a nucleic acid sequence of interest through the use of a genetic network. In such methods, the activation or inactivation of expression of one nucleic acid sequence of interest leads to the activation or inactivation of expression of one or more other nucleic acid sequence(s) of interest in the same biochemical environment.

Methods of Preparing Nucleic Acid Constructs

Provided herein are methods for preparing nucleic acid constructs disclosed herein. Nucleic acid constructs disclosed herein may be prepared by standard molecular biology techniques well known to those of skill in the art. See, e.g., *Molecular Cloning: A Laboratory Manual* ($3^{rd}$ edition), Cold Spring Harbor Press, (2001). In some aspects, nucleic acid constructs may be prepared by annealing two or more different sequences. In some aspects, PCR-based techniques may be used to prepare a nucleic acid construct. In some aspects, nucleic acid constructs may be prepared by de novo synthesis.

Applications/Systems Biology

The compositions and methods disclosed herein may further be used for synthetic gene regulation. As used herein, the terms "gene" and "nucleic acid sequence of interest" are used interchangeably, and refer to any nucleic acid sequence, including both protein-coding and non-protein coding sequences.

In some aspects, Boolean control of expression of a gene may be achieved by providing a gene under the regulatory control of a synthetic TCRT disclosed herein. Regulation of a gene by a synthetic TCRT disclosed herein may allow for a large difference in expression level of the gene between the activated (or "on") state of the gene, and the inactivated (or "off") state of the gene. Differences in expression level of a gene include differences in the amount of an RNA transcript of the gene and/or differences in the amount of a protein encoded by the gene. In some aspects, a gene placed under the control of a synthetic TCRT disclosed herein may have about a 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000-fold difference in expression between the activated state of the gene and the inactivated state of the gene.

In some aspects, Boolean control of expression of a gene may be achieved by providing a gene under the regulatory control of two or more of the synthetic TCRTs disclosed herein. A gene under the regulatory control of two or more of the synthetic TCRTs disclosed herein, may be under regulatory control of two or more of the same synthetic TCRTs, it may be under the regulatory control of two or more different synthetic TCRTs, or it may be under the regulatory control of two or more of the same synthetic TCRTs and one or more additional, different synthetic TCRTs. Providing a gene under the regulatory control of two or more of the synthetic TCRTs disclosed herein can allow for a large difference in expression level of the gene between the activated (or "on") state of the gene, and the inactivated (or "off") state of the gene. In some aspects, a gene under the control of two or more of the synthetic TCRTs disclosed herein may have about a 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000-fold difference in expression between the activated state of the gene and the inactivated state of the gene.

In some aspects, tuned expression of a gene can be achieved by providing a gene under the regulatory control of a synthetic TCRT disclosed herein. A gene under the regulatory control of a synthetic TCRT disclosed herein may have a precise expression level in response to a regulatory stimulus. In some aspects, tuned expression of a gene may be achieved by providing a gene under the regulatory control of two or more synthetic TCRTs disclosed herein. A gene under the regulatory control of two or more synthetic TCRTs disclosed herein may have a precise expression level in response to one or more regulatory stimuli.

In some aspects, a genetic circuit may be prepared wherein one or more genes are provided under the control of a synthetic TCRT disclosed herein.

In some aspects, a network of genes having regulated gene expression may be prepared wherein two or more different genes that are each under the regulatory control of a synthetic TCRT disclosed herein are provided in the same biochemical environment. In some aspects, two or more different genes in the same biochemical environment are in the same cell. In other aspects, two or more different genes in the same biochemical environment are in the same cell extract. In other aspects, two or more different genes in the same biochemical environment are in the same in vitro transcription system. In some aspects, a genetic circuit may be prepared by providing two or more different genes in the same biochemical environment, wherein each gene is under regulatory control of a synthetic TCRT disclosed herein.

In a network of genes wherein two or more different genes are each under regulatory control of a synthetic TCRT disclosed herein, the level of expression of one gene may affect the level of expression of a different gene of the gene network. The level of expression of one gene may affect the level of expression of one or more different genes by any mechanism whereby the level of expression of one gene under the control of a synthetic TCRT provided herein can affect the initiation of translation from a cis-regulator of translation of another synthetic TCRT provided herein. For example, in a network of genes, one gene under the regulatory control of a synthetic TCRT disclosed herein may be an antisense RNA molecule. That antisense RNA molecule, may, in turn, bind to the cis-regulator of translation of a different synthetic TCRT in the same network, and thereby affect the expression of the gene under the regulatory control of that synthetic TCRT. In another example, in a network of genes, one gene under the regulatory control of a synthetic TCRT disclosed herein may encode a protein. That protein, may, in turn, bind to the cis-regulator of translation of a different synthetic TCRT in the same network, and thereby affect the expression of a different gene in the same network. In another example, in a network of genes, one gene under the regulatory control of a synthetic TCRT disclosed herein may encode a protein. That protein, may, in turn, be involved in the generation, storage, or transport of a small molecule that affects the cis-regulator of translation of a different synthetic TCRT in the same network. Through this mechanism, the expression of one gene may affect the expression of a different gene in the same network. As would be readily understood by one of skill in the art, the above examples whereby the level of expression of one gene under the control of a synthetic TCRT provided herein may affect the level of expression of one or more different gene(s) under the control of a synthetic TCRT provided herein are for illustrative purposes, and are not limiting.

In a network of genes wherein two or more different genes are each under regulatory control of a synthetic TCRT disclosed herein, activation of expression of one gene may trigger the activation of expression of a different gene of the gene network. Alternatively, in a network of genes wherein two or more different genes are each under regulatory control of a synthetic TCRT disclosed herein, activation of expression of one gene may trigger the inactivation of expression of a different gene of the gene network. In some aspects, in a network of genes wherein three or more different genes are each under regulatory control of a synthetic TCRT disclosed herein, activation of expression of one gene may trigger the activation of expression of another gene of the gene network and inactivation of expression of yet another gene of the gene network.

In a network of genes wherein two or more different genes are each under regulatory control of a synthetic TCRT disclosed herein, inactivation of expression of one gene may trigger the activation of expression of a different gene of the gene network. Alternatively, in a network of genes wherein two or more different genes are each under regulatory control of a synthetic TCRT disclosed herein, inactivation of expression of one gene may trigger the inactivation of expression of a different gene of the gene network. In some aspects, in a network of genes wherein three or more different genes are each under regulatory control of a synthetic TCRT disclosed herein, inactivation of expression of one gene may trigger the activation of expression of another gene of the gene network and inactivation of expression of yet another gene of the gene network.

In a network of genes wherein two or more different genes are each under regulatory control of a synthetic TCRT disclosed herein, Boolean control of the expression of one or more of the genes in the network may be achieved. In some networks of genes wherein two or more different genes are each under regulatory control of a synthetic TCRT disclosed herein, activation of expression of one gene may trigger a 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, or 10,000-fold difference in expression in another gene in the network of genes.

In a network of genes wherein two or more of different genes are under the regulatory control of different synthetic TCRTs disclosed herein, different synthetic TCRTs may have orthogonal responses to different regulatory stimuli. For example, if one synthetic TCRT responds strongly to a certain stimulating short RNA molecule, a different synthetic TCRT may have very little or no response to that same short RNA molecule. In such an instance, the responses of the two different synthetic TCRTs are orthogonal in regards to that particular short RNA molecule. In another example, two different synthetic TCRTs are orthogonal if one synthetic TCRT responds strongly to a certain change in temperature, while the other synthetic TCRT has little to no response in regards to that same change in temperature.

Two or more different nucleic acid constructs in a network of genes may be said to respond "orthogonally" to a certain stimulus if, in response to the stimulus, the synthetic TCRT of one nucleic acid construct causes a level of expression of a gene under the control of that synthetic TCRT that is at least about 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1500, 2000, 2500, 3000, 3500, 4000, 4500, 5000, 6000, 7000, 8000, 9000, or 10,000-fold greater or less than the level of expression of a gene or genes that are under control of different synthetic TCRTs, in response to the same stimulus.

Further provided herein are networks of genes and genetic circuits having two or more nucleic acid constructs wherein two or more different genes are under control of a synthetic TCRT construct disclosed herein, and wherein each of the genes under the control of a synthetic TCRT disclosed herein responds orthogonally to a certain stimulus as compared to the response to the same stimulus of genes under the control of a different synthetic TCRT disclosed herein. In another example, provided herein are networks of genes and genetic circuits having two or more nucleic acid constructs wherein two or more genes are under the control of two or more of the synthetic TCRTs disclosed herein, and wherein at least two of the synthetic TCRTs disclosed herein respond to RNA-OUT(3) (SEQ ID NO: 31), RNA-OUT(4) (SEQ ID NO: 32), RNA-OUT(9) (SEQ ID NO: 33), RNA-OUT(20) (SEQ ID NO: 34), or RNA-OUT(23) (SEQ ID NO: 35).

Networks of genes can be used to construct logic gates such as NOR gates. A NOR gate is a digital logic gate that implements logical NOR, which is the result of the negation of the OR operator. In a NOR gate an "HIGH" output (1) results if both of the inputs to the gate are "LOW" (0); if one or both inputs is "HIGH" (1), a "LOW" output (0) results. Combinations of NOR gates can be combined to generate any other logical function. In some embodiments, two or more synthetic TCRTs are linked in tandom and together regulate a single nucleic acid sequence of interest, thus forming a NOR gate. In some such embodiments, all tandemly linked synthetic TCRTs must be in an "ON" state in order for transcription to result. In other words, transcription of the nucleic acid sequence of interest will be minimal to absent if any one of the tandemly linked synthetic TCRTs is in an "OFF" state (FIG. 7).

Subject synthetic TCRTs disclosed herein find use in the field of metabolic engineering. Because transcription levels can be efficiently and predictably controlled by placing a protein-encoding nucleic acid sequence downstream of synthetic TCRT, as disclosed herein, the activity of metabolic pathways can be precisely controlled and tuned by controlling the level of specific enzymes within a metabolic pathway of interest. In addition enzymes of metabolic pathways of interest can be regulated by and/or integrated into networks as described above. Metabolic pathways of interest include those used for chemical (fine chemicals, fuel, antibiotics, toxins, agonists, antagonists, etc.) and/or drug production. Because the synthetic TCRTs disclosed herein provide an efficient way to construct predictable expression systems by reusing characterized genetic parts, they reduce the need to perform large scale library selection to optimize expression of various enzymes within a given pathway of interest.

Biosynthetic pathways of interest include but are not limited to (1) the mevalonate pathway (i.e., HMG-CoA reductase pathway) (converts acetyl-CoA to dimethylallyl pyrophosphate (DMAPP) and isopentenyl pyrophosphate (IPP), which are used for the biosynthesis of a wide variety of biomolecules including terpenoids/isoprenoids), (2) the non-mevalonate pathway (i.e., the "2-C-methyl-D-erythritol 4-phosphate/1-deoxy-D-xylulose 5-phosphate pathway" or "MEP/DOXP pathway" or "DXP pathway")(also produces DMAPP and IPP, instead by converting pyruvate and glyceraldehyde 3-phosphate into DMAPP and IPP via an alternative pathway to the mevalonate pathway), (3) the polyketide synthesis pathway (produces a variety of polyketides via a variety of polyketide synthase enzymes. Polyketides include naturally occurring small molecules used for chemotherapy (e.g., tetracyclin, and macrolides) and industrially important polyketides include rapamycin (immunosuppressant), erythromycin (antibiotic), lovastatin (anticholesterol drug), and epothilone B (anticancer drug)), (4) fatty acid synthesis pathways, (5) the DAHP (3-deoxy-D-arabino-heptulosonate 7-phosphate) synthesis pathway, (6) pathways that produce potential biofuels (such as short-chain alcohols and alkane, fatty acid methyl esters and fatty alcohols, isoprenoids, etc.), etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Methods

Plasmid construction. pCCL-000 is a control plasmid that does not include the GFP gene, and pCCL-008 includes the superfolder GFP gene, with its own RBS, under the transcriptional control of the wild-type tna regulatory leader-peptide element, driven by a J23119(SpeI) promoter. The construction of plasmids pCCL-000 and pCCL-008 is described previously (Liu et. al, Nat. Biotech. 29, 164-168 (2011)). To obtain plasmid pCCL-036, a DNA fragment including a variant tna element with RNA-IN fused to tnaC was assembled via PCR amplification from pCCL-008 using primers 5'-GGCCACTAGTGCGAAAAATCAATAAGGA-GACAACAAGATGTGCGAACTCGATATGA ATATCT-TACATATATG (SEQ ID NO: 1) and 5'-CTTCAG-CACGCGTCTTGTAG (SEQ ID NO: 2). This fragment, flanked by SpeI and MluI sites, was then digested with SpeI and MluI and inserted into a similarly digested pCCL-008 plasmid to replace the wild-type tna element included in pCCL-008. The resulting plasmid, pCCL-036, therefore includes the superfolder GFP gene under the transcriptional control of a variant tna element whose leader-peptide coding region, tnaC, is under the translational control of the fused RNA-IN.

To obtain plasmid pCCL-037, a DNA fragment including a variant tna element with RNA-IN fused to a truncated tnaC was assembled via PCR amplification from pCCL-008 using primers 5'-GGCCACTAGTGCGAAAAATCAATAAGGA-GACAACAAGATGTGCGAACTCGATATAT GTGTGAC-CTCAAAATGGTT (SEQ ID NO: 3) and 5'-CTTCAG-CACGCGTCTTGTAG (SEQ ID NO: 2). As described for pCCL-036, this fragment, flanked by SpeI and MluI sites, was digested with SpeI and MluI and inserted into a similarly digested pCCL-008 plasmid.

To obtain plasmid pCCL-038, a DNA fragment including a variant tna element with crR12 fused to tnaC was assembled via PCR amplification from template pCCL-036 using primers 5'-GGCCACTAGTGAATTCTACCAT-TCACCTCTTGGATTTGGGTATTAAAGAGGAGAAAG GTACCATGAATATCTTACATATATG (SEQ ID NO: 4) and 5'-TTCAGCACGCGTCTTGTAGG (SEQ ID NO: 5). This fragment, flanked by SpeI and MluI sites, was digested with SpeI and MluI and inserted into a similarly digested pCCL-036 plasmid to replace the variant tna element included in pCCL-036. The resulting plasmid, pCCL-038, therefore includes the superfolder GFP gene under the transcriptional control of a variant tna element whose leader-peptide coding region, tnaC, is under the translational control of the fused crR12.

From pCCL-037, Phusion Site-Directed Mutagenesis (New England Biolabs) was used to obtain plasmids pCCL-IN-3, pCCL-IN-4, pCCL-IN-9, pCCL-IN-20, and pCCL-IN-23. These plasmids are identical to pCCL-037 except for point mutations in the RNA-IN region. The variant RNA-IN units corresponding to pCCL-IN-3, pCCL-IN-4, pCCL-IN-9, pCCL-IN-20, and pCCL-IN-23 are RNA-IN-3, RNA-IN-4, RNA-IN-9, RNA-IN-20, and RNA-IN-23, respectively. These include specificity-modulating mutations we recently developed. In our nomenclature, RNA-IN-3, RNA-IN-4, RNA-IN-9, RNA-IN-20, and RNA-IN-23 correspond to the sense mutants S4, S5, S31, S34, and S49, respectively.

pSLQ214k and pSLQ220k were constructed from plasmids pSLQ214 (expressing RNA-OUT from the J23119 (SpeI) promoter) and pSLQ220 (expressing no RNA-OUT), respectively, except for their antibiotic resistance markers. (pSLQ214 and pSLQ220 are based on the RNA-OUT expression plasmids we recently developed, but with constitutive rather than inducible promoters.) Standard cloning techniques were used to replace ampicillin resistance markers in pSLQ214 and pSLQ220 with kanamycin resistance markers, yielding plasmids pSLQ214k and pSLQ220k. pSLQ214k expresses RNA-OUT from the constitutive J23119(SpeI) promoter; pSLQ220k does not include RNA-OUT.

To obtain plasmid pSLQtaR12k, a 106-bp DNA fragment including the 71-bp taR12 sequence (Isaacs et. al, Nat. Biotech. 22, 841-847 (2004)) was custom synthesized (Integrated DNA Technologies) and then PCR amplified using primers 5'-CCGAGCTAGCTCAGTCCTAGGTAT (SEQ ID NO: 6) and 5'-CCGAGGATCCTCTAGAGATATATGG (SEQ ID NO: 7). The PCR product was digested with NheI and BamHI and inserted into a similarly digested pSLQ214k to replace the RNA-OUT sequence with the taR12 sequence. The resulting plasmid, pSLQtaR12k, is otherwise identical to pSLQ214k. pSLQtaR12k therefore expresses taR12 from the constitutive J23119(SpeI) promoter.

From pSLQ214k, we used Phusion Site-Directed Mutagenesis (New England Biolabs) to obtain plasmids pSLQ-OUT-3, pSLQ-OUT-4, pSLQ-OUT-9, pSLQ-OUT-20, and pSLQ-OUT-23. These plasmids, identical to pSLQ214k except for point mutations in the RNA-OUT region, express RNA-OUT variants from the constitutive J23119(SpeI) promoter. The RNA-OUT variants corresponding to pSLQ-OUT-3, pSLQ-OUT-4, pSLQ-OUT-9, pSLQ-OUT-20, and pSLQ-OUT-23 are RNA-OUT-3, RNA-OUT-4, RNA-OUT-9, RNA-OUT-20, and RNA-OUT-23, respectively. These include specificity-modulating mutations we recently developed. In our nomenclature, RNA-OUT-3, RNA-OUT-4, RNA-OUT-9, RNA-OUT-20, and RNA-OUT-23 correspond to reported antisense mutants A4, A5, A31, A34, and A49, respectively.

To create pTHSS-08, a region of the inducible RNA-OUT expression plasmid, was PCR amplified using primers 5'-TAATATACTAGTAGAGAGCGTTCACCGACAAAC (SEQ ID NO: 8) and 5'-TAATATAGATCTTACCGCTGTT-GAGATCCAGTTC (SEQ ID NO: 9) and subsequently digested with SpeI and BglII. A second fragment was PCR amplified from pSQL214k using primers 5'-TATAATTCTA-GAGTCACACTGGCTCACCTTCG (SEQ ID NO: 10) and 5'-TAATATGGATCCTTGAGAGTTTTCGCCCCGAAG (SEQ ID NO: 11) and subsequently digested with XbaI and BamHI. Ligation of the two fragments yielded pTHSS-08, which expresses RNA-OUT under the control of an inducible lac promoter.

To obtain pTHSS-06, the RNA-OUT sequence in pTHSS-08 was replaced by the taR12 sequence through PCR amplification with 5'-phosphorylated primers 5'-TGAAAATTAACTTACTACTACCATATATCTCTA-GAGGATCCAAACTCGAGTAAGGAT CTC (SEQ ID NO: 12) and 5'-TTAACCACCACTACCAATCACCTC-CTGGATTTGGGTTGTGCTCAGTATCTTGTTATCC GC (SEQ ID NO: 13). Following blunt ligation, this yielded pTHSS-06, which expresses taR12 under the control of an inducible lac promoter.

Multiple-step BioBrick cloning was used to produce all NOR circuit plasmids. First, we introduced BioBrick restriction enzyme sites (BglII/BamHI in combination with HindIII) into the plasmids pCCL-IN-3, pCCL-IN-4, pCCL-IN-9, and pCCL-IN-20, using the standard format of 5'-promoter-BglII site-TAATAA-RNA-IN-tna converter-BamHI-sfGFP-HindIII-3'. This resulted in plasmids pSLQ941, pSLQ942, pSLQ943, and pSLQ944. Insertion fragments were then obtained by digestion of the above plasmids with BglII and HindIII, and backbone fragments were obtained by digestion with BamHI and HindIII. Ligation of fragment combinations gave two-input NOR gate compositions, yielding plasmids pSLQ946 for NOR(3,4) (RNA-IN-3-tna tethered with RNA-IN-4-tna), pSLQ947 for NOR(9,20) (RNA-IN-9-tna tethered with RNA-IN-20-tna), and pSLQ967 for NOR(3,20) (RNA-IN-3-tna tethered with RNA-IN-20-tna). The same cloning procedures were reiterated to obtain three-input and four-input NOR circuits, yielding pSLQ970 for NOR(4,9,20), pSLQ971 for NOR(3,4,9), and pSLQ948 for NOR(3,4,9,20).

The Csy4 expression plasmid with a cassette expressing wild-type RNA-OUT, pSLQ505, was obtained as described by Qi et al. 27 (Qi et. al, Nat. Biotech., in press). To produce mutant RNA-OUTs, we performed Phusion Site-Directed Mutagenesis on pSLQ505, following the same steps as described for cloning pSLQ-OUT-3, pSLQ-OUT-4, pSLQ-OUT-9, pSLQ-OUT-20, and pSLQ-OUT-23. This gave us plasmids pSLQ932, pSLQ933, pSLQ677, and pSLQ934, which express RNA-OUT-3, RNA-OUT-4, RNA-OUT-9, and RNA-OUT-20, respectively. To produce plasmids expressing two RNA-OUT variants simultaneously, we inserted the Csy4 expression cassette, using restriction enzymes SphI and AatII, into plasmids that coexpressed pairs of RNA-OUT RNAs. This yielded plasmids pSLQ1009, pSLQ1010, and pSLQ1011, which coexpress RNA-OUT-3 and RNA-OUT-4, RNA-OUT-9 and RNA-OUT-20, and RNA-OUT-3 and RNA-OUT-20, respectively.

To produce pSLQ528, a plasmid expressing the theophylline-aptamer-RNA-OUT fusion, we changed the antibiotic marker of a previously described plasmid pAPA1307 (Qi et. al, *Nucleic Acids Res.* 2012 July; 40(12):5775-86. Epub 2012 Mar. 1) from AmpR to KanR. This allowed us to cotransform pSLQ528 and pCCL-037 using kanamycin and ampicillin as selectable markers.

All plasmid propagation steps during cloning were done in Top10 cells (Invitrogen). Table 3 lists all plasmids used in this study.

TABLE 3

List of plasmids used.

| Name | Origin of Replication | Resistance Marker | Description |
|---|---|---|---|
| pCCL-000 | pSC101 | Amp | Cloning vector and control vector. |
| pCCL-008 | pSC101 | Amp | Contains the wild-type tna element inserted before a GFP gene, all driven by the J23119(SpeI) promoter. |
| pCCL-036 | pSC101 | Amp | pCCL-008 with the RNA-IN unit replacing the first 24 nucleotides of the tna element, thus placing tnaC under the translational control of RNA-IN. |
| pCCL-037 | pSC101 | Amp | pCCL-008 with the RNA-IN unit replacing the first 39 nucleotides of the tna element, thus placing tnaC under the translational control of RNA-IN. |
| pCCL-038 | pSC101 | Amp | pCCL-008 with the crR12 unit replacing the first 24 nucleotides of the tna element, thus placing tnaC under the translational control of crR12. |
| pCCL-IN-3 | pSC101 | Amp | pCCL-037 with RNA-IN-3 replacing RNA-IN. |
| pCCL-IN-4 | pSC101 | Amp | pCCL-037 with RNA-IN-4 replacing RNA-IN. |
| pCCL-IN-9 | pSC101 | Amp | pCCL-037 with RNA-IN-9 replacing RNA-IN. |
| pCCL-IN-20 | pSC101 | Amp | pCCL-037 with RNA-IN-20 replacing RNA-IN. |
| pCCL-IN-23 | pSC101 | Amp | pCCL-037 with RNA-IN-23 replacing RNA-IN. |
| pSLQ214k | ColE1 | Kan | Contains RNA-OUT under the control of the J23119(SpeI) promoter. |
| pSLQ220k | ColE1 | Kan | pSLQ214k with RNA-OUT removed. |
| pSLQtaR12k | ColE1 | Kan | pSLQ214k with taR12 replacing RNA-OUT. |
| pSLQ-OUT-3 | ColE1 | Kan | pSLQ214k with RNA-OUT-3 replacing RNA-OUT. |
| pSLQ-OUT-4 | ColE1 | Kan | pSLQ214k with RNA-OUT-4 replacing RNA-OUT. |
| pSLQ-OUT-9 | ColE1 | Kan | pSLQ214k with RNA-OUT-9 replacing RNA-OUT. |
| pSLQ-OUT-20 | ColE1 | Kan | pSLQ214k with RNA-OUT-20 replacing RNA-OUT. |
| pSLQ-OUT-23 | ColE1 | Kan | pSLQ214k with RNA-OUT-23 replacing RNA-OUT. |
| pTHSS-08 | ColE1 | Kan | Contains RNA-OUT under the control of the inducible lac promoter. |
| pTHSS-06 | ColE1 | Kan | Contains taR12 under the control of the inducible lac promoter. |
| pSLQ946 | pSC101 | Cm | Contains tandem RNA-IN-3-tna and RNA-IN-4-tna units (two-input NOR gate). |
| pSLQ947 | pSC101 | Cm | Contains tandem RNA-IN-9-tna and RNA-IN-20-tna units (two-input NOR gate). |
| pSLQ967 | pSC101 | Cm | Contains tandem RNA-IN-3-tna and RNA-IN-20-tna units (two-input NOR gate). |
| pSLQ970 | pSC101 | Cm | Contains tandem RNA-IN-4-tna, RNA-IN-9-tna, and RNA-IN-20-tna units (three-input NOR gate). |
| pSLQ971 | pSC101 | Cm | Contains tandem RNA-IN-3-tna, RNA-IN-4-tna, and RNA-IN-9-tna units (three-input NOR gate). |
| pSLQ948 | pSC101 | Cm | Contains tandem RNA-IN-3-tna, RNA-IN-4-tna, RNA-IN-9-tna, and RNA-IN-20-tna units (four-input NOR gate). |

TABLE 3-continued

List of plasmids used.

| Name | Origin of Replication | Resistance Marker | Description |
|---|---|---|---|
| pSLQ679 | ColEI | Amp | Contains an aTc-inducible Csy4 expression cassette. |
| pSLQ932 | ColEI | Amp | Contains an aTc-inducible Csy4 expression cassette and an RNA-OUT-3 expression cassette. |
| pSLQ933 | ColEI | Amp | Contains an aTc-inducible Csy4 expression cassette and an RNA-OUT-4 expression cassette. |
| pSLQ677 | ColEI | Amp | Contains an aTc-inducible Csy4 expression cassette and an RNA-OUT-9 expression cassette. |
| pSLQ934 | ColEI | Amp | Contains an aTc-inducible Csy4 expression cassette and an RNA-OUT-20 expression cassette. |
| pSLQ1009 | ColEI | Amp | Contains an aTc-inducible Csy4 expression cassette and a cassette expressing both RNA-OUT-3 and RNA-OUT-4. |
| pSLQ1010 | ColEI | Amp | Contains an aTc-inducible Csy4 expression cassette and a cassette expressing both RNA-OUT-9 and RNA-OUT-20. |
| pSLQ1011 | ColEI | Amp | Contains an aTc-inducible Csy4 expression cassette and a cassette expressing both RNA-OUT-3 and RNA-OUT-20. |
| pSLQ213 | pSC101 | Cm | pSLQ946 with RNA-IN-3-tna, RNA-IN-4-tna, and GFP removed |
| pSLQ528 | ColEI | Kan | Contains a cassette expressing a functional theophylline-aptamer-RNA-OUT fusion. |

Cell culture. To characterize the behavior of individual regulators, appropriate plasmid combinations were transformed into Top10 cells and plated on solid LB media (Difco) supplemented with appropriate antibiotics (ampicillin at 100 mg/mL, kanamycin at 50 mg/mL, and chloramphenicol at 30 mg/mL). After overnight incubation at 37° C., a colony was used to inoculate liquid 2YT media (5 mL, Teknova) including antibiotics. Cultures were shaken overnight at 200 rpm at 37° C., after which 5 mL of each overnight culture was used to inoculate 5 mL of MOPS modified rich buffer (Teknova) including antibiotics. Cultures were shaken overnight at 200 rpm at 37° C. 4 mLs of each culture were used to inoculate 400 mLs of MOPS modified rich buffer including antibiotics in a 2 mL 96-well block. These cultures were then grown at 37° C. at 1000 rpm in a bench top shaker (Vortemp) for 5 hours. Cells comprising pCCL-000 and pSLQ220k were also grown in the same 96-well block for the determination of background autofluorescence.

To show concentration dependence of our regulators on RNA-OUT or taR12 as appropriate, the same cell culture procedure was employed except that plasmids including RNA-OUT or taR12 under the control of the lac promoter (these are plasmids pTHSS-08 and pTHSS-06, respectively) were used, different concentrations of IPTG (Sigma-Aldrich) were added, and cells were grown for 18 hours instead of 5 hours to ensure sufficient induction. These cells were then diluted 4-fold into MOPS modified rich buffer before characterization.

For NOR gate experiments, plasmids pSLQ946, pSLQ947, pSLQ967, pSLQ970, pSLQ971, and pSLQ948, transformed along with plasmids pSLQ679 (no RNA-OUT), pSLQ932, pSLQ933, pSLQ677, and pSLQ934 in pairwise combinations into Top10 cells. We also transformed pSLQ946 with pSLQ1009, pSLQ947 with pSLQ1010, and pSLQ967 with pSLQ1011 into Top10 cells. Three single colonies for each combination were picked from LB agar plates into MOPS modified rich buffer including proper antibiotics, and shaken at 200 rpm overnight at 37° C. 3 mLs of each culture were then used to inoculate 300 mLs of fresh MOPS modified rich buffer, supplemented with the proper antibiotics and 2 µM anhydrotetracycline (aTc, Sigma-Aldrich) to induce Csy4 expression. Cells were grown for 12 hours to ensure sufficient induction before measurements.

For the theophylline-induction experiments, we cotransformed plasmids pSLQ528 and pCCL-037 into Top10 cells. Three single colonies were picked from LB agar plates into MOPS modified rich buffer including proper antibiotics and shaken at 200 rpm overnight at 37° C. 3 mLs of each culture were then used to inoculate 300 mLs of fresh MOPS modified rich buffer supplemented with antibiotics and theophylline (2.5 mM) as well as 300 mLs of fresh MOPS modified rich buffer supplemented with antibiotics but no theophylline. These cultures were then grown at 37° C. at 1000 rpm in a bench top shaker (Vortemp) for 5 hours.

For all experiments, no additional tryptophan was added as MOPS modified rich Buffer Includes Sufficient Tryptophan to Induce Ribosomal Stalling in the Tna Element.

Measuring relative GFP expression. Fluorescence of cells comprising the superfolder GFP reporter gene under the control of regulators was used to determine activities. First, 200 mL of cells prepared according to the cell culture methods were transferred to 96-well plates (Costar 3603). Fluorescence (excitation at 485 nm, emission at 510 nm) and optical densities (600 nm) were then measured using a fluorescence plate reader (Tecan Safire2). The ratio of fluorescence to optical density (RFU/OD) was calculated and the background RFU/OD corresponding to cells comprising pCCL-000 (a vector without the superfolder GFP gene) and pSLQ220k (a vector that does not produce any antisense RNA) was subtracted where noted.

Flow cytometry measurements. Samples prepared according to the cell culture methods were diluted 250-fold in phosphate buffered saline and analyzed using a flow cytometer (Partec Cyflow Space) in the 4 parameters of time, forward scatter (FSC), side scatter (SSC), and GFP fluorescence (488 nm excitation, 520 nm band pass emission filter). Data for at least 50,000 cellular counts (triggered by SSC) were collected for each sample. Counts were gated by side and forward scatter. Fluorescence gain was adjusted such that the fluorescence intensity (reported in relative fluorescence units, RFUs) of bacteria including pCCL-000, a plasmid without a GFP gene, centered at approximately 6.7 RFUs. Data were processed using FCS Express Version 3.0 (De Novo Software).

Fluorescence microscope measurement. 1 µL of each sample prepared according to the cell culture methods was placed on a poly-L-lysine (Sigma-Aldrich) gel pad and observed under a Zeiss Axio Observer D1 microscope (excitation filter 470 nm/40 nm, emission filter 525 nm/50 nm). The brightness and contrast levels of all microscopic pictures were adjusted to the same level using ImageJ (U. S. National Institutes of Health, http://imagej.nih.gov/ij/).

RNA synthesis for SHAPE experiments. A DNA template for transcription of each RNA, inserted in the context of a T7 promoter and a 3'-flanking structure cassette (Low et. al, Methods 52, 150-158 (2010)), was generated by PCR. Each PCR product was recovered by ethanol precipitation and resuspended in 150 mL of TE buffer (10 mM Tris, 1 mM EDTA, pH 8.0) for use as templates in run-off transcription. Transcription reactions (1.0 mL, 37° C., 12-14 h) included 40 mM Tris (pH 8.0), 20 mM $MgCl_2$, 10 mM DTT, 2 mM spermidine, 0.01% (v/v) Triton X-100, 5 mM each NTP, 50 mL of PCR-generated template, 0.12 U/mL RNase Inhibitor (Promega) and 0.1 mg/mL of T7 RNA polymerase. The RNA products were purified by denaturing polyacrylamide gel electrophoresis (8% polyacrylamide, 7 M urea, 29:1 acrylamide:bisacrylamide, 32 W, 2 h), excised from the gel, and recovered by passive elution and ethanol precipitation. The purified RNA (~3 nmol) was resuspended in 200 mL TE.

RNAs were then subjected to structure-selective RNA modification by 1M7 (6.5 mM, final), as described previously (Mortimer et. al, *J. Am. Chem. Soc.* 129, 4144-4145 (2007)). This was followed by primer extension, capillary electrophoresis, and data analysis using the procedure outlined by Low and Weeks using a signal decay correction and scaling factor for replicate experiments (Low et. al, Methods 52, 150-158 (2010)).

Secondary structure prediction using SHAPE reactivity constraints. SHAPE intensities were converted into a pseudo-free energy change term in the RNAstructure (version 5.2) program using the following relation (Mortimer et. al, *Nat. Protocols* 4, 1413-1421 (2009)). $\Delta G_{SHAPE}=m*\ln[SHAPE\ reactivity+1.0]+b$. The intercept, b, is the free-energy bonus for formation of a base pair with zero or low SHAPE reactivity, whereas m, the slope, drives an increasing penalty for base pairing as the SHAPE reactivity increases. These parameters dictate the strength of the experimental contribution to the energy function. The b and m parameters were set to −0.8 and 2.6 kcal $mol^{-1}$, respectively (Reuter et. al, *BMC Bioinformatics* 11, 129 (2010)).

Results

Adapter design. Our adapter is based on the leader-peptide regulatory element from the tna operon of *Escherichia coli* (Gong et. al, *Science* 297, 1864-1867 (2002)). This regulatory element includes, from 5' to 3', an RBS, the coding region for a short leader peptide (tnaC), a Rho factor-binding site, and a stretch of RNA required for Rho factor-mediated transcriptional termination. The controlled structural genes, tnaA and tnaB, each with its individual RBS, follow. In the tna regulatory element's natural mechanism, full translation of tnaC results in ribosomal stalling and blockage of a Rho factor-binding site adjacent to tnaC's stop codon (FIG. 2) (Gong et. al, Science 297, 1864-1867 (2002); Gong et. al, Proc. Natl. Acad. Sci. USA 98, 8997-9001 (2001); and Seidelt et. al, Science 326, 1412-1415 (2009)). More precisely, stalling occurs only in the presence of free tryptophan, which binds in the ribosome at a site allosterically induced by interactions between the last 12 residues of the nascent TnaC peptide and the ribosomal exit tunnel (Seidelt et. al, *Science* 326, 1412-1415 (2009)). When this induced site is occupied by tryptophan, ribosomal release is inhibited and the Rho factor-binding site is thereby blocked.) When the Rho factor-binding site is blocked, transcription of tnaA and tnaB occurs. For our purposes, the key feature of this mechanism is that the translation of tnaC causes transcriptional elongation by RNA polymerase into the structural genes. This explicit translation-transcription coupling characteristic of the tna element forms the basis of our adapter.

FIG. 2. Mechanism for the tna leader-peptide element, a naturally occurring regulator of transcriptional elongation (i.e., translation-coupled regulator of transcription), from which an adapter (adapter TCRT) can be derived. The wild-type tna leader-peptide element's regulatory mechanism relies on the interaction between the last 12 residues of the leader peptide and the ribosome. This interaction causes a conformational change in the ribosome that creates a tryptophan-binding site. If this binding site is occupied by free tryptophan (in these examples, free tryptophan is always present), ribosomal release is inhibited. Therefore, if translation of the leader peptide initiates (Step 1) and the leader peptide is fully translated, the ribosome stalls over the natural stop codon of the leader peptide, blocking the adjacent rut site (Step 2). This prevents Rho factor-mediated transcriptional termination, thus allowing the continuation of RNA polymerase into the controlled genes (Step 3). If Rho factor binds to the rut site, transcription is terminated ("OFF"). RNA polymerase pauses at the depicted pause site until the ribosome invades structure II, facilitating kinetic coordination of mRNA transcription with leader peptide translation. Overlined nucleotides in bold correspond to the leader peptide's open reading frame (tnaC). SEQ ID NO: 14 is the sequence of nucleotides depicted in the Figure. SEQ ID NO: 38 includes the nucleotides of SEQ ID NO: 14 and further includes additional nucleotides not depicted in the figure.

The native RBS of tnaC is constitutively active and therefore full translation of tnaC always occurs; this means that in the presence of tryptophan, downstream genes are transcribed. However, we hypothesized that if one were to replace the native RBS of tnaC with a regulated RBS, one that has both ON and OFF states, then in the OFF state, tnaC translation would not initiate. As a result, the ribosome would never reach, much less obstruct, the Rho factor-binding site, and transcriptional termination would occur. Therefore, the fusion of any RBS-based regulator of translational initiation to the tna element should, in theory, yield a corresponding regulator of transcriptional elongation, with the tna element acting as an adapter between translational and transcriptional control (FIG. 3a).

An attenuator of transcriptional elongation. To test our adapter design, we first converted the IS10 translational initiation control system[23] into a regulator of transcriptional elongation. The IS10 system consists of a regulatory unit termed RNA-IN, a controlled gene whose translation initiates at an RBS within RNA-IN, and a trans-acting antisense RNA molecule termed RNA-OUT. When RNA-OUT is present in sufficient amounts, it binds to RNA-IN, forming a duplex that sequesters the RBS included in RNA-IN; as a result, translation cannot initiate.

To convert the IS 10 system into a regulator of transcriptional elongation, we fused RNA-IN to tnaC. This was achieved by removing the first 24 or 39 nucleotides of the tna element and inserting the 42 nucleotide RNA-IN unit[16] in their stead. Two fusions resulted: in the first (fusion 1), the complete tnaC coding region was retained; in the second (fusion 2), five N-terminal codons (this number corresponds to the five residues added by the coding fragment portion of the RNA-IN unit) were removed from the tnaC coding region such that the resulting fusion retained the length, though not identity, of wild-type tnaC. Fusion 1 and fusion 2 were then cloned upstream of a superfolder GFP reporter gene (Pedelacq et. al, *Nat. Biotech.* 24, 79-88 (2006)) including its own RBS, and the resulting constructs, placed under the control of a strong constitutive promoter, were inserted into low-copy plasmids to yield pCCL-036 and pCCL-037, respectively.

Figure 3A:
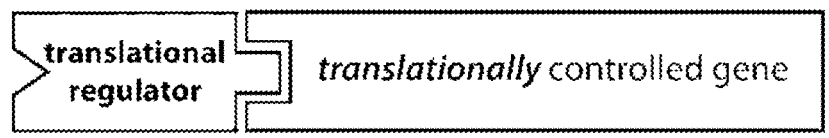
FIGS. 3A-C depict converting cis-regulators of translation into synthetic TCRTs.
Figure 3A:
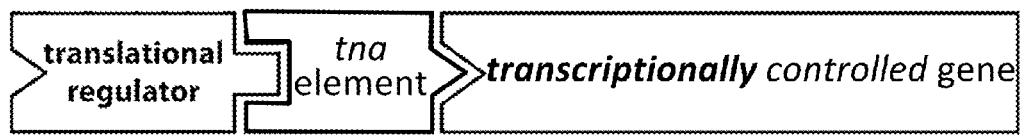
Figure 3B:
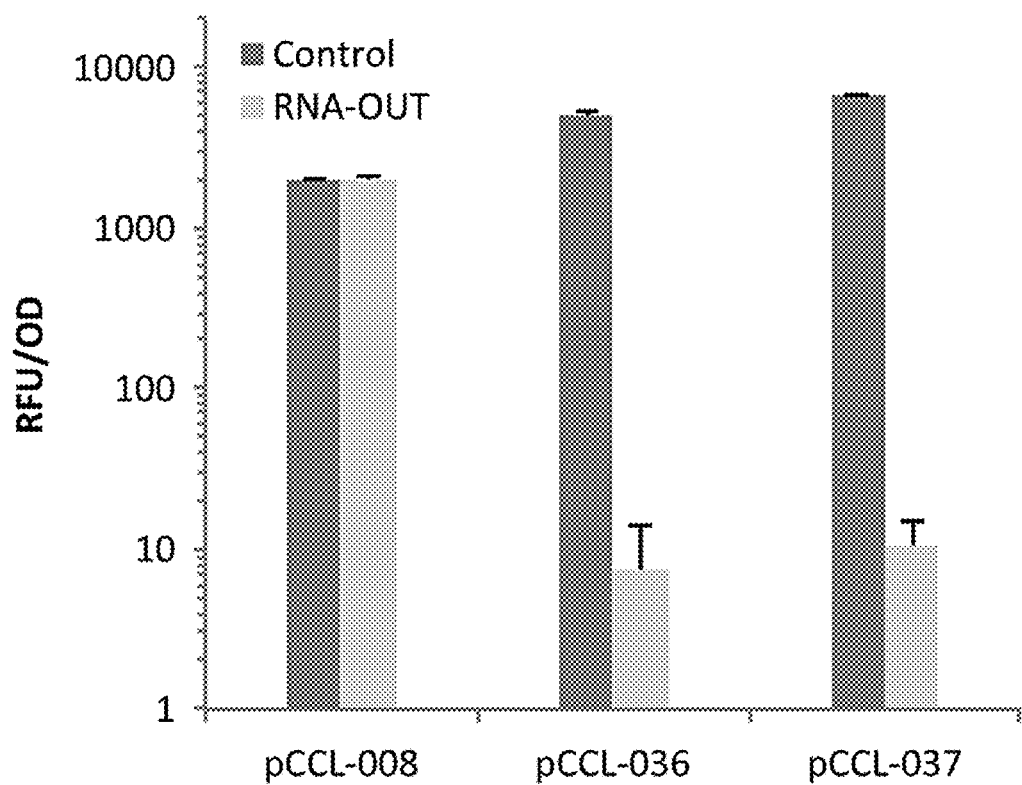
Figure 3B:
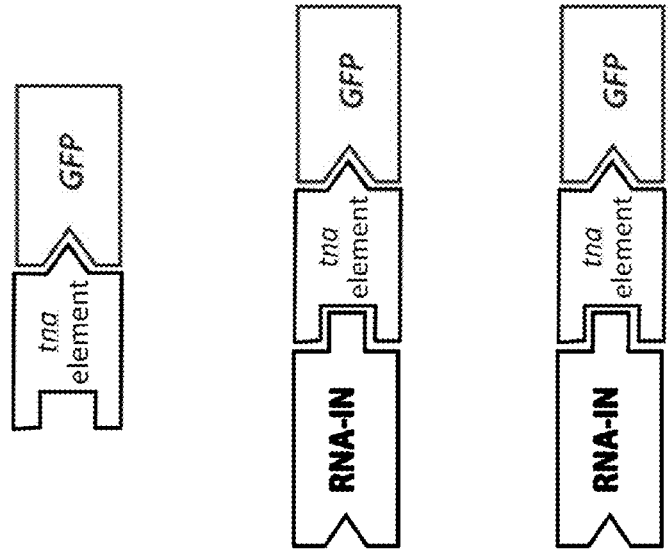
Figure 3C:
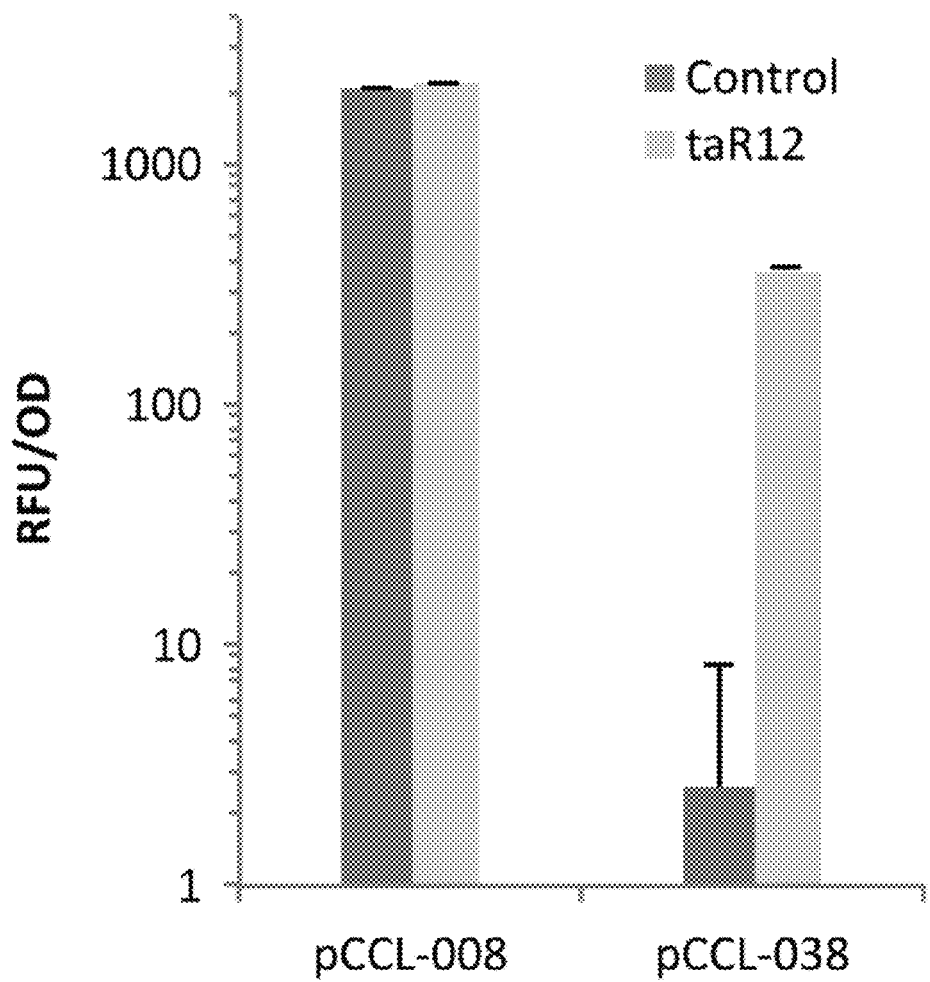

FIGS. 3A-C. Converting cis-regulators of translation into synthetic TCRTs. (a) Adapter strategy. The "translational regulator" in the figure is a cis-regulator of translation and the "tna element" in the figure an example of an adapter (adapter TCRT). A synthetic TCRT is produced by combining a cis-regulator of translation and an adapter TCRT. (b and c) Performance of antisense-mediated synthetic TCRTs achieved through conversion of the corresponding translational control systems into synthetic TCRTs. Fluorescence of cells comprising various plasmid pairs is shown. GFP expression is shown in background-subtracted relative fluorescence units (RFUs) normalized to optical density (OD); excitation at 485 nm, emission at 510 nm (n=3, error bars are ±s.d.). Background autofluorescence was determined by measuring the RFU/OD of similarly grown cells comprising plasmids pCCL-000 (a control plasmid that does not encode GFP) and pSLQ220k (a plasmid expressing no RNA-OUT). In these experiments, average background RFU/OD was measured to be 131.7 (in the same arbitrary units as graphed data). pCCL-008 is a positive control plasmid that includes GFP under the transcriptional regulation of the wild-type tna element. Data were collected using a fluorescence plate reader (see "Methods" section of the Examples). (b) Specific attenuation of transcription by RNA-OUT. Control refers to the presence of plasmid pSLQ220k, which expresses no antisense RNA; RNA-OUT refers to the presence of plasmid pSLQ214k, which expresses RNA-OUT. (c) Specific activation of transcription by taR12. Control refers to the presence of plasmid pSLQ220k, which expresses no antisense RNA; taR12 refers to the presence of plasmid pSLQtaR12k, which expresses taR12.

Figure 4A:
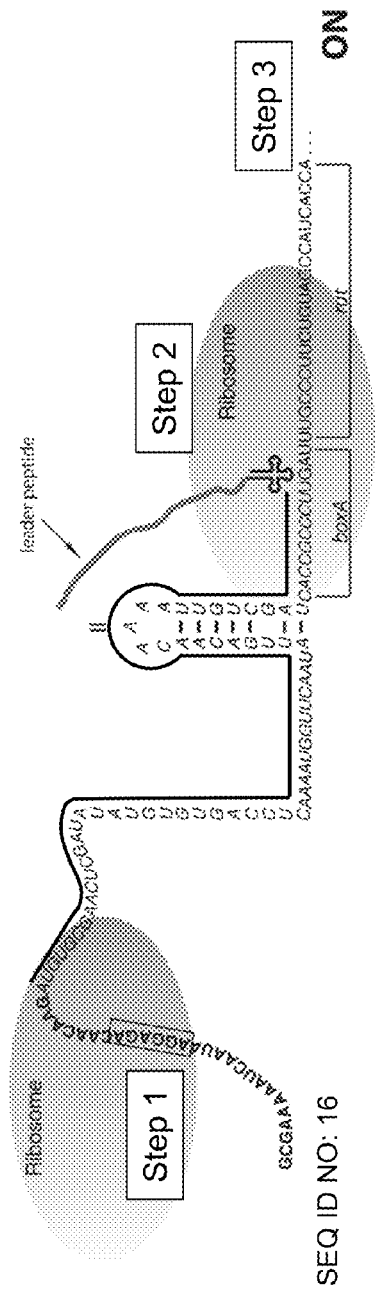
FIGS. 4A-F depict behavior of the IS 10 attenuator cis-regulator of translation converted into a synthetic TCRT (a synthetic attenuator TCRT).
Figure 4B:
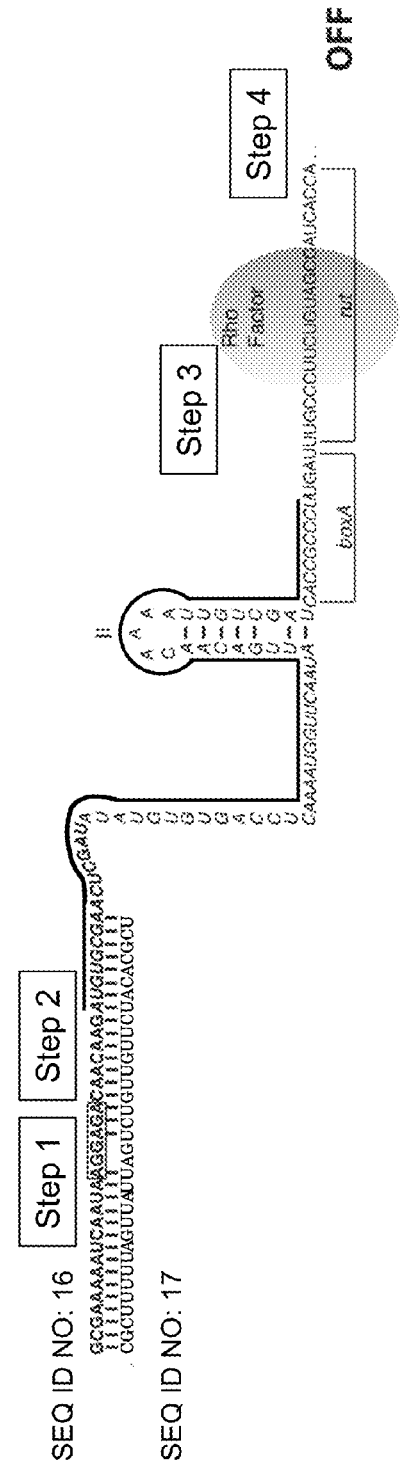

To test whether our converted regulators properly control the transcription of GFP, pCCL-036 and pCCL-037 were transformed into *E. coli* Top10 cells along with a second plasmid that expressed RNA-OUT under the control of a strong constitutive promoter or did not encode RNA-OUT. We found that cells comprising pCCL-036 or pCCL-037 in the absence of RNA-OUT showed strong fluorescence whereas cells comprising pCCL-036 or pCCL-037 in the presence of RNA-OUT showed minimal fluorescence (FIG. 3b). This is because in the absence of RNA-OUT, translation of the tnaC variants should be uninhibited, resulting in transcriptional elongation into the controlled GFP gene (FIG. 4a); and in the presence of RNA-OUT, translation of the tnaC variants should be inhibited, resulting in transcriptional termination before RNA polymerase transcribes the GFP gene (FIG. 4b). We further observed that the attenuation by RNA-OUT was unimodal (FIGS. 4c and 4d) and varies as a function of RNA-OUT concentration (FIGS. 4e and 4f). Taken together, these data demonstrate the successful conversion of the IS 10 translational initiation control system into a well-behaved regulator of transcriptional elongation using our adapter strategy.

Figure 4C:
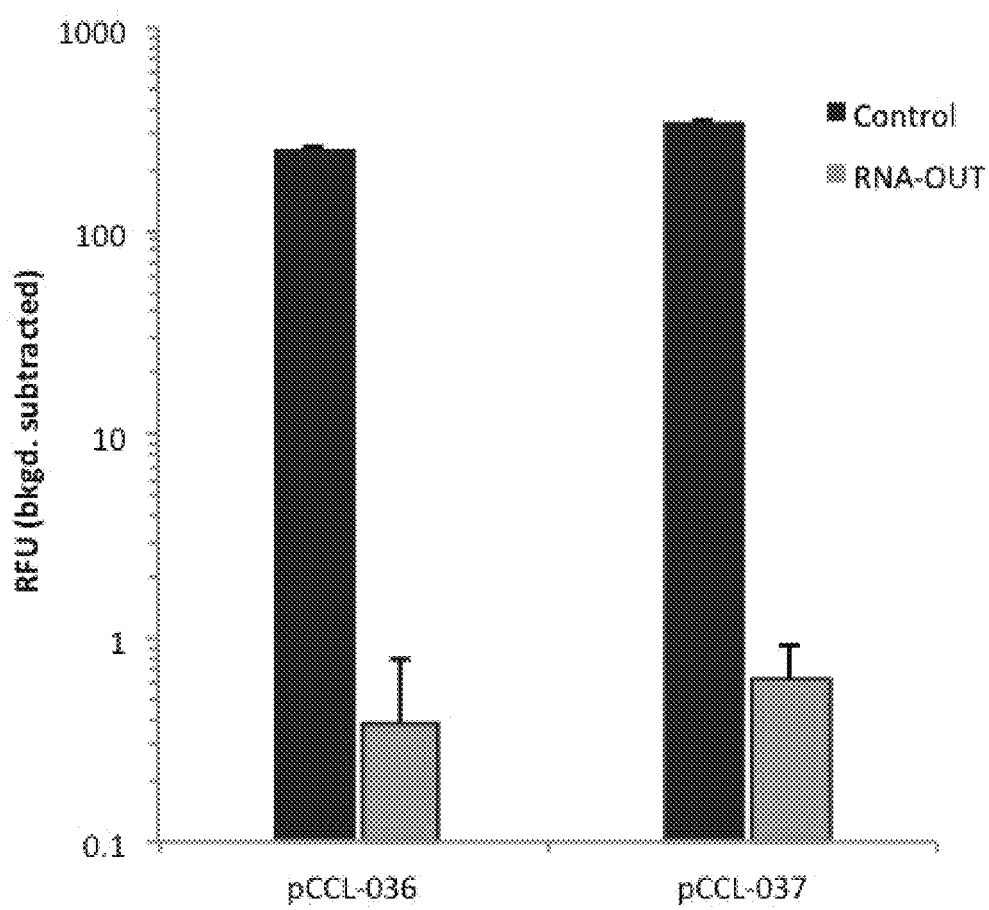
Figure 4D:
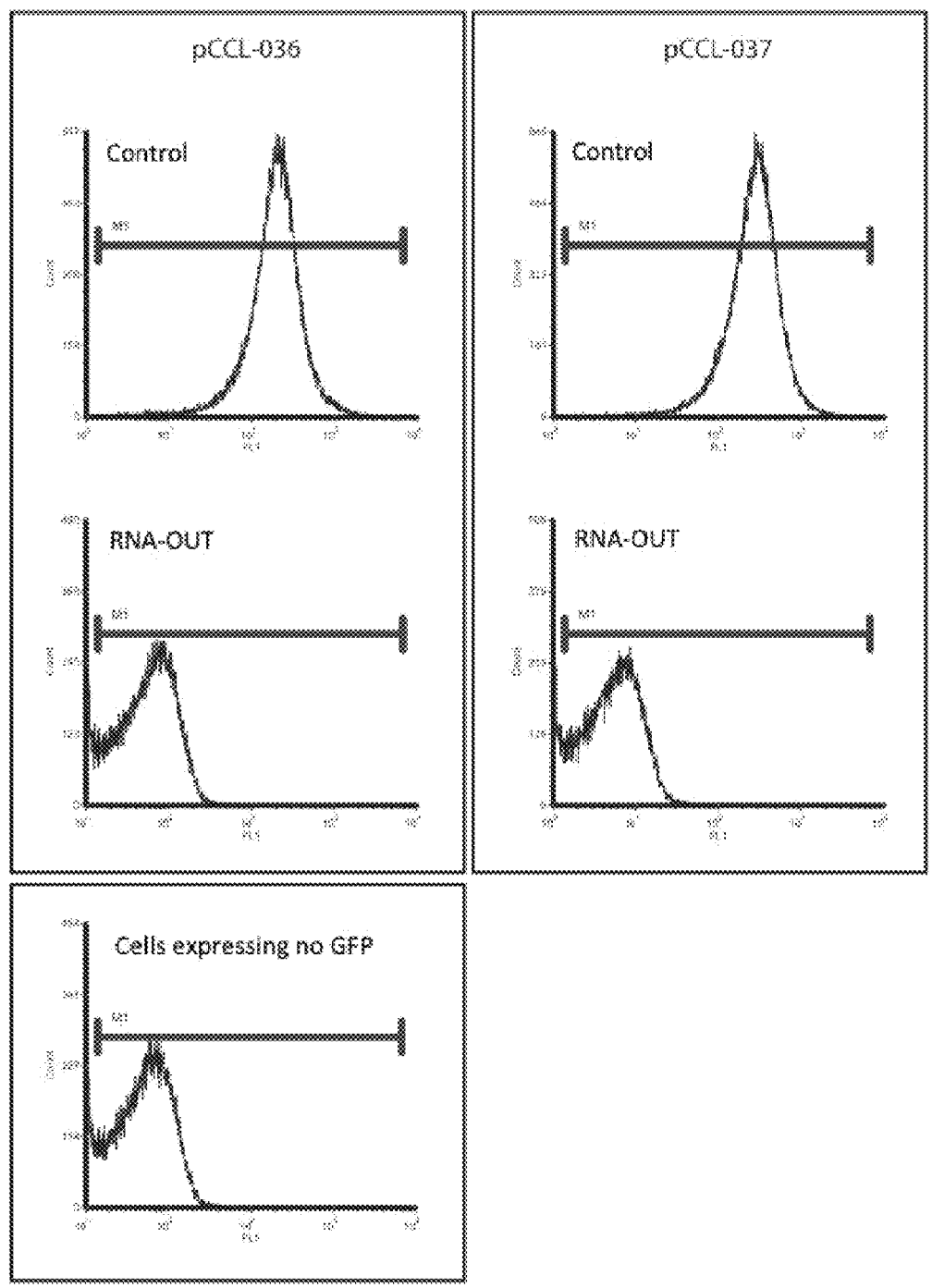
Figure 4E:
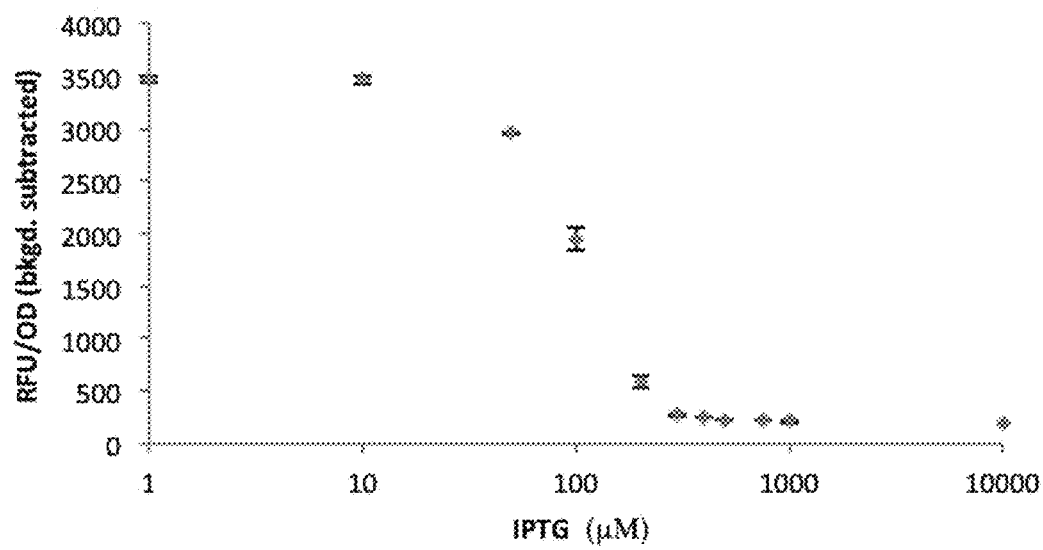
Figure 4F:
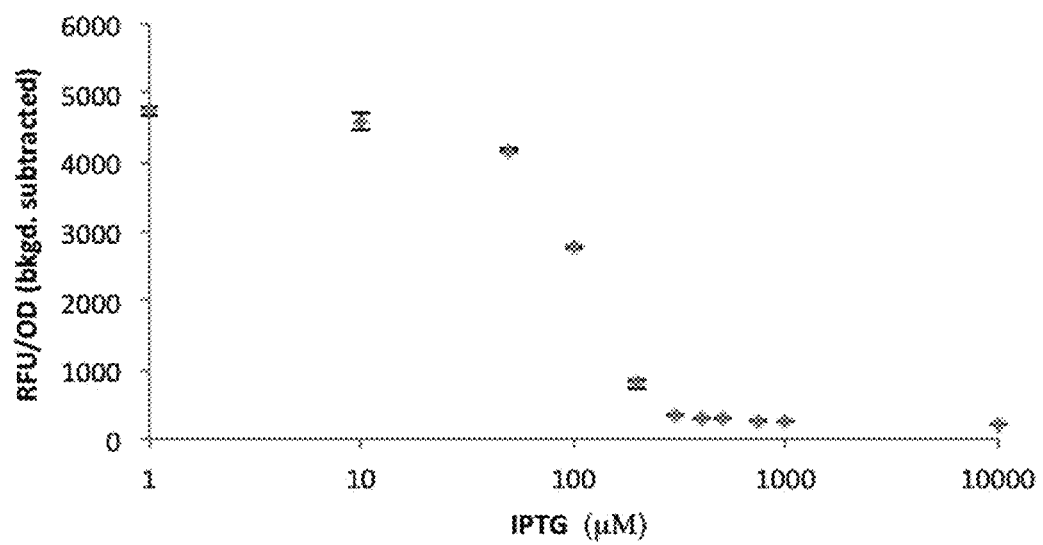

Our converted regulators are highly effective: in the presence of RNA-OUT, fluorescence is reduced to near-background levels (FIGS. 3b, 4c, and 4d). This is of note because one common criticism of RNA-based regulators is their low dynamic range compared to regulators based on protein-promoter interactions. In this case, it seems that conversion of the IS10 translational control system results in a regulator that rivals the efficiency of promoter-based transcriptional regulation while retaining the composability, modularity, and scalability that make RNA parts desirable.

An activator of transcriptional elongation. To complement our attenuator, we targeted the taRNA/crRNA translational activation system for conversion (Isaacs et. al, *Nat. Biotech.* 22, 841-847 (2004)). This system consists of a cis-regulator of translational initiation whose RBS is sequestered in a stem-loop structure (called crRNA), and a separate trans-activating RNA molecule (called taRNA) that can hybridize to part of the crRNA stem-loop to reveal the otherwise sequestered RBS. As a result, translation of a gene regulated by crRNA initiates in the presence of taRNA. We wished to convert this riboregulator of translational initiation into the corresponding riboregulator of transcriptional elongation. To do this, we fused crR12, a specific engineered crRNA (Isaacs et. al, *Nat. Biotech.* 22, 841-847 (2004)), to tnaC. This construct was then cloned upstream of a GFP reporter gene, placed under the control of a strong constitutive promoter, and inserted into a low-copy plasmid to yield pCCL-038.

FIGS. 4A-F. Behavior of the IS 10 attenuator cis-regulator of translation converted into a synthetic TCRT (a synthetic attenuator TCRT). Boxed nucleotides correspond to the RBS controlling initiation of leader peptide translation. Overlined nucleotides correspond to the open reading frame (in this case modified at the 5' end) of the leader peptide. Nucleotides (SEQ ID NO: 17) depicted as hybridizing to the leader peptide correspond to RNA-OUT. (a) RNA-OUT is absent. The RBS (boxed nucleotides) included in RNA-IN is free and the ribosome initiates translation (Step 1). The leader peptide is fully translated and the ribosome stalls over the natural stop codon of tnaC, blocking the adjacent rut site (Step 2). This prevents Rho factor-mediated transcriptional termination and RNA polymerase continues transcription into the controlled genes (Step 3). (b) RNA-OUT is present. The RBS included in RNA-IN is sequestered by RNA-OUT (Step 1). The ribosome cannot initiate translation (Step 2), and the leader peptide is not synthesized. The rut site is therefore free, allowing Rho factor mediated termination of the continuing RNA polymerase before it reaches controlled genes (Steps 3 and 4). (c and d) Performance of the converted IS10 system by flow cytometry. Bar graphs show background-subtracted mean GFP fluorescence in RFUs, averaged from the gated regions (horizontal bar) of cytometry histograms. Representative cytometry histograms are shown. Background autofluorescence was determined by measuring the mean fluorescence in RFUs of similarly grown cells comprising plasmid pCCL-000, a control plasmid that does not encode GFP, and pSLQ220k. In these experiments, average background RFU was measured to be 6.70 (in the same arbitrary units as graphed data). Experiments were conducted in triplicate (error bars are standard deviation) on the same day. (e and f) Induction of antisense RNAs. Fluorescence of cells comprising plasmid pairs is shown as a function of IPTG concentration. GFP expression is shown in background-subtracted relative fluorescence units (RFUs) normalized to optical density (OD); excitation at 485 nm, emission at 510 nm. Background autofluorescence was determined by measuring the RFU/OD of similarly grown cells comprising plasmid pCCL-000, a control plasmid that does not encode GFP, and pSLQ220k. In these experiments, average background RFU/OD was measured to be 209.4 (in the same arbitrary units as graphed data). Experiments were conducted in triplicate (error bars are standard deviation) on the same day. (e) Inducible attenuation of transcription by RNA-OUT. Cells comprise pCCL-036 and pTHSS-08. pTHSS-08 encodes RNA-OUT under the control of a lac promoter. (f) Inducible attenuation of transcription by RNA-OUT. Cells comprise pCCL-037 and pTHSS-08. SEQ ID NO: 16 is the sequence of nucleotides depicted in the longer polynucleotide in the Figure. SEQ ID NO: 39 includes the nucleotides of SEQ ID NO: 16 with additional nucleotides not shown in the figure. SEQ ID NO: 17 is the sequence of nucleotides depicted in the shorter polynucleotide in the Figure (corresponding to RNA-OUT). The full sequence of RNA-OUT is SEQ ID NO: 30.

Figure 5C:
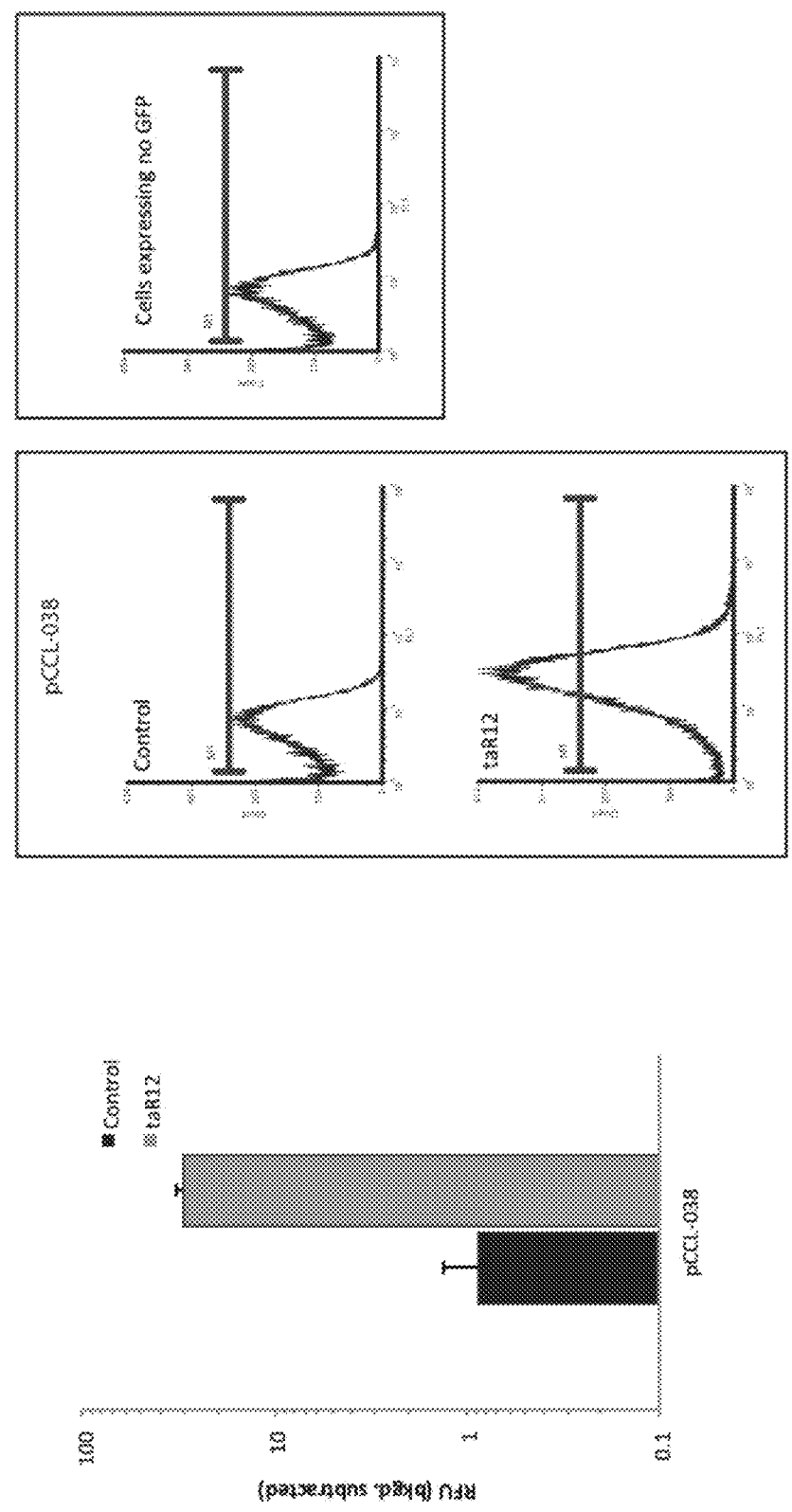
Figure 5D:
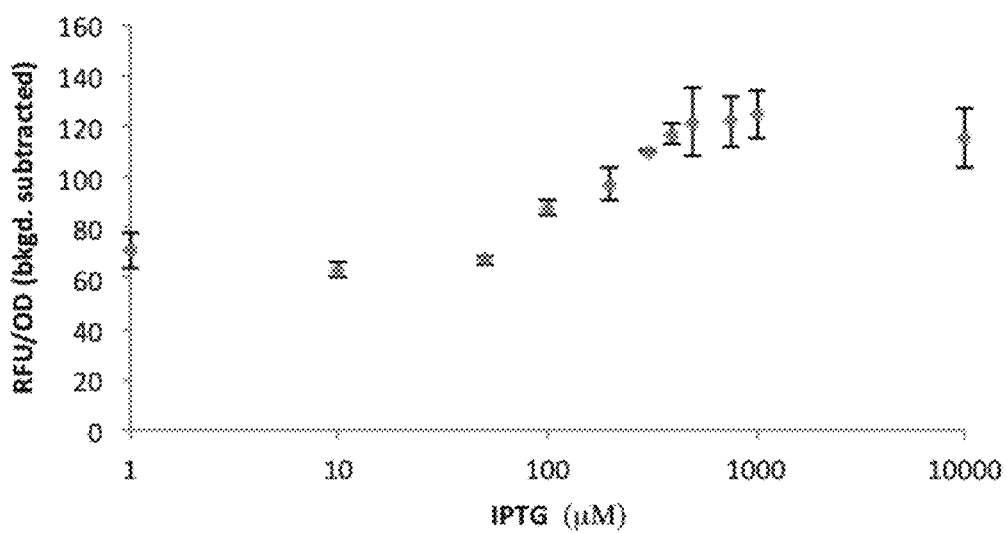

To test function, pCCL-038 was transformed into *E. coli* Top10 cells along with a second plasmid that expressed either taR12 (a specific engineered taRNA that targets crR12) under the control of a strong constitutive promoter, or no taR12. Cells comprising pCCL-038 but no taR12 showed minimal fluorescence (FIG. 3c), because in the absence of taR12, translation of tnaC cannot initiate, resulting in transcriptional termination before RNA polymerase reaches the GFP gene (FIG. 5a). In contrast, cells comprising pCCL-038 and taR12 showed high fluorescence (FIG. 3c), because taR12 binding reveals the RBS of the crR12-tnaC fusion, activating translation of tnaC and transcriptional elongation by RNA polymerase into the controlled GFP gene (FIG. 5b). The responses were unimodal (FIG. 5c), and varied with taR12 concentration (FIG. 5d). Taken together, these data demonstrate the successful conversion of the crR12/taR12 translational initiation control system into an effective RNA-mediated activator of transcriptional elongation.

FIGS. 5A-D. Behavior of the converted taRNA/crRNA activator cis-regulator of translation into a synthetic TCRT (a synthetic activator TCRT). (a and b) Desired behavior for the synthetic TCRT present in pCCL-038. Boxed nucleotides correspond to the RBS controlling translational initiation of tnaC (the leader peptide). Overlined nucleotides correspond to the leader peptide's open reading frame (tnaC). SEQ ID NO: 19 corresponds to taR12 (RNA-OUT). (a) taR12 is absent. The RBS included in crR12 is sequestered and the ribosome cannot initiate translation (Step 1). The leader peptide is not synthesized. The rut site is therefore free, allowing Rho factor mediated termination of the continuing RNA polymerase before it reaches controlled genes (Steps 2 and 3). (b) taR12 is present. taR12 binds to crR12 and frees the RBS included in crR12 (Steps 1 and 2). The leader peptide is fully translated and the ribosome stalls over the natural stop codon of tnaC, blocking the adjacent rut site (Step 3). This prevents Rho factor-mediated transcriptional termination and RNA polymerase continues transcription into the controlled genes (Step 4). (c) Performance of the converted taRNA/crRNA system by flow cytometry. Bar graphs show background-subtracted mean GFP fluorescence in RFUs, averaged from the gated regions (horizontal bar) of cytometry histograms. Representative cytometry histograms are shown. Background autofluorescence was determined by measuring the mean fluorescence in RFUs of similarly grown cells comprising plasmid pCCL-000, a control plasmid that does not encode GFP, and pSLQ220k. In these experiments, average background RFU was measured to be 6.70 (in the same arbitrary units as graphed data). Experiments were conducted in triplicate (error bars are ±standard deviation) on the same day. (d) Inducible activation of transcription by taR12. Cells comprise pCCL-038+ pTHSS-06. Fluorescence of cells comprising plasmid pairs is shown as a function of IPTG concentration. GFP expression is shown in background-subtracted relative fluorescence units (RFUs) normalized to optical density (OD); excitation at 485 nm, emission at 510 nm. Background autofluorescence was determined by measuring the RFU/OD of similarly grown cells comprising plasmid pCCL-000, a control plasmid that does not encode GFP, and pSLQ220k. In these experiments, average background RFU/OD was measured to be 209.4 (in the same arbitrary units as graphed data). Experiments were conducted in triplicate (error bars are ±standard deviation) on the same day. Data were collected using a fluorescence plate reader. SEQ ID NO: 18 is the sequence of nucleotides depicted in the longer polynucleotide in the Figure. SEQ ID NO: 41 includes the nucleotides of SEQ ID NO: 18 with additional nucleotides not shown in the figure. SEQ ID NO: 19 is the sequence of nucleotides depicted in the shorter polynucleotide in the Figure (corresponding to taR12). The full sequence of taR12 is SEQ ID NO: 29.

Mutually orthogonal regulators. Our lab recently developed a computational algorithm for the systematic prediction of orthogonal riboregulators based on the IS10 system. We use rationally designed variants of the RNA-IN/OUT antisense-RNA-mediated translation system from the insertion sequence IS10 to quantify >500 RNA-RNA interactions in *Escherichia coli*; integrate the dataset with sequence-activity modeling to identify thermodynamic stability of the duplex and seed region as key determinants of specificity. Applying this model, we predicted the performance of an additional ~2600 antisense-regulator pairs, forecasted the possibility of large families of orthogonal mutants, forward engineered and experimentally validated two RNA pairs orthogonal to an existing group of 5 from the training dataset.

Our translational regulators were derived from the copy number control element from the insertion sequence IS 10, wherein an antisense RNA (RNA-OUT) inhibits transposase expression. RNA-OUT base-pairs to the translation initiation region of the transposase mRNA (RNA-IN) thereby, repressing translation both by preventing ribosome binding and promoting transcript degradation. The 5' end of the unstructured, unstable sense RNA-IN is complementary to the top of the loop domain and one entire side of the stable RNA-OUT hairpin. The first three base-pairs between RNA-IN and RNA-OUT are G-C pairs and the strength of hybridization free energy in this GC rich region seems to be critical for effective antisense interaction and molecular specificity. We reasoned, therefore, that these specificity-determining interactions could be manipulated to create families of mutually-orthogonal variants of the native system. We use the term "orthogonal family" to describe a group of (>2 members) sense and antisense mutants that interact with their cognate partners and show negligible interaction with their non-cognate counterparts. Thus, an RNA-IN/RNA-OUT pair that interacts is "orthogonal" to a second RNA-IN/RNA-OUT pair when the two pairs to do not exhibit cross-talk (i.e., the non-cognate counterparts do not interact).

We identified a minimized and slightly modified regulatory region that is sufficient for >85% repression of target. To assess the performance of a RNA-IN/OUT pair, we measured the percent repression of RNA-IN mediated superfolder GFP (SFGFP) fluorescence (constitutively expressed from a low-copy plasmid) in presence of RNA-OUT (expressed from a high copy plasmid) in E. coli TOP10 cells during exponential growth. We observed graded tuning of target repression at different induction levels of antisense RNA and about 90% repression of SFGFP fluorescence when RNA-OUT was fully induced. Since this result agrees with previously reported data corresponding to much longer RNA-IN and RNA-OUT regions, we conclude that our minimized system retains the desired activity. We confirmed that our minimized system is sensitive to changes in antisense/sense specificity by examining a reported specificity-altering mutation.

To engineer mutually-orthogonal sense-antisense pairs, we considered complementary mutations at the five nucleotides (in all combinations) in the 5' specificity region of RNA-IN and the corresponding nucleotides in the loop of RNA-OUT. This led to a set of 32 mutations in sense RNA-IN and antisense RNA-OUT. We reasoned that the possible number of orthogonal pairs could also be increased by inserting nucleotides within the recognition motif of this system thereby 'scaling-up' the RNA-RNA interaction region. We therefore considered insertion of 2 extra nucleotides AT, GC, TA and CG between position 3 and 4 of RNA-IN (corresponding complementary nucleotides at positions 33 and 34 of RNA-OUT). We also hypothesized that compensatory mutations in the first 3 base pairs of the interaction region in these 'scaled-up' mutants would extend the number of orthogonal pairs and possibly improve regulatory efficiency. This resulted in 24 additional RNA-IN/OUT paired mutations for a total library size of 56. This number may be further increased by considering all possible combination of (single, double, etc.) nucleotide insertions with all different first 3 bp combinations.

Earlier studies had suggested that, the RNA-IN/OUT interaction is thermodynamically favored strand exchange from the imperfectly base-paired RNA-OUT hairpin to the perfectly base-paired RNA-IN/RNA-OUT duplex; Furthermore, our rationally constrained library of RNA-IN/RNA-OUT pairs was composed of mutants that have 5 bp variable sequence region surrounded by a common flanking sequence. We thus assumed that the specificity of interaction and repression efficiency in our library of mutants can be explained, to a large extent, by differences in their hybridization free energies. The orthogonal pairs would be expected to have lower hybridization energy than that between non-cognate pairs. To predict to the first order which pairs in our virtual library would show highest specificity of interaction and lowest cross-talk with other members, we estimated the hybridization free energies using the UNAfold software (Markham et al, Methods Mol Biol 453, 3-31, doi:10.1007/978-1-60327-429-6_1 (2008)) for all 56 sense/antisense pairs in the library (total 3136 interactions). As expected, we found that the cognate sense/antisense partners as a group along the diagonal showed far more stable hybrids compared to that of non-cognate partners. To maximize the chance of mutual orthogonality, we selected 23 candidates from the total of 56 library members via a clustering procedure. Only 5 RNA-OUT mutants out of the 23 conserve the YUNR motif, which also gave us a chance to test the importance of this motif in the functioning of the IN-OUT system.

Measurement and Analysis of the Mutant Library

We generated the 23 RNA-IN and RNA-OUT mutant constructs and cells bearing each of the 23 target RNA-IN plasmids were co-transformed with each of the plasmids expressing antisense RNA-OUT versions or a nonsense (control) RNA. The performance of RNA-IN/OUT pairs was quantified by measuring the fluorescence during the exponential phase of each strain and percentage repression was calculated. Most of cognate sense/antisense pairs showed very good repression (>80%). Approximately 5% of all pairs achieve more than 70% repression, while about 75% of total pairs show less than 20% repression. Overall, we observe a wide range of percent target repression ranging from negligible repression (<5%) to over 90% repression and dynamic range (ratio between target expression in absence of antisense RNA and maximal antisense RNA) of 1 to 10. We also find many examples of a single antisense RNA repressing multiple sense targets, and single sense targets recognized by multiple antisense RNAs. One intriguing result is that more than 70% of cognate pairs show a repression level higher than 75% and do not possess a YUNR motif in the antisense RNA species indicating that the YUNR motif is dispensable for the proper functioning of this system.

To determine how energetics of sense-antisense RNA interaction correlates with the experimental percentage repression, we plotted the calculated hybridization free energy for all 529 interactions against the experimental percentage repression. We observed that both cognate and non-cognate pair interactions with a free energy more than −41 kcal/mol are not active in repression, whereas most interactions with a free energy less than −46 kcal/mol showed stronger repression (closer to 85%). These results indicate that there is a critical threshold free energy needed for the propagation of initial pairing interaction to a stable duplex formation and thereby causing efficient repression of target mRNA. We did not observe a strong correlation between target repression and accessibility of recognition motif (unfolding free energy of sense and antisense RNA). This indicates that the applied mutational strategy may be interfering minimally with the structure of both interacting RNAs.

Validating the Orthogonality of Mutant Pairs

Using the experimentally determined percentage repression data to quantify target and non-target specificity, we can identify groups/families of RNA-IN/OUT variants expected to function orthogonally when placed in the same cell. Further, identifying non-cognate partners that show significant cross-talk, aids in determining base-pairing features that impart the promiscuity. Thus, the definition of mutual orthogonality depends on thresholds of repression (% R) and cross-reactivity percentages (% C) for cognate and non-cognate pairs respectively that we deem acceptable for a specific application.

At 80% R and 10% C we have more than 10 families of mutually orthogonal pairs and triplets, and one family of 4 orthogonal mutants, whereas at 20% C, we have more than 20 families made up of 2, 3 and 4 mutually orthogonal mutants and 5 families of 5 mutants. To test if the orthogonality and repression profile of these mutants is retained with a sequence-divergent gene-of-interest, we fused five mutually orthogonal sense mutants to mRFP1 (52% sequence identity) and assayed them in the presence of corresponding antisense RNAs. The observed percentage repressions were quantitatively equivalent to that of SFGFP, demonstrating the modularity of the sense region and efficiency of antisense RNA. To demonstrate the mutual orthogonality among members of orthogonal family in the same cell we picked five sense-antisense pairs for further characterization. Here, the sense partner of each pair was translationally fused to either to SFGFP or mRFP1 and repression was quantified in the presence of different combinations of the cognate antisense RNAs expressed from a different plasmid. The results support that our library produced a significant number of mutually orthogonal and modular regulatory variants that retain their specificity characteristics within the same cell.

Selection of a Sequence-Function Relationship Model

The correlation between the hybridization free energy and percent repression suggests that free energy is a good though not a perfect predictor of interaction specificity. To find other features that determine the specificity of interaction between RNA-IN and RNA-OUT we pursued modeling of sequence-function relationship for the in vivo experimental dataset.

Based on prior work and inspection of the predicted RNA secondary structures and the form of the duplex, we selected a short list of 31 possible features that might explain the observed patterns of repression. To formally select the most significant feature explaining the repression data, we applied Partial Least Squares Regression with stepwise feature selection and outlier detection. The analysis, after detecting 8 outliers (out of 529 interactions), identified just two features that explain 86% variation in the data after 10 fold cross validation: the hybridization energies of the entire 37 bp interaction region and a duplex seed region of 5 bps. The model suggests that that the initial nucleation event at the GC rich 5 bp seed region and the subsequent helix progression is thermodynamically driven and determines the efficient repression of the target mRNA. These results recapitulate early studies that pointed out the importance of the 5 bp interaction region in determining the copy number control performance of RNA-IN/OUT system.

Validation of Model Predictions

To validate the predictive capability of the model and forward engineer new orthogonal mutants we used the model to predict % R for all 56 mutant pairs we initially considered. This yielded a total of 3136 percentage repression predictions including the 529 experimentally tested pairs. We estimated the total possible number of mutually orthogonal pairs in the 56 RNA-IN and OUT variants from these predictions for different family sizes at different thresholds of % R and % C. At 80% R and 10% C we have more than 300 families of mutually orthogonal pairs, triplets and quadruplets, more than 150 families of 5 mutants and 10 families of 6 orthogonal mutants. While at 20% C we have more than thousand families made up of 3, 4, 5 and 6 mutually orthogonal mutants and about 166 families of 7 mutants.

To experimentally validate a subset of these predictions, we forward engineered two sense and antisense RNA pairs (mutant #13 and mutant #40) predicted to have a desired strong % R and insignificant cross-talk with the experimentally discovered family of 5 orthogonal pairs, thus expanding the number of orthogonal families. We characterized these four forward engineered mutants in the presence of their cognate and non-cognate partners totaling more than 50 interactions. As predicted, sense and antisense mutant 13 and 40 yielded an altered/expanded family made up of 6 and 5 mutually orthogonal mutants respectively. The sense and antisense mutant 13 showed specific interaction with each other while showing negligible crosstalk with 5 non-cognate partners. Similarly, sense and antisense mutant 40 showed negligible crosstalk with 4 non-cognate partners and specific interaction with each other. In addition to these orthogonality validations, the experimental results clearly demonstrate the ability of the model to reliably and quantitatively predict a wide range of percentage repression displayed by more than 50 interactions. This tool thus provides a powerful avenue to rationally design and forward engineer new orthogonal members to an existing mutually-orthogonal RNA-IN/OUT pair family.

Figure 6A:
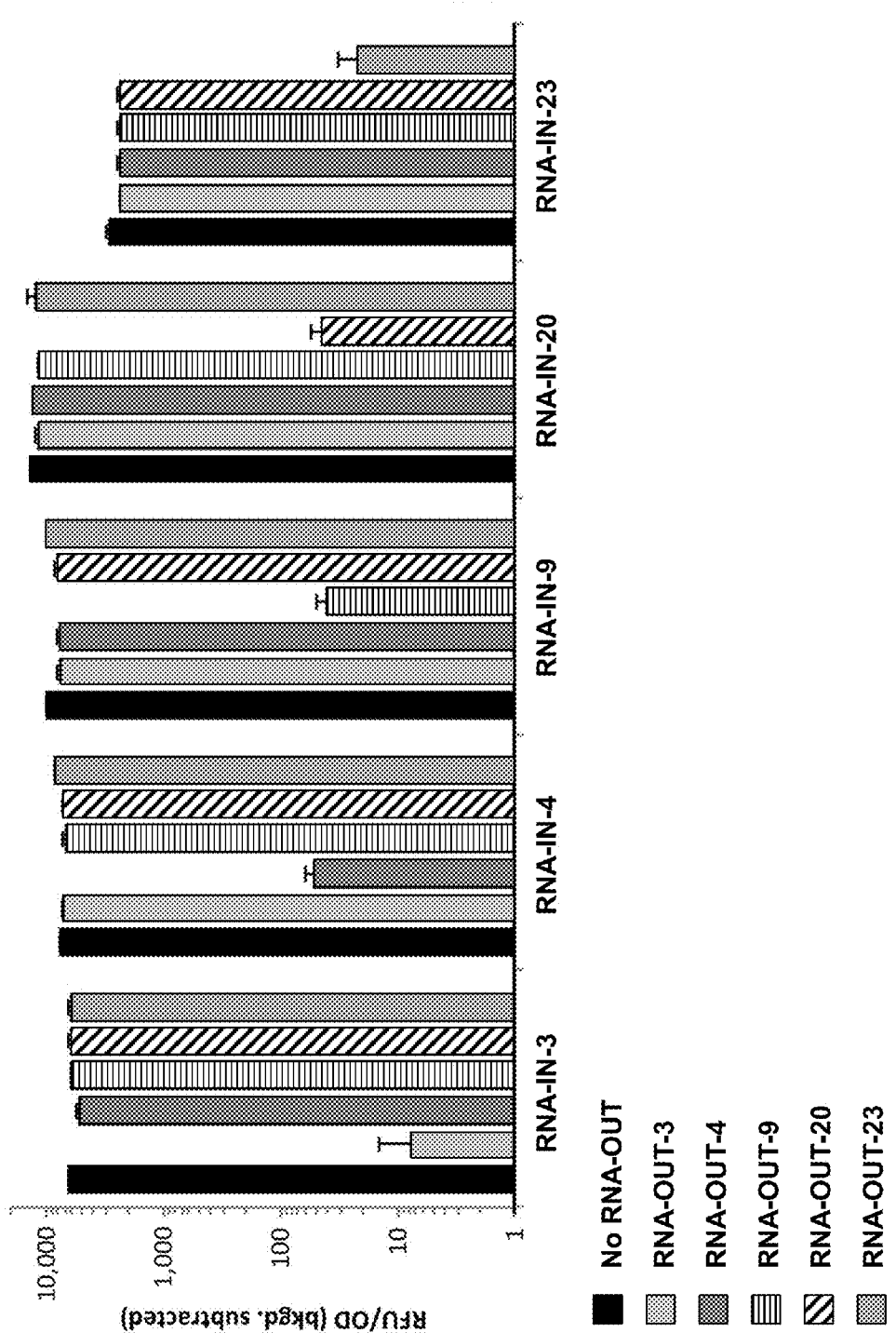
Figure 6B:
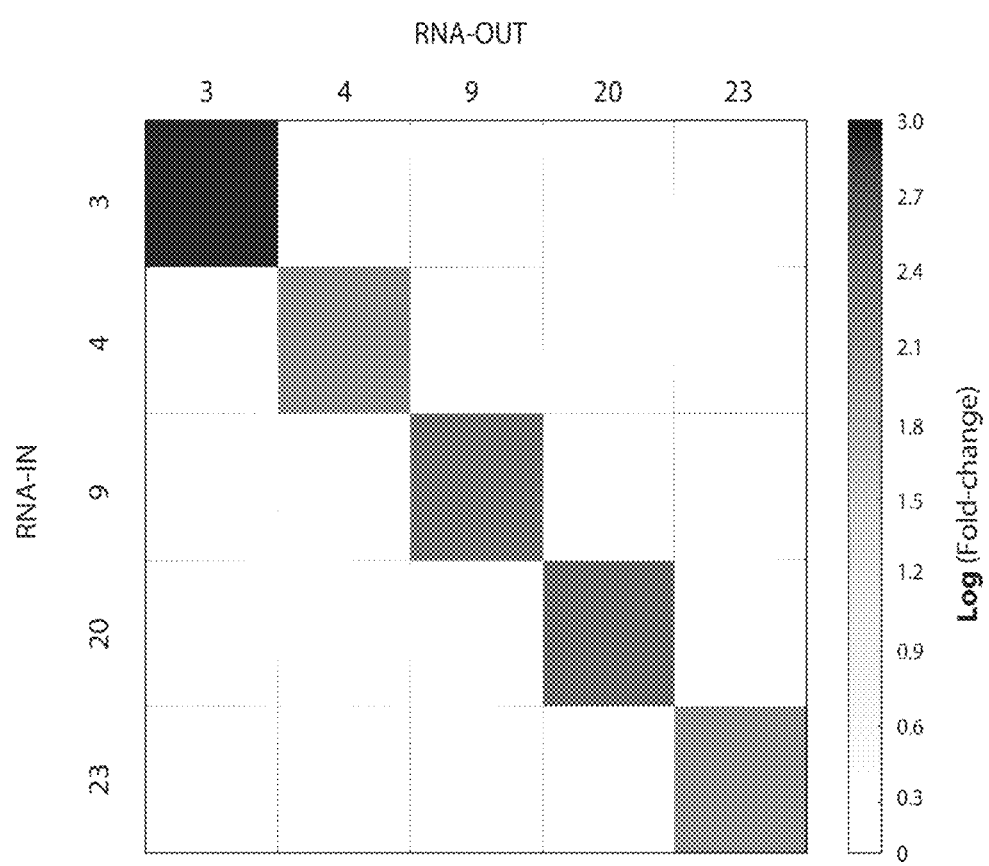

However, the resulting orthogonal regulator sets control translational initiation. In order to extend their regulatory versatility, we sought to use our adapter to achieve libraries of mutually orthogonal transcriptional regulators. To do this, five mutually orthogonal variants of RNA-IN were fused to tnaC following the same construction as pCCL-037. The resulting plasmids were cotransformed into E. coli Top10 cells in conjunction with plasmids expressing RNA-OUT variants. For cells that included cognate RNA-IN/RNA-OUT pairs, dramatic attenuation of GFP expression was observed in all five cases; for cells comprising non-cognate RNA-IN/RNA-OUT pairs, little to no attenuation of GPF expression was observed for all 20 possibilities (FIGS. 6a and 6b). We note that although these mutually orthogonal regulators are variants of the same parent RNA-IN/RNA-OUT pair, there are clear differences in their regulatory properties, as is the case for the original unconverted regulators. For example, the ON level for variant 23 is substantially lower than the ON levels for the other pairs (FIG. 6a). In addition, variant 3 displays more effective repression than the others. Nonetheless, our adapter yields a set of highly effective and mechanistically homogenous mutually orthogonal transcriptional attenuators.

FIGS. 6A and 6B. Performance of five mutually orthogonal antisense-mediated synthetic TCRTs achieved through conversion of the corresponding cis-regulator of translation (translational control systems). RNA-IN-3, 4, 9, 20, and 23 are mutually orthogonal RNA-IN variants that respond to RNA-OUT-3, 4, 9, 20, and 23. Control refers to the presence of plasmid pSLQ220k, which expresses no antisense RNA. RNA-IN variants controlling the expression of GFP are encoded on plasmids pCCL-IN-3, pCCL-IN-4, pCCL-IN-9, pCCL-IN-20, and pCCL-IN-23; RNA-OUT variants are expressed from plasmids pSLQ-OUT-3, pSLQ-OUT-4, pSLQ-OUT-9, pSLQ-OUT-20, and pSLQ-OUT-23. Fluorescence of cells comprising various plasmid pairs is shown. GFP expression is shown in background-subtracted relative fluorescence units (RFUs) normalized to optical density (OD); excitation at 485 nm, emission at 510 nm (n=3, error bars are ±s.d.). Background autofluorescence was determined by measuring the RFU/OD of similarly grown cells comprising plasmids pCCL-000 (a control plasmid that does not encode GFP) and pSLQ220k (a plasmid expressing no RNA-OUT). In these experiments, average background RFU/OD was measured to be 159.0 (in the same arbitrary units as graphed data). Data were collected using a fluorescence plate reader. (a) Attenuation of transcription in the presence of RNA-OUTs. (b) Heat map showing mutually orthogonal behavior. Fold-change is the ratio of background-subtracted RFUs between each RNA-IN/RNA-OUT pair and the corresponding RNA-IN/control pair.

Composition of orthogonal regulators into NOR gates. Regulators of transcriptional elongation can be composed into logics and higher-order function simply through tethering (Lucks et. al, Proc. Natl. Acad. Sci. USA 108, 8617-8622 (2011)). To demonstrate this feature, we constructed a collection of NOR gates that integrate two, three, or four inputs by tethering together two, three, or four of our mutually orthogonal converted RNA-IN variants.

In constructing these NOR gates, we needed first to address the issue that RNA-IN variants require a flexible 5'-terminus for proper function (Kittle et. al, RNA. J. Mol. Biol. 210, 561-572 (1989)). Therefore, we used a strategy in which CRISPR repeats are inserted between linked RNA-IN variants such that once transcribed, a free 5'-terminus is generated through cleavage by a coexpressed Csy4 protein (Qi et. al, *Nat. Biotech.*, in press)). This allows the full regulatory decision of the $N^{th}$ regulator to be made before the $(N+1)^{th}$ regulatory unit can be transcribed. The resulting NOR gate compositions were cloned upstream of GFP, which acted as our reporter.

As shown in FIG. 7, the NOR gates exhibited the correct behaviors. For example, the two-input NOR gates consisting of tandem RNA-IN variants were ON in the absence of the corresponding plasmid-encoded cognate RNA-OUTs, and OFF in the presence of either cognate RNA-OUTs. Likewise, the three-input gate exhibited attenuation only in the presence of any of its three cognate RNA-OUTs and the four-input gate exhibited attenuation in the presence of any of its four cognate RNA-OUTs. In addition, these responses were unimodal, as evident in the fluorescence microscopy (FIG. 7) and cytometry studies. Finally, to ensure that RNA-OUT variants do not interfere with each other when multiple variants are simultaneously expressed, we also tested our three two-input NOR gates in the presence of both cognate RNA-OUTs. We observed attenuation of fluorescence in these cases as well (FIG. 7). Therefore, our converted regulators are indeed predictably composable through tethering, yielding, in this case, a large number of synthetic NOR gates.

Figure 7A:
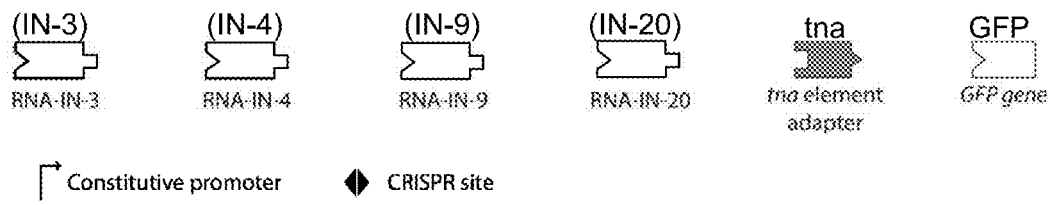
FIGS. 7A-C depict behavior of NOR gates assembled from mutually orthogonal attenuator cis-regulators of translation converted into synthetic attenuator TCRTs.
Figure 7B:
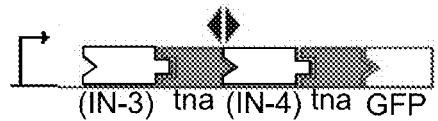
Figure 7B:
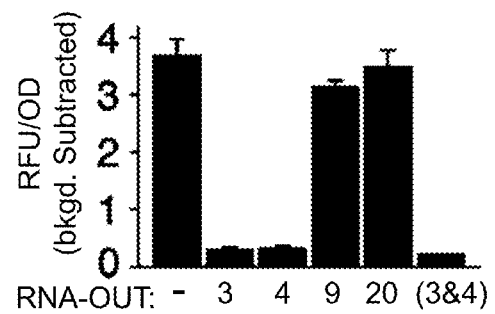
Figure 7B:
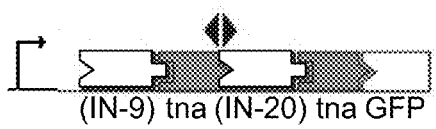
Figure 7B:
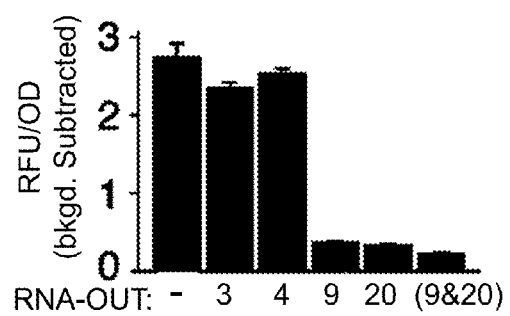
Figure 7B:
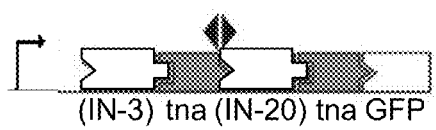
Figure 7B:
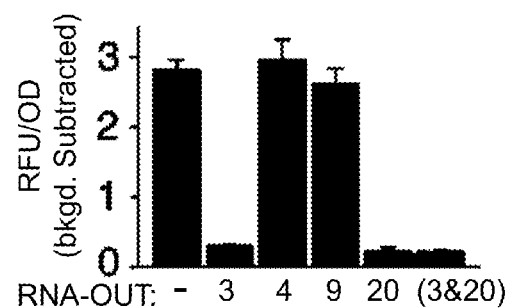
Figure 7C:
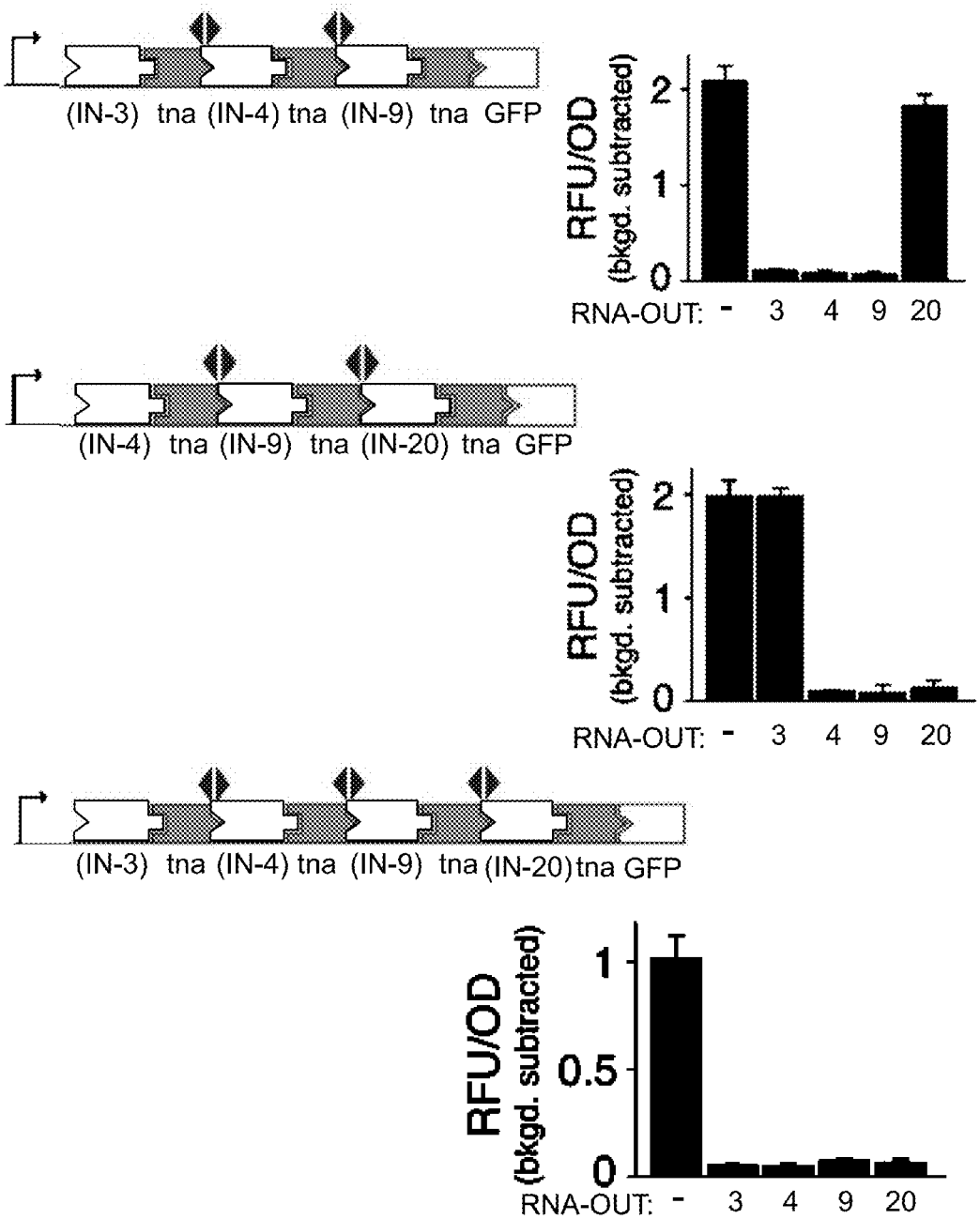

FIGS. 7A-C. Behavior of NOR gates assembled from mutually orthogonal attenuator cis-regulators of translation converted into synthetic attenuator TCRTs. (a) components used to assemble NOR gates included cis-regulators of translation (RNA-IN 3, 4, 9, and 20), an adapter TCRT (tna element) and a nucleotide sequence of interest (encoding GFP). (b)(c) Fluorescence microscopy images of cells comprising various plasmid pairs are shown. Bar graphs represent GFP expression from bulk culture, shown in background-subtracted relative fluorescence units (RFUs) normalized to optical density (OD); excitation at 485 nm, emission at 510 nm (n=3, error bars are ±s.d.). The scale shown corresponds to raw RFU/OD values×$10^{-3}$. Background autofluorescence was determined by measuring the RFU/OD of similarly grown cells comprising pSLQ213 (a control plasmid that does not encode GFP). In these experiments, average background RFU/OD was measured to be 0.24 (in the same arbitrary units as graphed data). Bar graph data were collected using a fluorescence plate reader.

Integration of additional inputs (Riboswitch aptamers). Many synthetic RBS-based regulators of translational initiation respond to engineered antisense RNA molecules. To extend the range of inputs beyond RNA, one may create "riboswitch-like" functional fusions between RNA aptamers and antisense RNAs such that when the aptamer's cognate ligand is bound, the function of the antisense RNA triggered or disrupted. Recently, this strategy has been demonstrated for the IS 10 system, where the semi-rational fusion of a theophylline aptamer to RNA-OUT results in a chimeric molecule that is active only when the aptamer is bound by theophylline (Qi et. al, *Nucleic Acids Res.* 2012 July; 40(12): 5775-86. Epub 2012 Mar. 1). Specifically, the unbound aptamer domain forms a disruptive pseudoknot with the RNA-OUT domain, which is untied when theophylline binds the aptamer; this allows RNA-OUT to hybridize with RNA-IN and repress translational initiation. We hypothesized that by using such aptamer-RNA-OUT variants with our converted regulators, we could control transcriptional elongation with new inputs (FIG. 8a).

To test this, we transformed pCCL-037 into *E. coli* Top10 cells alongside a second plasmid (pSLQ528) that constitu-tively expresses a functional theophylline-aptamer-RNA-OUT fusion (theo-P-IS10 ncRNA fusion (SEQ ID NO: 43); Qi et. al, *Nucleic Acids Res.* 2012 July; 40(12):5775-86. Epub 2012 Mar. 1). We observed strong fluorescence from cells grown in the absence of theophylline but substantially reduced fluorescence from cells grown in the presence of theophylline (FIG. 8b). This is because when theophylline is present, it restores the activity of the RNA-OUT domain, allowing it to bind RNA-IN and inhibit translation of tnaC. By virtue of the adapter's mechanism, this results in transcriptional termination before RNA polymerase reaches the GFP gene, yielding a regulator of transcriptional elongation that responds to theophylline. As expected, cells comprising pCCL-037 and a second plasmid without RNA-OUT (pSLQ220k) were fluorescent with or without theophylline and cells comprising pCCL-000, which does not encode GFP, displayed minimal fluorescence with or without theophylline (FIG. 8b).

Figure 8A:
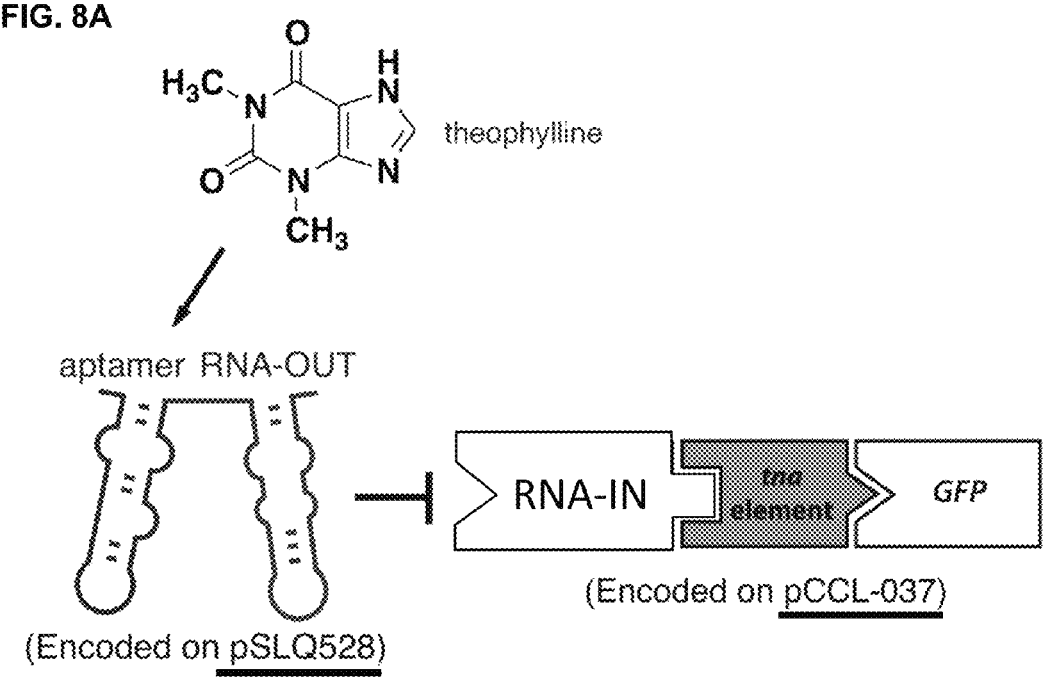
FIGS. 8A and 8B depict behavior of a theophylline-controlled transcriptional regulator.
Figure 8B:
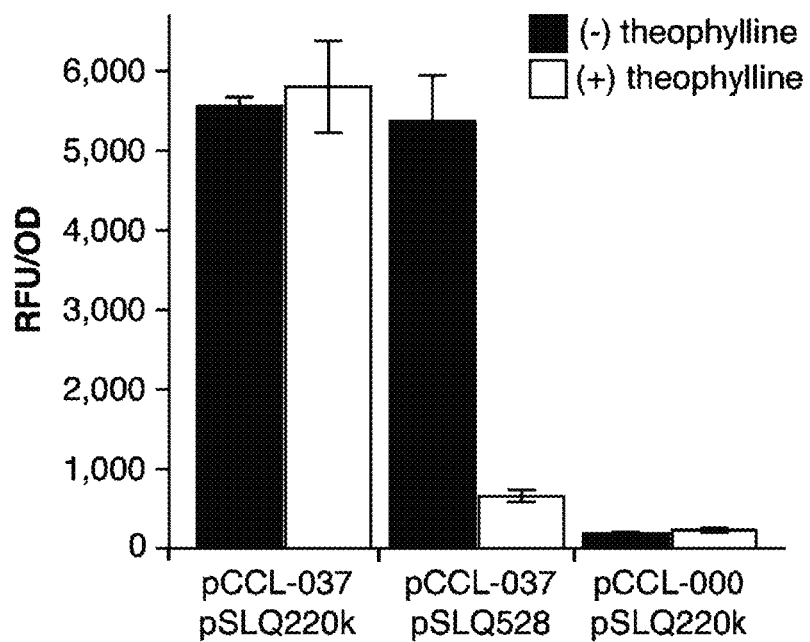

FIGS. 8A and 8B. Behavior of a theophylline-controlled transcriptional regulator. (a) Transcriptional control by a theophylline-triggered aptamer-RNA-OUT fusion. (b) Specific attenuation of transcription by theophylline (2.5 mM). The theophylline-aptamer-RNA-OUT fusion is expressed from plasmid pSLQ528. GFP expression is shown in relative fluorescence units (RFUs) normalized to optical density (OD) without background subtraction; excitation at 485 nm, emission at 510 nm (n=3, error bars are ±s.d.). pSLQ220k is a plasmid expressing no RNA-OUT and pCCL-000 is a plasmid that does not encode GFP. Data were collected using a fluorescence plate reader.

Structural analysis. Our adapter relies on the wholesale replacement of tnaC's native RBS (and associated upstream context) with a desired regulator of translational initiation. Since the wild-type tna element is composed of two hairpins, the first of whose stem includes the native RBS of tnaC, this wholesale replacement could be problematic if hairpin I's structure is essential (Cruz-Vera et. al, *J. Bacteriol.* 191, 7001-7006 (2009)). Inversely, if hairpin I's structure is unessential, then our adapter should be general. Given that all our attempts at conversion, including the 8 presented here, have been successful, we believe the latter to be the case.

To explore this further, we conducted structural studies on the tna element and our engineered variants using selective 2'-hydroxyl acylation analyzed by primer extension (SHAPE)(Low et. al, *Methods* 52, 150-158 (2010); Merino et. al, *J. Am. Chem. Soc.* 127, 4223-4231 (2005); Mortimer et. al, *J. Am. Chem. Soc.* 129, 4144-4145 (2007); and Mortimer et. al, *Nat. Protocols* 4, 1413-1421 (2009)). In brief, RNAs corresponding to the wild-type tna element and the engineered variants present in pCCL-036 (RNA-IN-tnaC fusion), pCCL-037 (RNA-IN-tnaC fusion), and pCCL-038 (crR12-tnaC fusion) were produced via runoff transcription and treated with a general acylation reagent that reacts preferentially at flexible nucleotides. Since acylation of 2'-hydroxyls renders nucleotides incapable of continued extension by reverse transcriptase during the following primer extension step, the frequency and length of the resulting cDNA products map the RNA secondary (and to some extent tertiary) structures. Reactivity data generated in this manner were used to calculate pseudo-free energies that were combined with RNA structural prediction algorithms to yield SHAPE-informed secondary structures for the wild-type and variant tna elements.

Figures 9A, 9B:
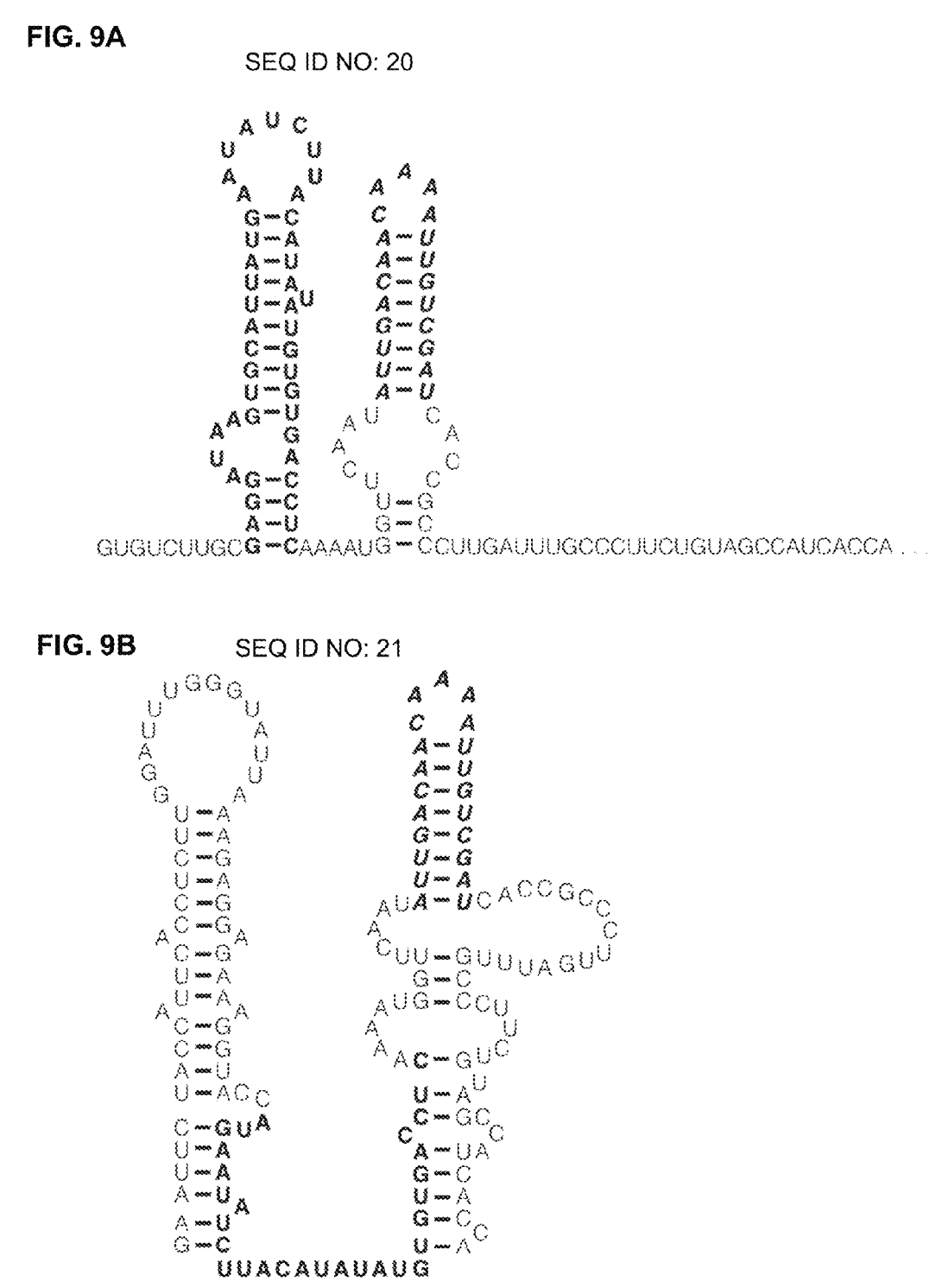
Figure 9C:
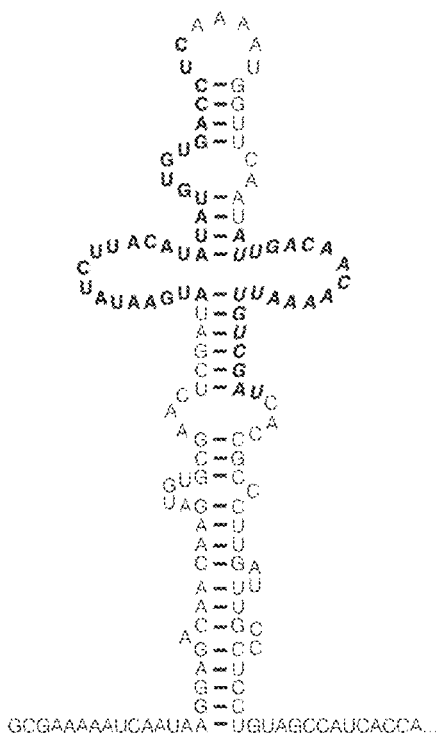
Figure 9D:
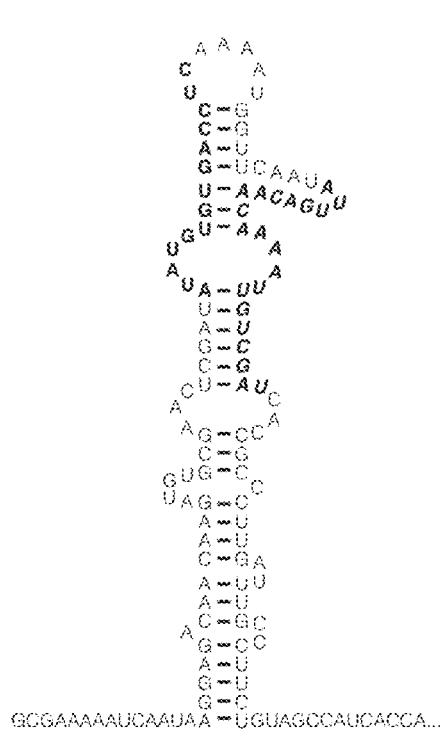

In agreement with previous predictions (Cruz-Vera et. al, *J. Bacteriol.* 191, 7001-7006 (2009)), the SHAPE-informed structure of the wild-type tna element shows the presence of two hairpins, I and II (FIG. 9a). In the engineered tna variants including fusions to RNA-IN or crR12, hairpin I is disrupted (FIGS. 9b, 9c, and 9d). Since these variants are still functional, we conclude that regulators of translational initiation can be fused to tnaC without regard for maintaining hairpin I's structure, suggesting that our conversion strategy is general. This is further supported by the observation that the crR12 unit, while disrupting hairpin I, maintains its RBS-sequestering hairpin structure, demonstrating that important structural features of the regulatory system being attached to our adapter are retained (FIG. 9b).

More broadly, our SHAPE-informed structures reveal that the tnaC coding region and sequences corresponding to hairpins I and II of the wild-type tna element adopt different structures in our various engineered transcriptional regulators; yet all these regulators function well. This implies that the tna element has minimal dependence on RNA secondary structure and may not require much more than the last 12 residues of TnaC and their ability to induce ribosomal stalling over a Rho factor-binding site in the presence of tryptophan (Gong et. al, *Science* 297, 1864-1867 (2002); Gong et. al, *Proc. Natl. Acad. Sci. USA* 98, 8997-9001 (2001); and Seidelt et. al, *Science* 326, 1412-1415 (2009)). This lack of stringent or numerous structural dependencies implies that the range of regulators of translational initiation that can be fused to tnaC is large, rendering our adapter strategy highly general.

FIGS. 9A-D. SHAPE-informed structures of synthetic TCRTs achieved through conversion of the corresponding translational control systems. Nucleotides in bold correspond to hairpin I of the wild-type tna element's predicted RNA secondary structure. Nucleotides in bold and italics correspond to hairpin II of the wild-type tna element's predicted RNA secondary structure. (a) Wild-type tna element. (b) Variant tna element with tnaC under cis-translational regulation by crR12. This synthetic TCRT is used in pCCL-038. (c) Variant tna element with a tnaC variant under cis-translational regulation by RNA-IN. This synthetic TCRT is used in pCCL-036. (d) Variant tna element with a truncated tnaC variant under cis-translational regulation by RNA-IN. This synthetic TCRT is used in pCCL-037.

As shown above, it has been demonstrated that mutually orthogonal RNA-IN/OUT variants can be systematically generated and converted into families of mutually orthogonal transcriptional regulators. These converted regulators can then be systematically composed into universal NOR logic gates that take RNA inputs and control RNA production. Taken together, this provides a scalable platform for the NOR-gate-based assembly of multi-layered circuits, all within a single cell. Second, tethered regulators of transcriptional elongation integrate sequential regulatory events into an overall decision and therefore should exhibit predictable behaviors across a number of properties beyond the demonstrated Boolean logics. For example, we observed a decrease in the relative ON levels of our NOR gates as the number of linked attenuators increased (FIG. 7). This is because in the ON state, there is still some transcriptional attenuation due to imperfect timing for the translation-transcription coupling in the tna element or incomplete ribosomal stalling over the Rho factor-binding site. Therefore, as multiple regulators are linked, the inefficiency of the ON state compounds, leading to a reduction of total output. Though this effect is a limitation in some cases, it can be an advantage in others. For example, in our two-input NOR gates, we observed that attenuation in the presence of both cognate RNA-OUTs is more effective than attenuation in the presence of either cognate RNA-OUT alone (FIG. 7), as the probability of leakage is reduced when two attenuators, arranged in tandem, are both present. In general, the predictability of these composition effects is highly advantageous, as they may be exploited to tune absolute levels of expression, dynamic ranges, and transfer function forms through composition alone. Third, the ability to combine aptamers with RNA regulators should, in theory, extend the input range of our transcriptional regulators to any desired molecular input. Finally, the functional robustness of the tna element adapter, as evidenced by our SHAPE studies, allows its application to the gamut of natural and synthetic RBS-based translational regulators. This leads to a dramatic expansion in the number of independent regulators of transcriptional elongation available to 5'-UTR engineering, ones that through simple composition can yield signal integration and higher-order functions for predictable biological design.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed:

1. A nucleic acid construct comprising a synthetic translation-coupled regulator of transcription (TCRT) comprising in a 5' to 3' order:
   (a) a cis-regulator of translation that is a RNA-IN variant having a nucleotide sequence selected from the group consisting of SEQ ID NOs: 24-28: and
   (b) an adapter TCRT,
   wherein (a) and (b) are operably linked so that the transcription of sequences that are 3' of and operably linked to the synthetic TCRT is regulated by (a).

2. The nucleic acid construct of claim 1, further comprising a nucleic acid sequence of interest that is positioned 3' of the synthetic TCRT and is operably linked to the synthetic TCRT such that the synthetic TCRT regulates transcription of the nucleic acid sequence of interest.

3. The nucleic acid construct of claim 2, wherein the nucleic acid sequence of interest comprises a sequence selected from the group consisting of: an insertion site, a sequence encoding a polypeptide, a sequence encoding a sense RNA, a sequence encoding an antisense RNA, a sequence encoding a ribonucleic acid aptamer responsive to an environmental cue, and a sequence encoding an RNA that is responsive to an intracellular or environmental cue.

4. The nucleic acid construct of claim 3, wherein the environmental cue is selected from the group consisting of: a nucleic acid, a protein, a metabolite, pH, temperature, and combinations thereof.

5. The nucleic acid construct of claim 1, wherein the adapter translation-coupled regulator of transcription comprises in a 5' to 3' order:
   (a) a polynucleotide encoding the peptide tnaC;
   (b) a stop codon; and
   (c) a Rho utilization site (rut).

6. The nucleic acid construct of claim 1, wherein the synthetic translation-coupled regulator of transcription (TCRT) has the formula: (AB)x,
   wherein:
   (i) A is the cis-regulator of translation;
   (ii) B is the adapter TCRT;
   (iii) x is the number of repeated AB units;
   (iv) x is any integer;
   (v) each instance of A can be the same or different cis-regulator of translation as any previous instance of A; and (vi) each instance of B can be the same or different adapter TCRT as any previous instance of B.

7. A recombinant prokaryotic cell comprising the nucleic acid construct of claim 1.

8. The recombinant prokaryotic cell of claim 7, wherein the cell comprises two or more of the nucleic acid constructs of claim 1, wherein at least two of the cis-regulators of translation are orthogonal.

9. The recombinant prokaryotic cell of claim 8, wherein all of the cis-regulators of translation are orthogonal.

10. The recombinant prokaryotic cell of claim 7, wherein the cell further comprises a polynucleotide that encodes a nucleic acid that binds to the cis-regulator of translation of said nucleic acid construct.

11. The recombinant prokaryotic cell of claim 10, wherein the nucleic acid that binds to the cis-regulator of translation is a taRNA.

12. The recombinant prokaryotic cell of claim 11, wherein the taRNA is taR12 having a sequence of SEQ ID NO: 29.

13. The recombinant prokaryotic cell of claim 10, wherein the nucleic acid that binds to the cis-regulator of translation is an RNA-OUT having the sequence of SEQ ID NO: 30 or an RNA-OUT variant having a sequence selected from the group consisting of: SEQ ID NO: 31, SEQ ID NO: 32, SEQ ID NO: 33, SEQ ID NO: 34, and SEQ ID NO: 35.

14. A method of controlling transcription of a nucleic acid sequence comprising inducing, in a cell comprising the nucleic acid construct of claim 2, the cis- regulator of translation.

15. The method of claim 14, wherein inducing is performed by contacting the cell with a nucleic acid that binds to the cis-regulator of translation of the nucleic acid construct.

16. A kit comprising:
(A) the nucleic acid construct of claim 2; and
(B) a regulatory input molecule, or a nucleic acid construct encoding a regulatory input molecule, that regulates the synthetic TCRT.

* * * * *

SEQUENCE LISTING

```
<160> NUMBER OF SEQ ID NOS: 153

<210> SEQ ID NO 1
<211> LENGTH: 72
<212> TYPE: DNA
<213> ORGANISM: Artificial sequence
<220> FEATURE:
<223> OTHER INFORMATION: Synthetic nucleic acid sequence

<400> SEQUENCE: 1
ggccactagt gcgaaaaatc aataaggaga caacaagatg tgcgaactcg atatgaatat      60
cttacatata tg                                                          72

<210> SEQ ID NO 2
<211> LENGTH: 20
<212> TYPE: DNA
```

```
<213> ORGANISM: Artificial sequence
<220> FEATURE:
<223> OTHER INFORMATION: Synthetic nucleic acid sequence

<400> SEQUENCE: 2
cttcagcacg cgtcttgtag                                                    20

<210> SEQ ID NO 3
<211> LENGTH: 75
<212> TYPE: DNA
<213> ORGANISM: Artificial sequence
<220> FEATURE:
<223> OTHER INFORMATION: Synthetic nucleic acid sequence

<400> SEQUENCE: 3
ggccactagt gcgaaaaatc aataaggaga caacaagatg tgcgaactcg atatatgtgt        60
gacctcaaaa tggtt                                                         75

<210> SEQ ID NO 4
<211> LENGTH: 80
<212> TYPE: DNA
<213> ORGANISM: Artificial sequence
<220> FEATURE:
<223> OTHER INFORMATION: Synthetic nucleic acid sequence

<400> SEQUENCE: 4
ggccactagt gaattctacc attcacctct tggatgggta ttaaagagga gaaaggtacc        60
atgaatatct tacatatatg                                                    80

<210> SEQ ID NO 5
<211> LENGTH: 80
<212> TYPE: DNA
<213> ORGANISM: Artificial sequence
<220> FEATURE:
<223> OTHER INFORMATION: Synthetic nucleic acid sequence

<400> SEQUENCE: 5
ggccactagt gaattctacc attcacctct tggatgggta ttaaagagga gaaaggtacc        60
atgaatatct tacatatatg                                                    80

<210> SEQ ID NO 6
<211> LENGTH: 24
<212> TYPE: DNA
<213> ORGANISM: Artificial sequence
<220> FEATURE:
<223> OTHER INFORMATION: Synthetic nucleic acid sequence

<400> SEQUENCE: 6
ccgagctagc tcagtcctag gtat                                               24

<210> SEQ ID NO 7
<211> LENGTH: 25
<212> TYPE: DNA
<213> ORGANISM: Artificial sequence
<220> FEATURE:
<223> OTHER INFORMATION: Synthetic nucleic acid sequence

<400> SEQUENCE: 7
ccgaggatcc tctagagata tatgg                                              25

<210> SEQ ID NO 8
<211> LENGTH: 33
<212> TYPE: DNA
<213> ORGANISM: Artificial sequence
```

```
<220> FEATURE:
<223> OTHER INFORMATION: Synthetic nucleic acid sequence

<400> SEQUENCE: 8
taatatacta gtagagagcg ttcaccgaca aac                                    33

<210> SEQ ID NO 9
<211> LENGTH: 34
<212> TYPE: DNA
<213> ORGANISM: Artificial sequence
<220> FEATURE:
<223> OTHER INFORMATION: Synthetic nucleic acid sequence

<400> SEQUENCE: 9
taatatagat cttaccgctg ttgagatcca gttc                                   34

<210> SEQ ID NO 10
<211> LENGTH: 32
<212> TYPE: DNA
<213> ORGANISM: Artificial sequence
<220> FEATURE:
<223> OTHER INFORMATION: Synthetic nucleic acid sequence

<400> SEQUENCE: 10
tataattcta gagtcacact ggctcacctt cg                                     32

<210> SEQ ID NO 11
<211> LENGTH: 33
<212> TYPE: DNA
<213> ORGANISM: Artificial sequence
<220> FEATURE:
<223> OTHER INFORMATION: Synthetic nucleic acid sequence

<400> SEQUENCE: 11
taatatggat ccttgagagt tttcgccccg aag                                    33

<210> SEQ ID NO 12
<211> LENGTH: 60
<212> TYPE: DNA
<213> ORGANISM: Artificial sequence
<220> FEATURE:
<223> OTHER INFORMATION: Synthetic nucleic acid sequence

<400> SEQUENCE: 12
tgaaaattaa cttactacta ccatatatct ctagaggatc caaactcgag taaggatctc       60

<210> SEQ ID NO 13
<211> LENGTH: 60
<212> TYPE: DNA
<213> ORGANISM: Artificial sequence
<220> FEATURE:
<223> OTHER INFORMATION: Synthetic nucleic acid sequence

<400> SEQUENCE: 13
ttaaccacca ctaccaatca cctcctggat ttgggttgtg ctcagtatct tgttatccgc       60

<210> SEQ ID NO 14
<211> LENGTH: 123
<212> TYPE: RNA
<213> ORGANISM: Artificial sequence
<220> FEATURE:
<223> OTHER INFORMATION: Synthetic nucleic acid sequence

<400> SEQUENCE: 14
gugucuugcg aggauaagug cauuaugaau aucuuacaua uaugugugac cucaaaaugg       60
```
uucaauauug acaacaaaau ugucgaucac cgcccuugau uugcccuucu guagccauca    120
cca                                                                 123

<210> SEQ ID NO 15
<211> LENGTH: 99
<212> TYPE: RNA
<213> ORGANISM: Artificial sequence
<220> FEATURE:
<223> OTHER INFORMATION: Synthetic nucleic acid sequence

<400> SEQUENCE: 15
augaauaucu uacauauaug ugugaccuca aaaugguuca auauugacaa caaaauuguc    60
gaucaccgcc cuugauuugc ccuucuguag ccaucacca                          99

<210> SEQ ID NO 16
<211> LENGTH: 126
<212> TYPE: RNA
<213> ORGANISM: Artificial sequence
<220> FEATURE:
<223> OTHER INFORMATION: Synthetic nucleic acid sequence

<400> SEQUENCE: 16 gcgaaaauc aauaaggaga caacaagaug ugcgaacucg auauaugugu gaccucaaaa     60
ugguucaaua uugacaacaa aauugucgau caccgcccuu gauugcccu ucuguagcca    120 ucacca                                                              126

<210> SEQ ID NO 17
<211> LENGTH: 35
<212> TYPE: RNA
<213> ORGANISM: Artificial sequence
<220> FEATURE:
<223> OTHER INFORMATION: Synthetic nucleic acid sequence

<400> SEQUENCE: 17
ucgcacaucu uguugucuga uuauugauuu uucgc                              35

<210> SEQ ID NO 18
<211> LENGTH: 151
<212> TYPE: RNA
<213> ORGANISM: Artificial sequence
<220> FEATURE:
<223> OTHER INFORMATION: Synthetic nucleic acid sequence

<400> SEQUENCE: 18
gaauucuacc auucaccucu uggauuuggg uauuaaagag gagaaaggua ccaugaauau    60
cuuacauaua ugugugaccu caaaaugguu caauauugac aacaaaauug ucgaucaccg    120
cccuugauuu gcccuucugu agccaucacc a                                  151

<210> SEQ ID NO 19
<211> LENGTH: 58
<212> TYPE: RNA
<213> ORGANISM: Artificial sequence
<220> FEATURE:
<223> OTHER INFORMATION: Synthetic nucleic acid sequence

<400> SEQUENCE: 19
acccaaaucc aggaggugau ugguaguggu gguuaaugaa aauuaacuua cuacuacc     58

<210> SEQ ID NO 20
<211> LENGTH: 123
<212> TYPE: RNA
<213> ORGANISM: Artificial sequence

```
<220> FEATURE:
<223> OTHER INFORMATION: Synthetic nucleic acid sequence

<400> SEQUENCE: 20
gugucuugcg aggauaagug cauuaugaau aucuuacaua uaugugugac cucaaaaugg    60
uucaauauug acaacaaaau ugucgaucac cgcccuugau uugcccuucu guagccauca   120
cca                                                                 123

<210> SEQ ID NO 21
<211> LENGTH: 151
<212> TYPE: RNA
<213> ORGANISM: Artificial sequence
<220> FEATURE:
<223> OTHER INFORMATION: Synthetic nucleic acid sequence

<400> SEQUENCE: 21
gaauucuacc auucaccucu uggauuuggg uauuaaagag gagaaaggua ccaugaauau    60
cuuacauaua ugugugaccu caaaauggu caauauugac aacaaaauug ucgaucaccg   120
cccuugauuu gcccuucugu agccaucacc a                                  151

<210> SEQ ID NO 22
<211> LENGTH: 141
<212> TYPE: RNA
<213> ORGANISM: Artificial sequence
<220> FEATURE:
<223> OTHER INFORMATION: Synthetic nucleic acid sequence

<400> SEQUENCE: 22
gcgaaaaauc aauaaggaga caacaagaug ugcgaacucg auaugaauau cuuacauaua    60
ugugugaccu caaaauggu caauauugac aacaaaauug ucgaucaccg cccuugauuu   120
gcccuucugu agccaucacc a                                             141

<210> SEQ ID NO 23
<211> LENGTH: 126
<212> TYPE: RNA
<213> ORGANISM: Artificial sequence
<220> FEATURE:
<223> OTHER INFORMATION: Synthetic nucleic acid sequence

<400> SEQUENCE: 23
gcgaaaaauc aauaaggaga caacaagaug ugcgaacucg auauaugugu gaccucaaaa    60
ugguucaaua uugacaacaa aauugucgau caccgcccuu gauuugcccu ucuguagcca   120
ucacca                                                              126

<210> SEQ ID NO 24
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 24
gccaaaaauc aauaaggaga caacaagaug ugcgaacucg au                       42

<210> SEQ ID NO 25
<211> LENGTH: 42
<212> TYPE: RNA
<213> ORGANISM: Artificial sequence
<220> FEATURE:
<223> OTHER INFORMATION: Synthetic nucleic acid sequence
```

```
<400> SEQUENCE: 25
gcguaaaauc aauaaggaga caacaagaug ugcgaacucg au                         42

<210> SEQ ID NO 26
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 26
ggcuuaaauc aauaaggaga caacaagaug ugcgaacucg au                         42

<210> SEQ ID NO 27
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 27
ggguaaaaaa ucaauaagga caacaaga ugugcgaacu cgau                         44

<210> SEQ ID NO 28
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 28
ccccgaaaaa ucaauaagga gacaacaaga ugugcgaacu cgau                       44

<210> SEQ ID NO 29
<211> LENGTH: 71
<212> TYPE: RNA
<213> ORGANISM: Artificial sequence
<220> FEATURE:
<223> OTHER INFORMATION: Synthetic nucleic acid sequence

<400> SEQUENCE: 29
acccaaaucc aggaggugau ugguaguggu gguuaaugaa aauuaacuua cuacuaccau      60
auaucucuag a                                                          71

<210> SEQ ID NO 30
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 30
ucgcacaucu uguugucuga uuauugauuu uucgcgaaac cauuugauca uaugacaaga      60
uguguaucca ccuuaacuua augauuuuua ccaaaaucau aggggauuc aucag           115

<210> SEQ ID NO 31
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 31
ucgcacaucu uguugucuga uuauugauuu uuggcgaaac cauuugauca uaugacaaga      60
```
uguguaucca ccuuaacuua augauuuuua ccaaaaucau uaggggauuc aucag        115

<210> SEQ ID NO 32
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 32
ucgcacaucu uguugucuga uuauugauuu uacgcgaaac cauuugauca uaugacaaga    60
uguguaucca ccuuaacuua augauuuuua ccaaaaucau uaggggauuc aucag        115

<210> SEQ ID NO 33
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 33
ucgcacaucu uguugucuga uuauugauuu aagccgaaac cauuugauca uaugacaaga    60
uguguaucca ccuuaacuua augauuuuua ccaaaaucau uaggggauuc aucag        115

<210> SEQ ID NO 34
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 34
ucgcacaucu uguugucuga uuauugauuu uuuacccgaa accauuugau cauaugacaa    60
gauguguauc caccuuaacu uaaugauuuu uaccaaaauc auuagggau ucaucag       117

<210> SEQ ID NO 35
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 35
ucgcacaucu uguugucuga uuauugauuu uucggggaa accauuugau cauaugacaa    60
gauguguauc caccuuaacu uaaugauuuu uaccaaaauc auuagggau ucaucag       117

<210> SEQ ID NO 36
<211> LENGTH: 55
<212> TYPE: RNA
<213> ORGANISM: Artificial sequence
<220> FEATURE:
<223> OTHER INFORMATION: Synthetic nucleic acid sequence

<400> SEQUENCE: 36
gaauucuacc auucaccucu uggauuuggg uauuaaagag gagaaaggua ccaug        55

<210> SEQ ID NO 37
<211> LENGTH: 42
<212> TYPE: RNA
<213> ORGANISM: Artificial sequence
<220> FEATURE:
<223> OTHER INFORMATION: Synthetic nucleic acid sequence

```
<400> SEQUENCE: 37
gcgaaaaauc aauaaggaga caacaagaug ugcgaacucg au                    42

<210> SEQ ID NO 38
<211> LENGTH: 349
<212> TYPE: RNA
<213> ORGANISM: Artificial sequence
<220> FEATURE:
<223> OTHER INFORMATION: Synthetic nucleic acid sequence

<400> SEQUENCE: 38
gugucuugcg aggauaagug cauuaugaau aucuuacaua uaugugugac cucaaaaugg    60
uucaauauug acaacaaaau ugucgaucac cgcccuugau uugcccuucu guagccauca   120
ccagagccaa accgauuaga uucaaugu ga ucuauuuguu ugcuauaucu uaauuuugcc   180
uuuugcaaag gucaucucuc guuuauuuac uuguuuuagu aaaugauggu gcuugcauau   240
auaucuggcg aauuaaucgg uauagcagau guaauauuca cagggaucac uguaauuaaa   300
auaaaugaag gauuauguaa uggaaaacuu uaaacaucuc ccugaaccg              349

<210> SEQ ID NO 39
<211> LENGTH: 352
<212> TYPE: RNA
<213> ORGANISM: Artificial sequence
<220> FEATURE:
<223> OTHER INFORMATION: Synthetic nucleic acid sequence

<400> SEQUENCE: 39
gcgaaaaauc aauaaggaga caacaagaug ugcgaacucg auauaugugu gaccucaaaa    60
ugguucaaua uugacaacaa aauugucgau caccgcccuu gauuugcccu ucuguagcca   120
ucaccagagc caaaccgauu agauucaaug ugaucuauuu guuugcuaua ucuuaauuuu   180
gccuuuugca aaggucaucu cucguuuauu uacuuguuuu aguaaaugau ggugcuugca   240
uauauaucug gcgaauuaau cgguauagca gauguaauau ucacagggau cacuguaauu   300
aaaauaaaug aaggauuaug uaauggaaaa cuuuaaacau cucccugaac cg           352

<210> SEQ ID NO 40
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 40
ucgcacaucu guugucuga uuauugauuu uucgcgaaac cauuugauca uaugacaaga    60
uguguaucca ccuuaacuua augauuuuua ccaaaaucau uaggggauuc aucag        115

<210> SEQ ID NO 41
<211> LENGTH: 377
<212> TYPE: RNA
<213> ORGANISM: Artificial sequence
<220> FEATURE:
<223> OTHER INFORMATION: Synthetic nucleic acid sequence

<400> SEQUENCE: 41
gaauucuacc auucaccucu uggauuuggg uauuaaagag gagaaaggua ccaugaauau    60
cuuacauaua ugugugaccu caaaaugguu caauauugac aacaaaauug ucgauaccg   120 cccuugauuu gcccuucugu agccaucacc agagccaaac cgauuagauu caaugugauc   180
uauuuguuug cuauaucuua auuuugccuu uugcaaaggu caucucucgu uuauuuacuu   240
```

```
guuuuaguaa augauggugc uugcauauau aucuggcgaa uuaaucggua uagcagaugu    300
aauauucaca gggaucacug uaauuaaaau aaaugaagga uuauguaaug gaaaacuuua    360
aacaucuccc ugaaccg                                                    377
```

```
<210> SEQ ID NO 42
<211> LENGTH: 71
<212> TYPE: RNA
<213> ORGANISM: Artificial sequence
<220> FEATURE:
<223> OTHER INFORMATION: Synthetic nucleic acid sequence

<400> SEQUENCE: 42
acccaaaucc aggaggugau ugguaguggu gguuaaugaa aauuaacuua cuacuaccau    60
auaucucuag a                                                          71
```

```
<210> SEQ ID NO 43
<211> LENGTH: 104
<212> TYPE: DNA
<213> ORGANISM: Artificial sequence
<220> FEATURE:
<223> OTHER INFORMATION: Synthetic nucleic acid sequence

<400> SEQUENCE: 43
ggtgatacca gatttcgcga aaaatcccTT ggcagcacct cgcacatctt gttgtctgat    60
tattgatttt tcgcgaaacc atttgatcat atgacaagat tgag                     104
```

```
<210> SEQ ID NO 44
<211> LENGTH: 95
<212> TYPE: DNA
<213> ORGANISM: Artificial sequence
<220> FEATURE:
<223> OTHER INFORMATION: Synthetic nucleic acid sequence

<400> SEQUENCE: 44
ggtgatacca gcctgaccaa aggcccttgg cagcacctct ttgaatgatg tcgttcacaa    60
actttggtca gggcgtgagc gactcctttt tattt                               95
```

```
<210> SEQ ID NO 45
<211> LENGTH: 96
<212> TYPE: DNA
<213> ORGANISM: Artificial sequence
<220> FEATURE:
<223> OTHER INFORMATION: Synthetic nucleic acid sequence

<400> SEQUENCE: 45
ggtgatacca gcatcgtctt gatgcccttg gcagcacctc tttgaatggt gctgcccaca    60
aactttggtc agggcgtggg cgactccttt ttattt                              96
```

```
<210> SEQ ID NO 46
<211> LENGTH: 96
<212> TYPE: DNA
<213> ORGANISM: Artificial sequence
<220> FEATURE:
<223> OTHER INFORMATION: Synthetic nucleic acid sequence

<400> SEQUENCE: 46
ggtgatacca gcatcgtctt gatgcccttg gcagcacctc tttgaatggt gctgccctgc    60
aactttggcg agggacaggg cgactccttt ttattt                              96
```

```
<210> SEQ ID NO 47
```

```
<211> LENGTH: 79
<212> TYPE: DNA
<213> ORGANISM: Artificial sequence
<220> FEATURE:
<223> OTHER INFORMATION: Synthetic nucleic acid sequence

<400> SEQUENCE: 47
aaacatgagg accacccatg ttctttgaat ggtgtggtcc acaaactttg gtcagggcgt      60
gagccactcc tttttattt                                                   79

<210> SEQ ID NO 48
<211> LENGTH: 79
<212> TYPE: DNA
<213> ORGANISM: Artificial sequence
<220> FEATURE:
<223> OTHER INFORMATION: Synthetic nucleic acid sequence

<400> SEQUENCE: 48
aaacatgagg accacccatg ttctttgaat ggtgtggtcc tgcaactttg gcgagggaca      60
gagccactcc tttttattt                                                   79

<210> SEQ ID NO 49
<211> LENGTH: 96
<212> TYPE: DNA
<213> ORGANISM: Artificial sequence
<220> FEATURE:
<223> OTHER INFORMATION: Synthetic nucleic acid sequence

<400> SEQUENCE: 49
ggtgatacca gcatcgtctt gatgcccttg gcagcacctc tttgaatggt gctgcccaca      60
aactttggtc agggcgtgag cgactccttt ttattt                                96

<210> SEQ ID NO 50
<211> LENGTH: 96
<212> TYPE: DNA
<213> ORGANISM: Artificial sequence
<220> FEATURE:
<223> OTHER INFORMATION: Synthetic nucleic acid sequence

<400> SEQUENCE: 50
ggtgatacca gcatcgtctt gatgcccttg gcagcacctc tttgaatggt gctgcccaca      60
aactttggtc agggcgtgag cggctccttt ttattt                                96

<210> SEQ ID NO 51
<211> LENGTH: 96
<212> TYPE: DNA
<213> ORGANISM: Artificial sequence
<220> FEATURE:
<223> OTHER INFORMATION: Synthetic nucleic acid sequence

<400> SEQUENCE: 51
ggtgatacca gcatcgtctt gatgcccttg gcagcacctc tttgaatggt gctgctcaca      60
aactttggtc agggcgtgag cggctccttt ttattt                                96

<210> SEQ ID NO 52
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 52
gcgaaaaauc aauaaggaga caacaagaug ugcgaacucg au                         42
```

<210> SEQ ID NO 53
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 53
ccgaaaaauc aauaaggaga caacaagaug ugcgaacucg au					42

<210> SEQ ID NO 54
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 54
gggaaaaauc aauaaggaga caacaagaug ugcgaacucg au					42

<210> SEQ ID NO 55
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 55
gcgauaaauc aauaaggaga caacaagaug ugcgaacucg au					42

<210> SEQ ID NO 56
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 56
cggaaaaauc aauaaggaga caacaagaug ugcgaacucg au					42

<210> SEQ ID NO 57
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 57
cccaaaaauc aauaaggaga caacaagaug ugcgaacucg au					42

<210> SEQ ID NO 58
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 58
ccguaaaauc aauaaggaga caacaagaug ugcgaacucg au					42

<210> SEQ ID NO 59
<211> LENGTH: 42
<212> TYPE: RNA
<213> ORGANISM: Artificial sequence
<220> FEATURE:

<223> OTHER INFORMATION: Synthetic nucleic acid sequence

<400> SEQUENCE: 59
ccgauaaauc aauaaggaga caacaagaug ugcgaacucg au                              42

<210> SEQ ID NO 60
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 60
ggcaaaaauc aauaaggaga caacaagaug ugcgaacucg au                              42

<210> SEQ ID NO 61
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 61
ggguaaaauc aauaaggaga caacaagaug ugcgaacucg au                              42

<210> SEQ ID NO 62
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 62
gggauaaauc aauaaggaga caacaagaug ugcgaacucg au                              42

<210> SEQ ID NO 63
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 63
gccuaaaauc aauaaggaga caacaagaug ugcgaacucg au                              42

<210> SEQ ID NO 64
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 64
gccauaaauc aauaaggaga caacaagaug ugcgaacucg au                              42

<210> SEQ ID NO 65
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 65
gcguuaaauc aauaaggaga caacaagaug ugcgaacucg au                              42

```
<210> SEQ ID NO 66
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 66
cgcaaaaauc aauaaggaga caacaagaug ugcgaacucg au                              42

<210> SEQ ID NO 67
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 67
cgguaaaauc aauaaggaga caacaagaug ugcgaacucg au                              42

<210> SEQ ID NO 68
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 68
cggauaaauc aauaaggaga caacaagaug ugcgaacucg au                              42

<210> SEQ ID NO 69
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 69
cccuaaaauc aauaaggaga caacaagaug ugcgaacucg au                              42

<210> SEQ ID NO 70
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 70
cccauaaauc aauaaggaga caacaagaug ugcgaacucg au                              42

<210> SEQ ID NO 71
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 71
ccguuaaauc aauaaggaga caacaagaug ugcgaacucg au                              42

<210> SEQ ID NO 72
<211> LENGTH: 42
<212> TYPE: RNA
<213> ORGANISM: Artificial sequence
<220> FEATURE:
<223> OTHER INFORMATION: Synthetic nucleic acid sequence
```

<400> SEQUENCE: 72
ggcuaaaauc aauaaggaga caacaagaug ugcgaacucg au    42

<210> SEQ ID NO 73
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 73
ggcauaaauc aauaaggaga caacaagaug ugcgaacucg au    42

<210> SEQ ID NO 74
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 74
ggguuaaauc aauaaggaga caacaagaug ugcgaacucg au    42

<210> SEQ ID NO 75
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 75
gccuuaaauc aauaaggaga caacaagaug ugcgaacucg au    42

<210> SEQ ID NO 76
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 76
cgcuaaaauc aauaaggaga caacaagaug ugcgaacucg au    42

<210> SEQ ID NO 77
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 77
cgcauaaauc aauaaggaga caacaagaug ugcgaacucg au    42

<210> SEQ ID NO 78
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 78
cgguuaaauc aauaaggaga caacaagaug ugcgaacucg au    42

<210> SEQ ID NO 79
<211> LENGTH: 42

```
<212> TYPE: RNA
<213> ORGANISM: Artificial sequence
<220> FEATURE:
<223> OTHER INFORMATION: Synthetic nucleic acid sequence

<400> SEQUENCE: 79
cccuuaaauc aauaaggaga caacaagaug ugcgaacucg au              42

<210> SEQ ID NO 80
<211> LENGTH: 42
<212> TYPE: RNA
<213> ORGANISM: Artificial sequence
<220> FEATURE:
<223> OTHER INFORMATION: Synthetic nucleic acid sequence

<400> SEQUENCE: 80
cgcuuaaauc aauaaggaga caacaagaug ugcgaacucg au              42

<210> SEQ ID NO 81
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 81
ccguaaaaaa ucaauaagga gacaacaaga ugugcgaacu cgau            44

<210> SEQ ID NO 82
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 82
gccuaaaaaa ucaauaagga gacaacaaga ugugcgaacu cgau            44

<210> SEQ ID NO 83
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 83
cgguaaaaaa ucaauaagga gacaacaaga ugugcgaacu cgau            44

<210> SEQ ID NO 84
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 84
cccuaaaaaa ucaauaagga gacaacaaga ugugcgaacu cgau            44

<210> SEQ ID NO 85
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 85
```

-continued ggcuaaaaaa ucaauaagga gacaacaaga ugugcgaacu cgau          44

<210> SEQ ID NO 86
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 86
ccgauaaaaa ucaauaagga gacaacaaga ugugcgaacu cgau          44

<210> SEQ ID NO 87
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 87
gggauaaaaa ucaauaagga gacaacaaga ugugcgaacu cgau          44

<210> SEQ ID NO 88
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 88
gccauaaaaa ucaauaagga gacaacaaga ugugcgaacu cgau          44

<210> SEQ ID NO 89
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 89
cggauaaaaa ucaauaagga gacaacaaga ugugcgaacu cgau          44

<210> SEQ ID NO 90
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 90
cccauaaaaa ucaauaagga gacaacaaga ugugcgaacu cgau          44

<210> SEQ ID NO 91
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 91
ggcauaaaaa ucaauaagga gacaacaaga ugugcgaacu cgau          44

<210> SEQ ID NO 92
<211> LENGTH: 44
<212> TYPE: RNA
<213> ORGANISM: Artificial sequence

```
<220> FEATURE:
<223> OTHER INFORMATION: Synthetic nucleic acid sequence

<400> SEQUENCE: 92
ccgcgaaaaa ucaauaagga gacaacaaga ugugcgaacu cgau            44

<210> SEQ ID NO 93
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 93
gggcgaaaaa ucaauaagga gacaacaaga ugugcgaacu cgau            44

<210> SEQ ID NO 94
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 94
gcccgaaaaa ucaauaagga gacaacaaga ugugcgaacu cgau            44

<210> SEQ ID NO 95
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 95
cggcgaaaaa ucaauaagga gacaacaaga ugugcgaacu cgau            44

<210> SEQ ID NO 96
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 96
ggccgaaaaa ucaauaagga gacaacaaga ugugcgaacu cgau            44

<210> SEQ ID NO 97
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 97
ccggcaaaaa ucaauaagga gacaacaaga ugugcgaacu cgau            44

<210> SEQ ID NO 98
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 98
ggggcaaaaa ucaauaagga gacaacaaga ugugcgaacu cgau            44
```

<210> SEQ ID NO 99
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 99
gccgcaaaaa ucaauaagga gacaacaaga ugugcgaacu cgau         44

<210> SEQ ID NO 100
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 100
cgggcaaaaa ucaauaagga gacaacaaga ugugcgaacu cgau         44

<210> SEQ ID NO 101
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 101
cccgcaaaaa ucaauaagga gacaacaaga ugugcgaacu cgau         44

<210> SEQ ID NO 102
<211> LENGTH: 44
<212> TYPE: RNA
<213> ORGANISM: Artificial sequence
<220> FEATURE:
<223> OTHER INFORMATION: Synthetic nucleic acid sequence

<400> SEQUENCE: 102
ggcgcaaaaa ucaauaagga gacaacaaga ugugcgaacu cgau         44

<210> SEQ ID NO 103
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 103
ucgcacaucu uguugucuga uuauugauuu uucgcgaaac cauuugauca uaugacaaga     60
uguguaucca ccuuaacuua augauuuuua ccaaaaucau uagggauuc aucag          115

<210> SEQ ID NO 104
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 104
ucgcacaucu uguugucuga uuauugauuu uucgggaaac cauuugauca uaugacaaga     60
uguguaucca ccuuaacuua augauuuuua ccaaaaucau uagggauuc aucag          115

<210> SEQ ID NO 105
<211> LENGTH: 115

```
<212> TYPE: RNA
<213> ORGANISM: Artificial sequence
<220> FEATURE:
<223> OTHER INFORMATION: Synthetic nucleic acid sequence

<400> SEQUENCE: 105
ucgcacaucu uguugucuga uuauugauuu ucccgaaac cauuugauca uaugacaaga      60
uguguaucca ccuuaacuua augauuuuua ccaaaaucau uaggggauuc aucag         115

<210> SEQ ID NO 106
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 106
ucgcacaucu uguugucuga uuauugauuu aucgcgaaac cauuugauca uaugacaaga    60
uguguaucca ccuuaacuua augauuuuua ccaaaaucau uaggggauuc aucag         115

<210> SEQ ID NO 107
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 107
ucgcacaucu uguugucuga uuauugauuu uuccggaaac cauuugauca uaugacaaga    60
uguguaucca ccuuaacuua augauuuuua ccaaaaucau uaggggauuc aucag         115

<210> SEQ ID NO 108
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 108
ucgcacaucu uguugucuga uuauugauuu uugggaaac cauuugauca uaugacaaga     60
uguguaucca ccuuaacuua augauuuuua ccaaaaucau uaggggauuc aucag         115

<210> SEQ ID NO 109
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 109
ucgcacaucu uguugucuga uuauugauuu uacgggaaac cauuugauca uaugacaaga    60
uguguaucca ccuuaacuua augauuuuua ccaaaaucau uaggggauuc aucag         115

<210> SEQ ID NO 110
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 110
ucgcacaucu uguugucuga uuauugauuu aucgggaaac cauuugauca uaugacaaga    60
```
uguguaucca ccuuaacuua augauuuuua ccaaaaucau aggggauuc aucag    115

<210> SEQ ID NO 111
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 111
ucgcacaucu uguugucuga uuauugauuu uugccgaaac cauuugauca uaugacaaga    60
uguguaucca ccuuaacuua augauuuuua ccaaaaucau aggggauuc aucag    115

<210> SEQ ID NO 112
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 112
ucgcacaucu uguugucuga uuauugauuu uacccgaaac cauuugauca uaugacaaga    60
uguguaucca ccuuaacuua augauuuuua ccaaaaucau aggggauuc aucag    115

<210> SEQ ID NO 113
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 113
ucgcacaucu uguugucuga uuauugauuu aucccgaaac cauuugauca uaugacaaga    60
uguguaucca ccuuaacuua augauuuuua ccaaaaucau aggggauuc aucag    115

<210> SEQ ID NO 114
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 114
ucgcacaucu uguugucuga uuauugauuu uaggcgaaac cauuugauca uaugacaaga    60
uguguaucca ccuuaacuua augauuuuua ccaaaaucau aggggauuc aucag    115

<210> SEQ ID NO 115
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 115
ucgcacaucu uguugucuga uuauugauuu auggcgaaac cauuugauca uaugacaaga    60
uguguaucca ccuuaacuua augauuuuua ccaaaaucau aggggauuc aucag    115

<210> SEQ ID NO 116
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 116
ucgcacaucu uguugucuga uuauugauuu aacgcgaaac cauuugauca uaugacaaga    60
uguguaucca ccuuaacuua augauuuuua ccaaaaucau uagggauuc aucag    115

<210> SEQ ID NO 117
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 117
ucgcacaucu uguugucuga uuauugauuu uugcggaaac cauuugauca uaugacaaga    60
uguguaucca ccuuaacuua augauuuuua ccaaaaucau uagggauuc aucag    115

<210> SEQ ID NO 118
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 118
ucgcacaucu uguugucuga uuauugauuu uaccggaaac cauuugauca uaugacaaga    60
uguguaucca ccuuaacuua augauuuuua ccaaaaucau uagggauuc aucag    115

<210> SEQ ID NO 119
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 119
ucgcacaucu uguugucuga uuauugauuu auccggaaac cauuugauca uaugacaaga    60
uguguaucca ccuuaacuua augauuuuua ccaaaaucau uagggauuc aucag    115

<210> SEQ ID NO 120
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 120
ucgcacaucu uguugucuga uuauugauuu uaggggaaac cauuugauca uaugacaaga    60
uguguaucca ccuuaacuua augauuuuua ccaaaaucau uagggauuc aucag    115

<210> SEQ ID NO 121
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 121
ucgcacaucu uguugucuga uuauugauuu auggggaaac cauuugauca uaugacaaga    60
uguguaucca ccuuaacuua augauuuuua ccaaaaucau uagggauuc aucag    115

<210> SEQ ID NO 122

```
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 122
ucgcacaucu uguugucuga uuauugauuu aacgggaaac cauuugauca uaugacaaga      60
uguguaucca ccuuaacuua augauuuuua ccaaaaucau uaggggauuc aucag          115

<210> SEQ ID NO 123
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 123
ucgcacaucu uguugucuga uuauugauuu uagccgaaac cauuugauca uaugacaaga     60
uguguaucca ccuuaacuua augauuuuua ccaaaaucau uaggggauuc aucag          115

<210> SEQ ID NO 124
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 124
ucgcacaucu uguugucuga uuauugauuu augccgaaac cauuugauca uaugacaaga     60
uguguaucca ccuuaacuua augauuuuua ccaaaaucau uaggggauuc aucag          115

<210> SEQ ID NO 125
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 125
ucgcacaucu uguugucuga uuauugauuu aacccgaaac cauuugauca uaugacaaga     60
uguguaucca ccuuaacuua augauuuuua ccaaaaucau uaggggauuc aucag          115

<210> SEQ ID NO 126
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 126
ucgcacaucu uguugucuga uuauugauuu aaggcgaaac cauuugauca uaugacaaga     60
uguguaucca ccuuaacuua augauuuuua ccaaaaucau uaggggauuc aucag          115

<210> SEQ ID NO 127
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 127
ucgcacaucu uguugucuga uuauugauuu uagcggaaac cauuugauca uaugacaaga     60
```
uguguaucca ccuuaacuua augauuuuua ccaaaaucau uagggauuc aucag    115

<210> SEQ ID NO 128
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 128
ucgcacaucu uguugucuga uuauugauuu augcggaaac cauuugauca uaugacaaga    60
uguguaucca ccuuaacuua augauuuuua ccaaaaucau uagggauuc aucag    115

<210> SEQ ID NO 129
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 129
ucgcacaucu uguugucuga uuauugauuu aaccggaaac cauuugauca uaugacaaga    60
uguguaucca ccuuaacuua augauuuuua ccaaaaucau uagggauuc aucag    115

<210> SEQ ID NO 130
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 130
ucgcacaucu uguugucuga uuauugauuu aagggaaac cauuugauca uaugacaaga    60
uguguaucca ccuuaacuua augauuuuua ccaaaaucau uagggauuc aucag    115

<210> SEQ ID NO 131
<211> LENGTH: 115
<212> TYPE: RNA
<213> ORGANISM: Artificial sequence
<220> FEATURE:
<223> OTHER INFORMATION: Synthetic nucleic acid sequence

<400> SEQUENCE: 131
ucgcacaucu uguugucuga uuauugauuu aagcggaaac cauuugauca uaugacaaga    60
uguguaucca ccuuaacuua augauuuuua ccaaaaucau uagggauuc aucag    115

<210> SEQ ID NO 132
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 132
ucgcacaucu uguugucuga uuauugauuu uuuacgggaa accauuugau cauaugacaa    60
gauguguauc caccuuaacu uaaugauuuu uaccaaaauc auuagggau ucaucag    117

<210> SEQ ID NO 133
<211> LENGTH: 117
<212> TYPE: RNA
<213> ORGANISM: Artificial sequence
<220> FEATURE:

<223> OTHER INFORMATION: Synthetic nucleic acid sequence

<400> SEQUENCE: 133
ucgcacaucu uguugucuga uuauugauuu uuuaggcgaa accauuugau cauaugacaa    60
gauguguauc caccuuaacu uaaugauuuu uaccaaaauc auuaggggau ucaucag    117

<210> SEQ ID NO 134
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 134
ucgcacaucu uguugucuga uuauugauuu uuuaccggaa accauuugau cauaugacaa    60
gauguguauc caccuuaacu uaaugauuuu uaccaaaauc auuaggggau ucaucag    117

<210> SEQ ID NO 135
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 135
ucgcacaucu uguugucuga uuauugauuu uuuagcggaa accauuugau cauaugacaa    60
gauguguauc caccuuaacu uaaugauuuu uaccaaaauc auuaggggau ucaucag    117

<210> SEQ ID NO 136
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 136
ucgcacaucu uguugucuga uuauugauuu uuuagccgaa accauuugau cauaugacaa    60
gauguguauc caccuuaacu uaaugauuuu uaccaaaauc auuaggggau ucaucag    117

<210> SEQ ID NO 137
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 137
ucgcacaucu uguugucuga uuauugauuu uuaucgggaa accauuugau cauaugacaa    60
gauguguauc caccuuaacu uaaugauuuu uaccaaaauc auuaggggau ucaucag    117

<210> SEQ ID NO 138
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 138
ucgcacaucu uguugucuga uuauugauuu uuauccgaa accauuugau cauaugacaa    60
gauguguauc caccuuaacu uaaugauuuu uaccaaaauc auuaggggau ucaucag    117

```
<210> SEQ ID NO 139
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 139
ucgcacaucu uguugucuga uuauugauuu uuauggcgaa accauuugau cauaugacaa      60
gauguguauc caccuuaacu uaaugauuuu uaccaaaauc auuaggggau ucaucag        117

<210> SEQ ID NO 140
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 140
ucgcacaucu uguugucuga uuauugauuu uuauccggaa accauuugau cauaugacaa      60
gauguguauc caccuuaacu uaaugauuuu uaccaaaauc auuaggggau ucaucag        117

<210> SEQ ID NO 141
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 141
ucgcacaucu uguugucuga uuauugauuu uuauggggaa accauuugau cauaugacaa      60
gauguguauc caccuuaacu uaaugauuuu uaccaaaauc auuaggggau ucaucag        117

<210> SEQ ID NO 142
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 142
ucgcacaucu uguugucuga uuauugauuu uuaugccgaa accauuugau cauaugacaa      60
gauguguauc caccuuaacu uaaugauuuu uaccaaaauc auuaggggau ucaucag        117

<210> SEQ ID NO 143
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 143
ucgcacaucu uguugucuga uuauugauuu uucgcgggaa accauuugau cauaugacaa      60
gauguguauc caccuuaacu uaaugauuuu uaccaaaauc auuaggggau ucaucag        117

<210> SEQ ID NO 144
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 144
```
ucgcacaucu uguugucuga uuauugauuu uucgcccgaa accauuugau cauaugacaa    60
gauguguauc caccuuaacu uaaugauuuu uaccaaaauc auuaggggau ucaucag       117

<210> SEQ ID NO 145
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 145
ucgcacaucu uguugucuga uuauugauuu uucgggcgaa accauuugau cauaugacaa    60
gauguguauc caccuuaacu uaaugauuuu uaccaaaauc auuaggggau ucaucag       117

<210> SEQ ID NO 146
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 146
ucgcacaucu uguugucuga uuauugauuu uucgccggaa accauuugau cauaugacaa    60
gauguguauc caccuuaacu uaaugauuuu uaccaaaauc auuaggggau ucaucag       117

<210> SEQ ID NO 147
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 147
ucgcacaucu uguugucuga uuauugauuu uucggccgaa accauuugau cauaugacaa    60
gauguguauc caccuuaacu uaaugauuuu uaccaaaauc auuaggggau ucaucag       117

<210> SEQ ID NO 148
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 148
ucgcacaucu uguugucuga uuauugauuu uugccgggaa accauuugau cauaugacaa    60
gauguguauc caccuuaacu uaaugauuuu uaccaaaauc auuaggggau ucaucag       117

<210> SEQ ID NO 149
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 149
ucgcacaucu uguugucuga uuauugauuu uugccccgaa accauuugau cauaugacaa    60
gauguguauc caccuuaacu uaaugauuuu uaccaaaauc auuaggggau ucaucag       117

<210> SEQ ID NO 150
<211> LENGTH: 117
<212> TYPE: RNA
<213> ORGANISM: Artificial sequence

```
<220> FEATURE:
<223> OTHER INFORMATION: Synthetic nucleic acid sequence

<400> SEQUENCE: 150
ucgcacaucu uguugucuga uuauugauuu uugcggcgaa accauuugau cauaugacaa        60
gauguguauc caccuuaacu uaaugauuuu uaccaaaauc auuaggggau ucaucag         117

<210> SEQ ID NO 151
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 151
ucgcacaucu uguugucuga uuauugauuu uugcccggaa accauuugau cauaugacaa        60
gauguguauc caccuuaacu uaaugauuuu uaccaaaauc auuagggggau ucaucag        117

<210> SEQ ID NO 152
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 152
ucgcacaucu uguugucuga uuauugauuu uugcggggaa accauuugau cauaugacaa        60
gauguguauc caccuuaacu uaaugauuuu uaccaaaauc auuaggggau ucaucag         117

<210> SEQ ID NO 153
<211> LENGTH: 117
<212> TYPE: RNA
<213> ORGANISM: Artificial sequence
<220> FEATURE:
<223> OTHER INFORMATION: Synthetic nucleic acid sequence

<400> SEQUENCE: 153
ucgcacaucu uguugucuga uuauugauuu uugcgccgaa accauuugau cauaugacaa        60
gauguguauc caccuuaacu uaaugauuuu uaccaaaauc auuaggggau ucaucag         117
```